(12) United States Patent
Jamieson, Jr.

(10) Patent No.: US 8,604,692 B2
(45) Date of Patent: Dec. 10, 2013

(54) MASS SPECTROMETRY ASSAY FOR EIF4E AND EIF4E REGULON ACTIVITY

(75) Inventor: Gordon A. Jamieson, Jr., Arlington, MA (US)

(73) Assignee: Translational Therapeutics, Inc., Arlington, MA (US)

( * ) Notice: Subject to any disclaimer, the term of this patent is extended or adjusted under 35 U.S.C. 154(b) by 265 days.

(21) Appl. No.: 12/775,013

(22) Filed: May 6, 2010

(65) Prior Publication Data

US 2010/0317043 A1     Dec. 16, 2010

Related U.S. Application Data

(63) Continuation-in-part of application No. PCT/US2008/082611, filed on Nov. 6, 2008.

(60) Provisional application No. 60/985,787, filed on Nov. 6, 2007.

(51) Int. Cl.
*H01J 17/26* (2012.01)

(52) U.S. Cl.
USPC ......................................................... 313/564

(58) Field of Classification Search
USPC ......................................................... 313/564
See application file for complete search history.

(56) References Cited

U.S. PATENT DOCUMENTS

| | | | |
|---|---|---|---|
| 6,586,190 B2 | 7/2003 | Petrovich et al. |
| 6,951,757 B2 | 10/2005 | Sabatini |
| 7,258,974 B2 | 8/2007 | Chou |
| 2002/0049307 A1 | 4/2002 | Aebersold et al. |
| 2002/0137888 A1 | 9/2002 | Bernasconi et al. |
| 2003/0228694 A1 | 12/2003 | Sabatini |
| 2005/0176085 A1 | 8/2005 | Nunez et al. |
| 2008/0171394 A1 | 7/2008 | Eriksson et al. |

FOREIGN PATENT DOCUMENTS

| | | |
|---|---|---|
| JP | 2003-107066 A | 4/2003 |
| JP | 2005-189232 A | 7/2005 |
| JP | 2007-525639 A | 9/2007 |
| WO | WO-00/11208 A1 | 3/2000 |
| WO | WO-2004/070352 A2 | 8/2004 |
| WO | WO-2009-061904 A2 | 5/2009 |
| WO | WO-2009147650 A2 | 12/2009 |

OTHER PUBLICATIONS

Rychlik et al. "Phosphorylation site of eukaryotic initiation factor 4E", JBC, 1987, 262(22):10434-10437.*
Cui, Li, et al. "Comparative proteome analysis of human lung squamous carcinoma tissue," The Chinese-German Journal of Clinical Oncology, 5(4):232-239 (Aug. 1, 2006).
Cutillas, Pedro R, et al. "Quantification of gel-separated proteins and their phosphorylation sites by LC-MS using unlabeled internal standards: analysis of phosphoprotein dynamics in a B cell lymphoma cell line," Molecular & Cellular Proteomics, 4(8):1038-1051 (Aug. 2005).
Gingras, Anne-Claude, et al. "Regulation of 4E-BP1 phosphorylation: A novel two-step mechanism," Genes and Development, 13(11): 1422-1437 (Jun. 1, 1999).
Gygi, S.P., et al. "Protein analysis by mass spectrometry and sequence database searching: tools for cancer research in the post-genomic era," Electrophoresis, 20(2):310-319 (Feb. 1999).
Hale, J.E., et al. "A simplified procedure for the reduction and alkylation of cysteine residues in proteins prior to proteolytic digestion and mass spectral analysis," 333(1):174-181 (Oct. 1, 2004).
Mayya, Viveka, et al. "Absolute quantification of multisite phosphorylation by selective reaction monitoring mass spectrometry: determination of inhibitory phosphorylation status of cyclin-dependent kinases," 5(6):1146-1157 (Jun. 2006).
Whalen, S.G., et al. "Phosphorylation of eIF-4E on serine 209 by protein kinase C is inhibited by the translational repressors, 4E-binding proteins," The Journal of Biological Chemistry, 271(20):11831-11837 (May 17, 1996).
International Search Report for PCT/US2008/082611 mailed Jun. 29, 2009.
Supplementary European Search Report for EP 08 84 6730 mailed Feb. 24, 2011.
International Search Report for PCT/US2011/035559 dated Feb. 8, 2012.
Rychlik, Wojciech, et al. "Phosphorylation Site of Eukaryotic Initiation Factor 4E," The Journal of Biological Chemistry, 262(22): 10434-37 (Aug. 5, 1987).
Japanese Office Action for Application No. 2010-532339 mailed Aug. 26, 2013.

* cited by examiner

*Primary Examiner* — Bin Shen
(74) *Attorney, Agent, or Firm* — Foley Hoag LLP

(57) ABSTRACT

Provided is a highly sensitive high throughput mass spectrometry-based quantitative assay for 4E/4E regulon pathway proteins has been developed which provides for single sample multiplexed analysis, as well as the analysis of protein phosphorylation states. It may be adapted for use as the first single sample analytical method of the 4E/4E regulon biological pathway.

7 Claims, 60 Drawing Sheets

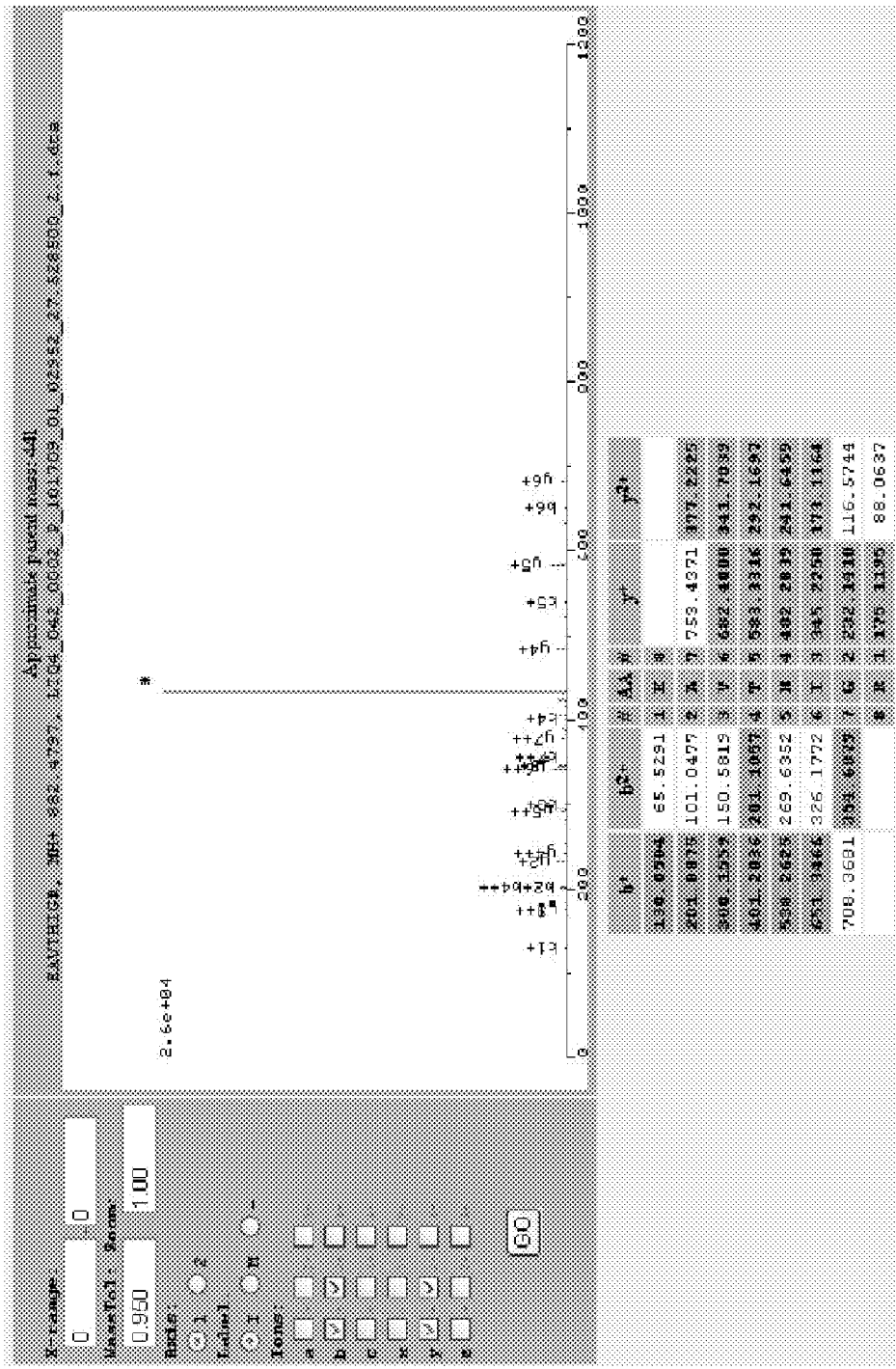
FIG. 1 -- gi|IPI00027485.3|sp|P06730|rs|NP_001959|Eukaryotic translation initiation factor 4E|gs|EIF4E LY400723

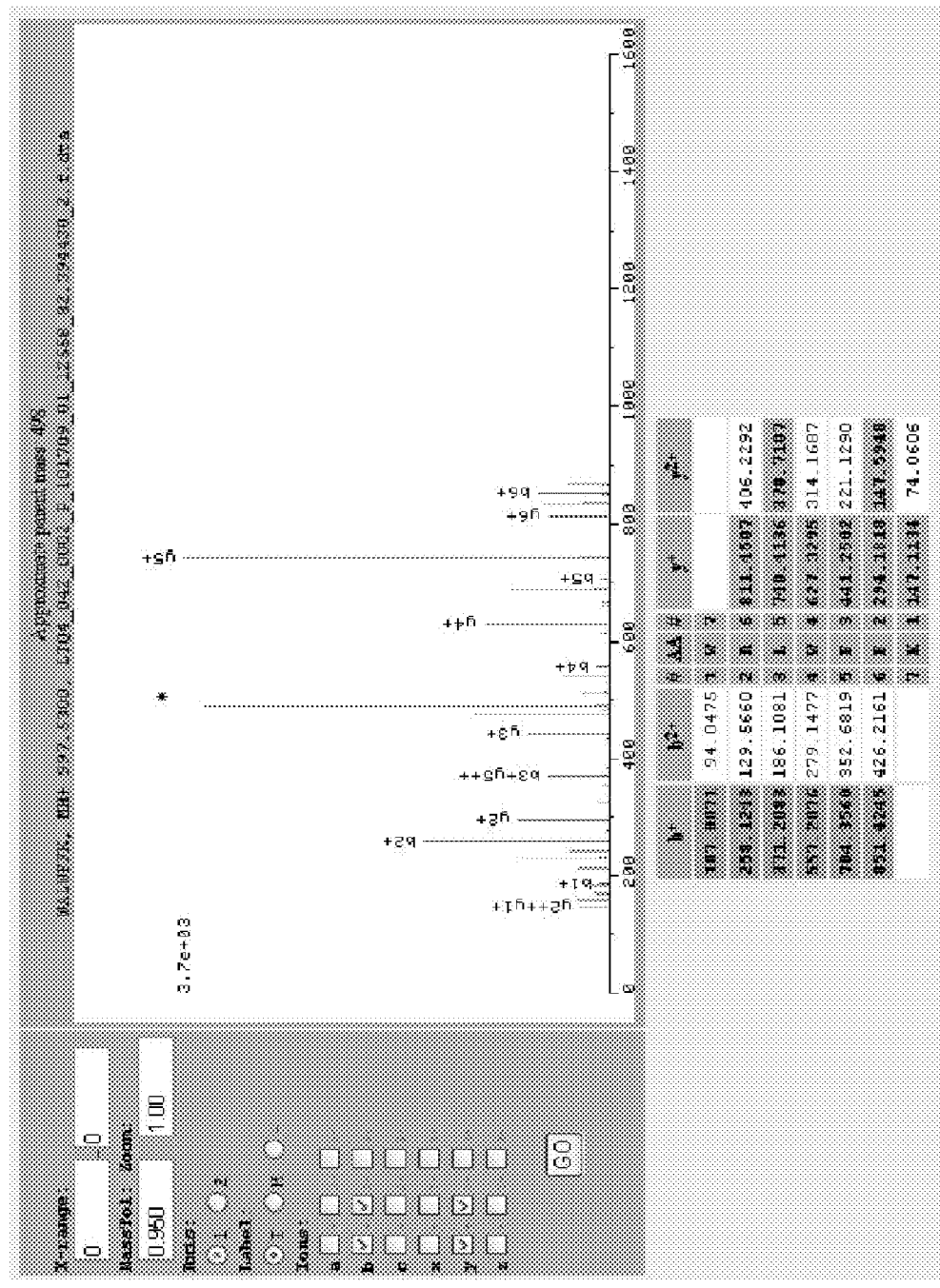
FIG. 1 cont. -- gi|IPI00027485.3|sp|P06730|rs|NP_001959|Eukaryotic translation initiation factor 4E|gs|EIF4E LY400723

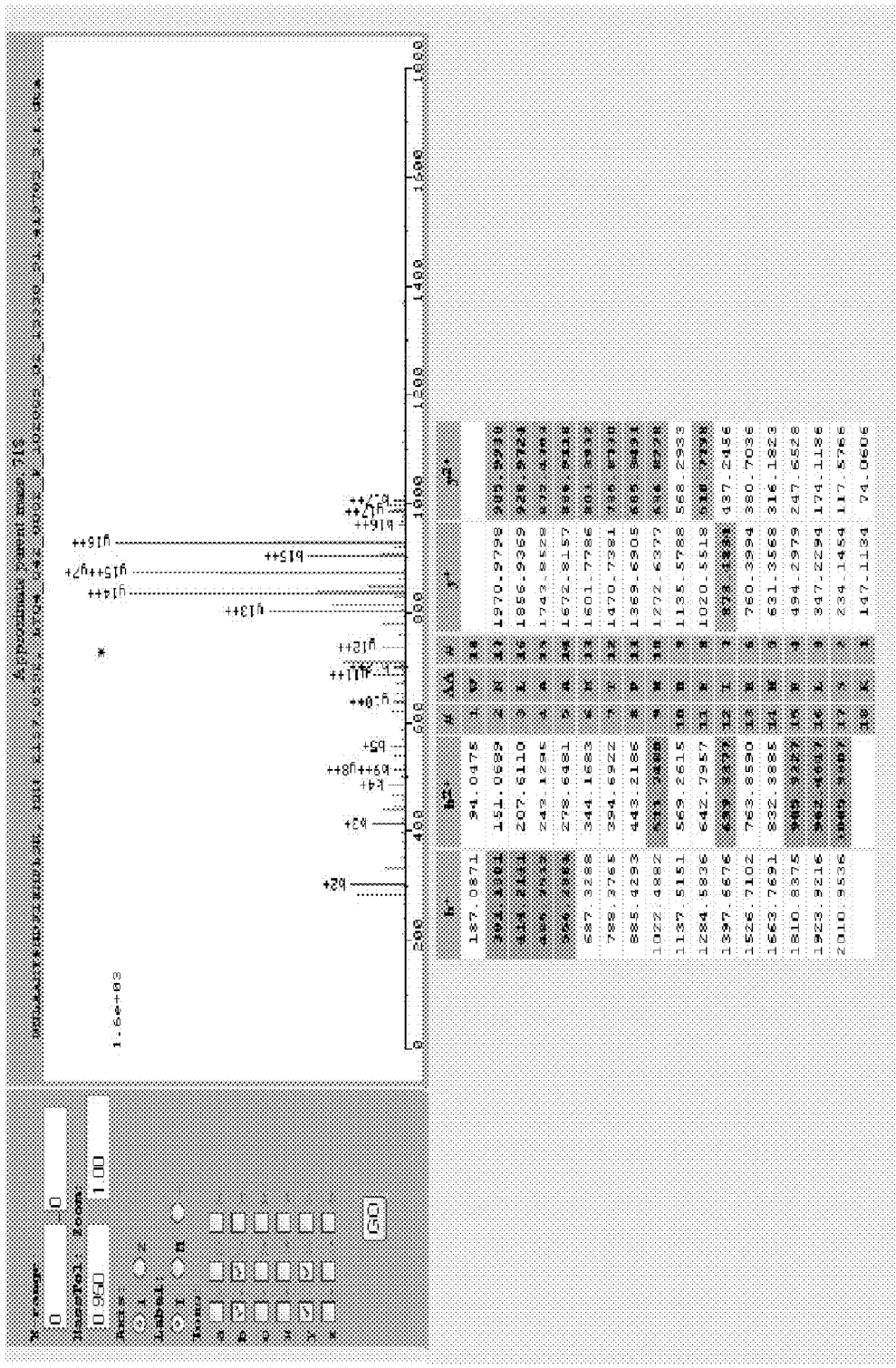
FIG. 1 cont. -- gi|IPI00028098.1|sp|P24385|rs|NP_444284| G1/S-specific cyclin-D1|gs |CCND1 LY403284

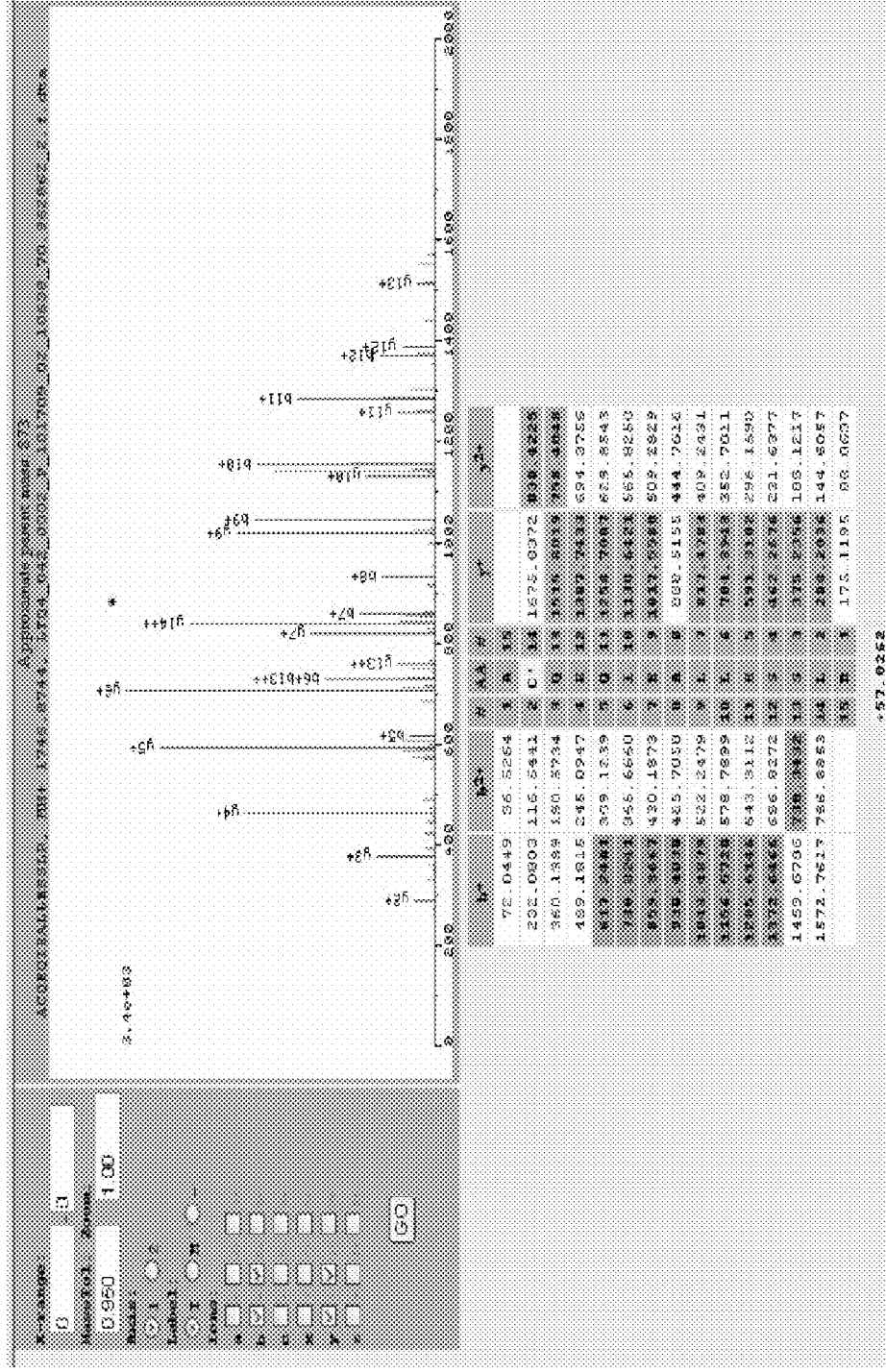
FIG. 1 cont. -- gi|IPI00028098.1|sp|P24385|rs|NP_444284| G1/S-specific cyclin-D1|gs|CCND1 LY403284

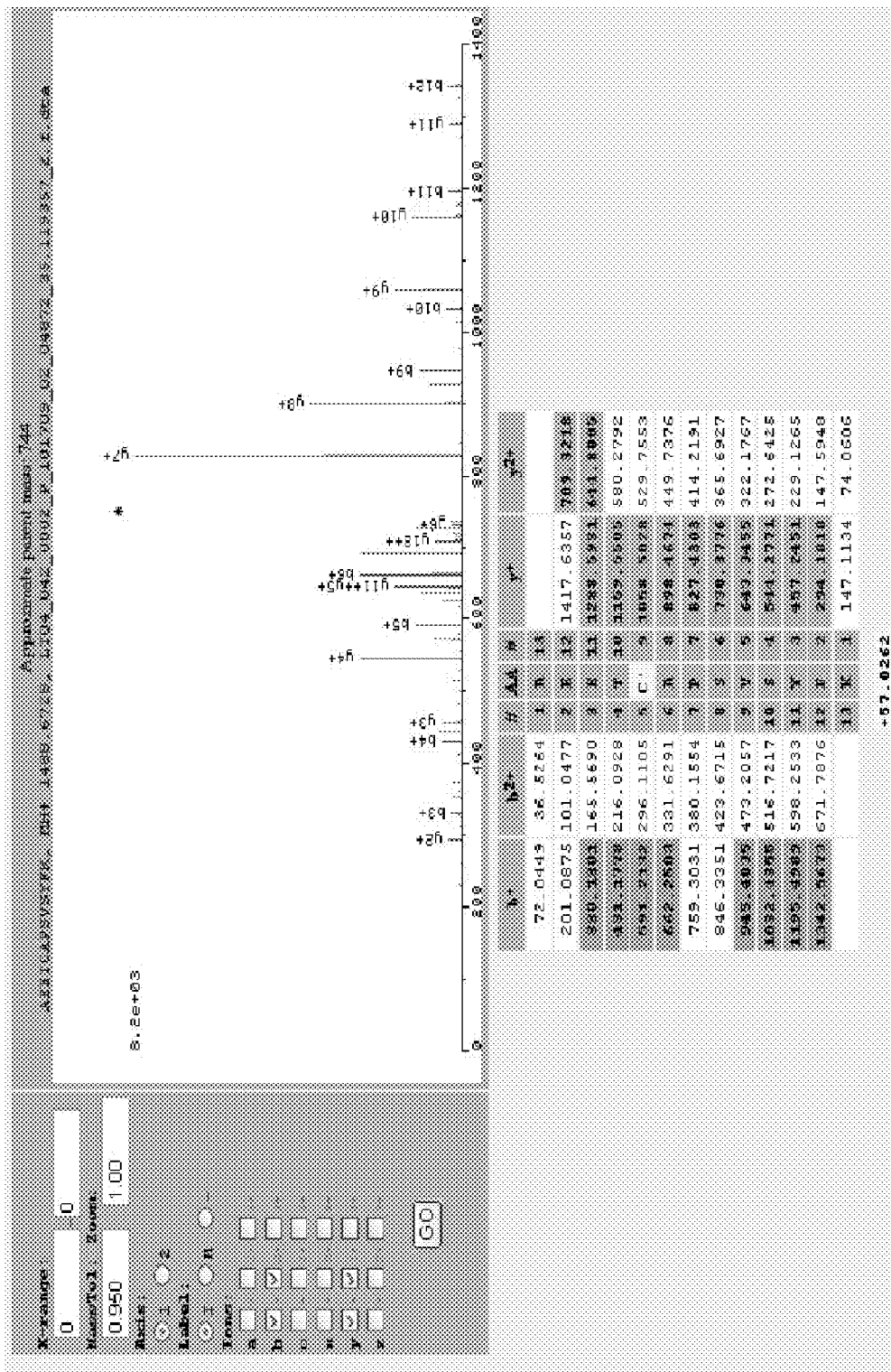
FIG. 1 cont. -- gi||IPI00028098.1|sp|P24385|rs|NP_444284| G1/S-specific cyclin-D1|gs|CCND1 LY403284

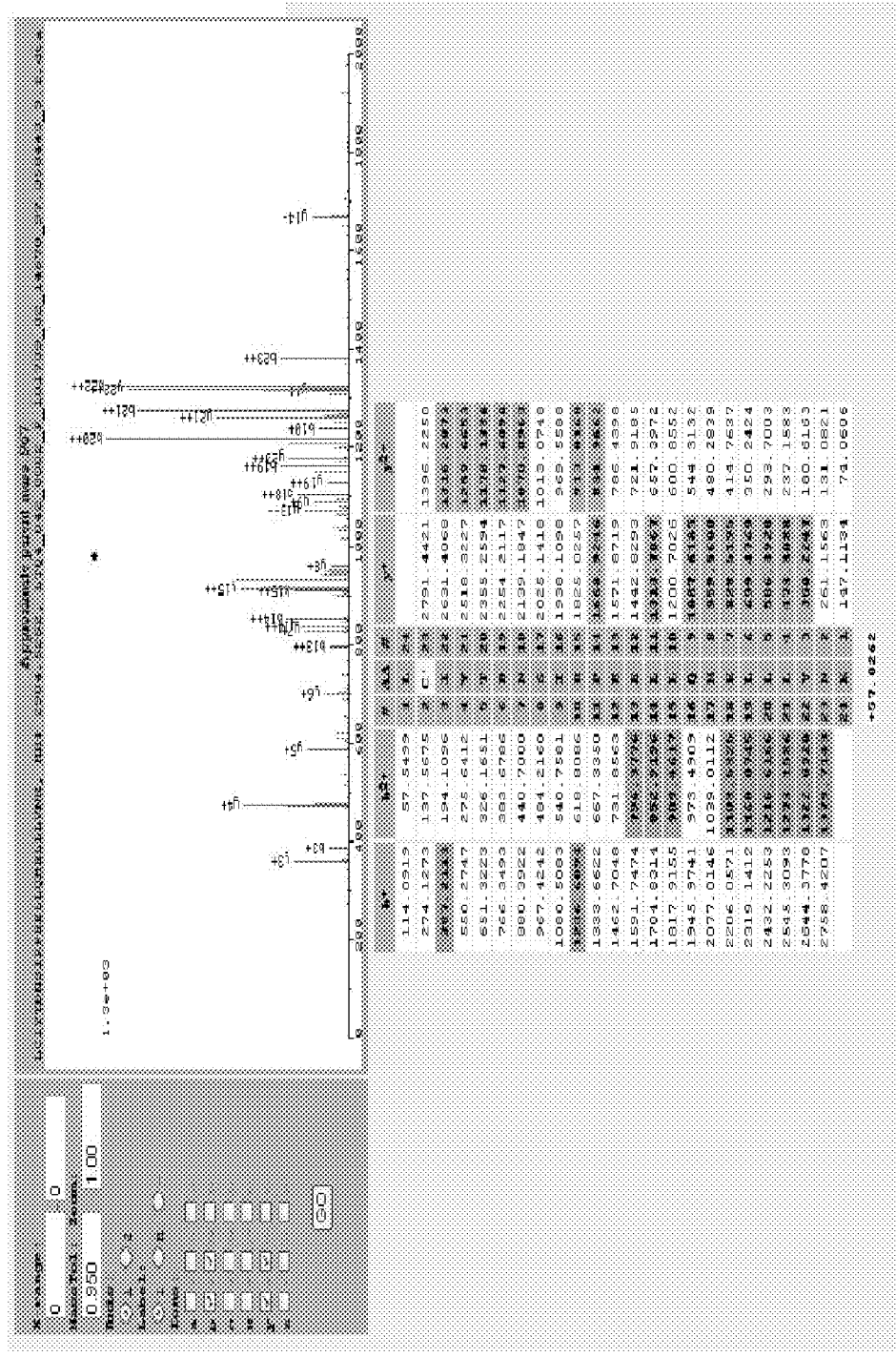
FIG. 1 cont. -- gi|IPI00028098.1|sp|P24385|rs|NP_444284| G1/S-specific cyclin-D1|gs|CCND1 LY403284

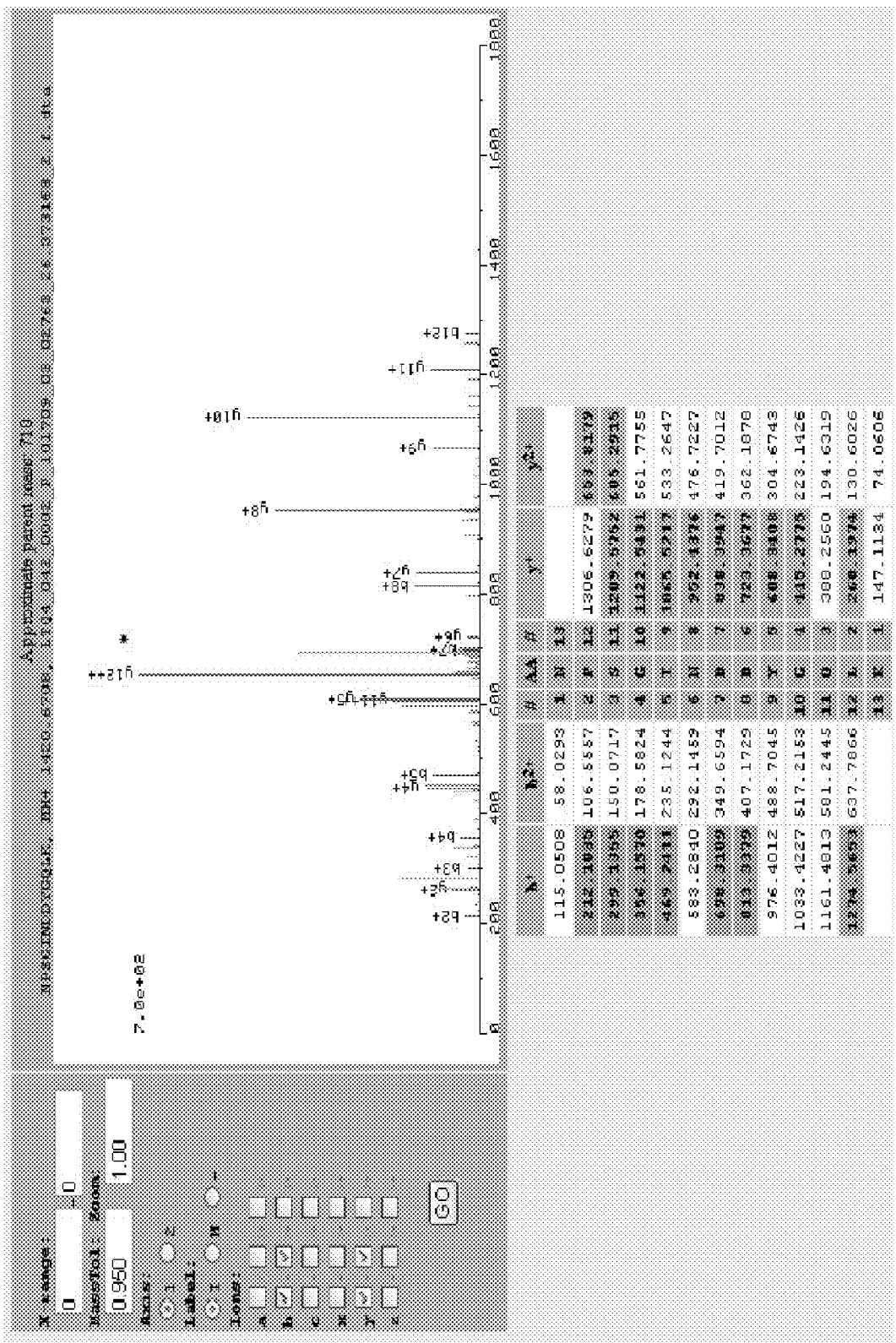
FIG. 1 cont. -- gi|PI00299463.1|sp|O60934|rs|NP_002476| Nibrin|gs|NBN
LY419300

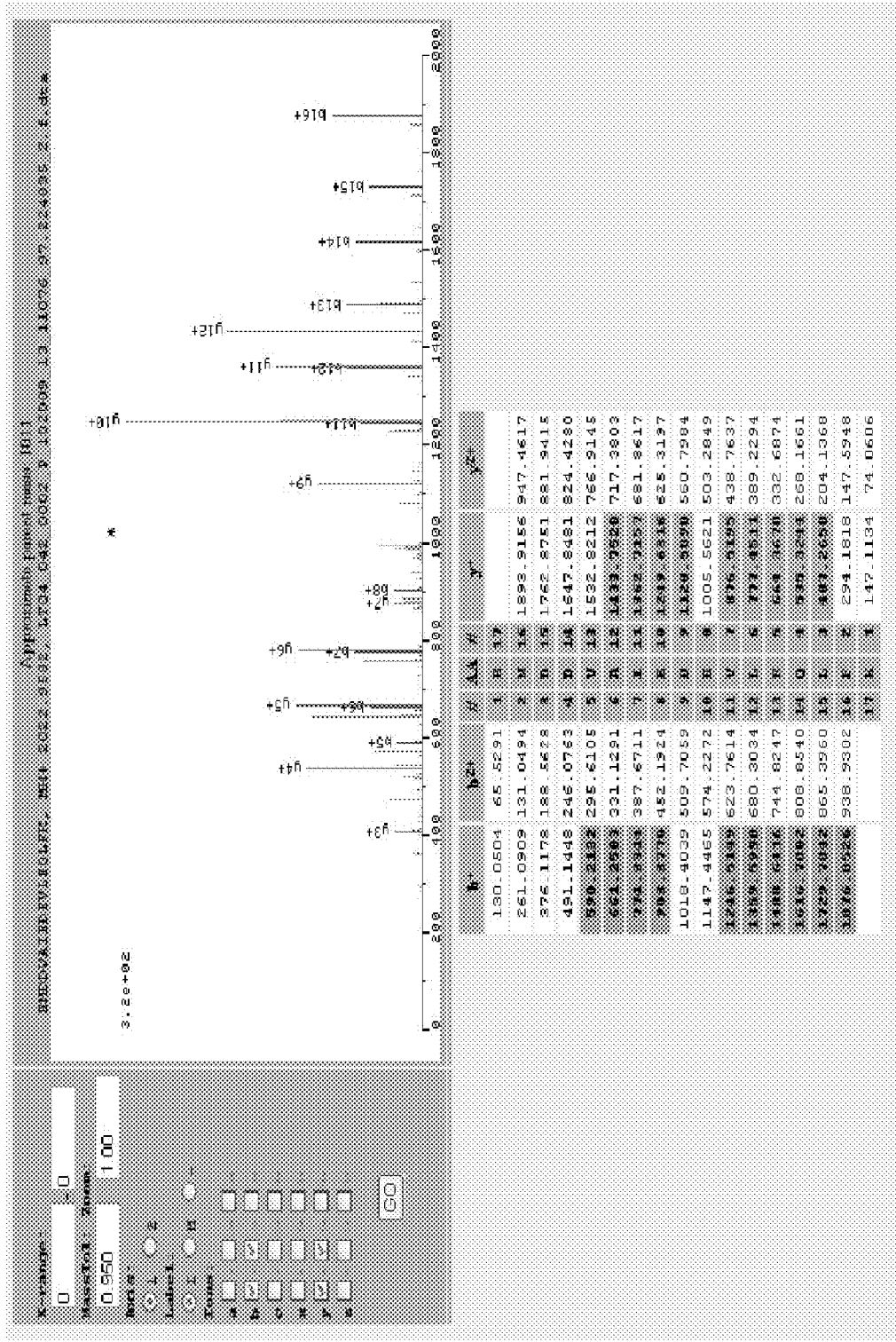
FIG. 1 cont. -- gi|IPI00299463.1 |sp|O60934|rs|NP_002476| Nibrin|gs|NBN
LY419300

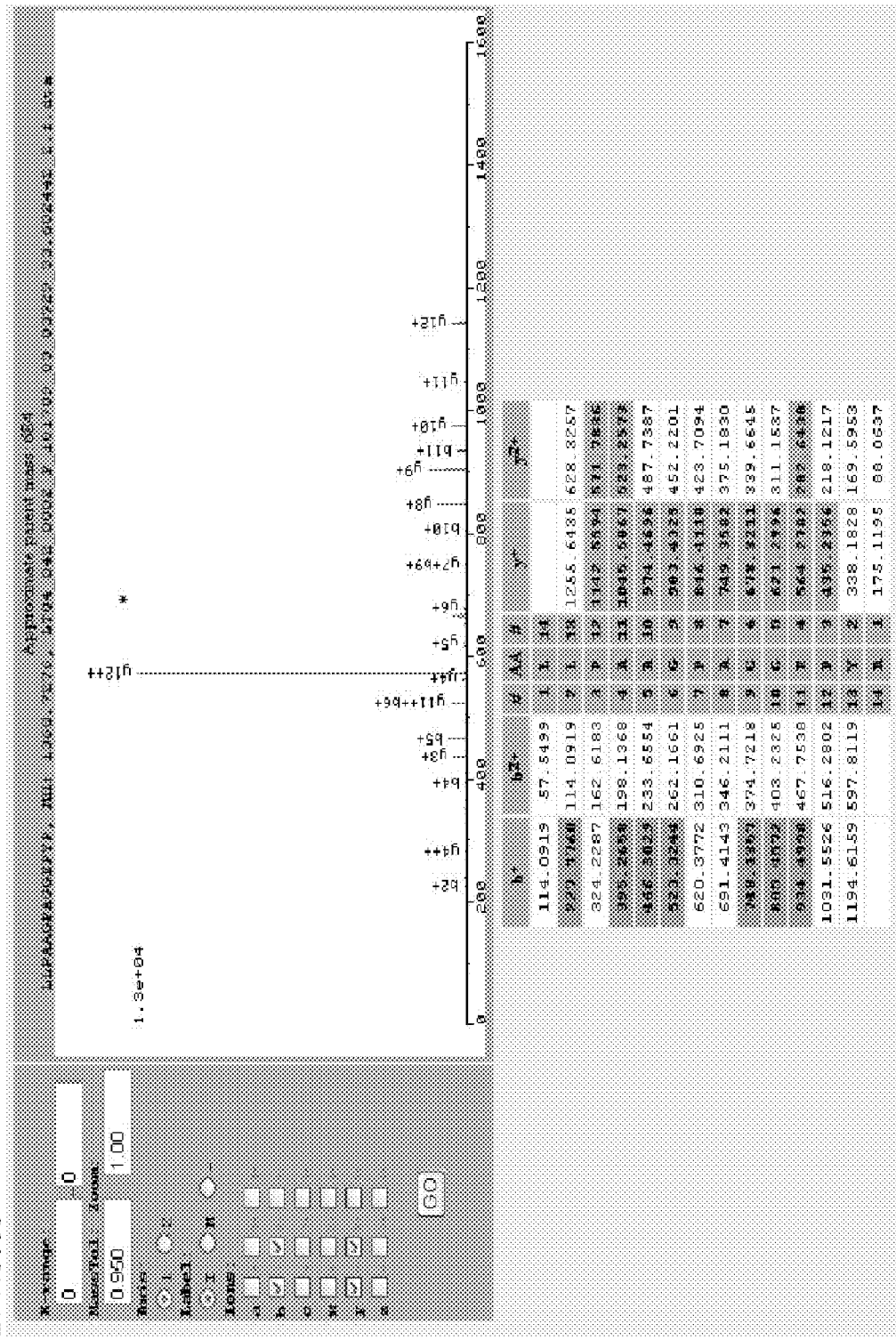
FIG. 1 cont. -- gi|IPI00299463.1 |sp|O60934|rs|NP_002476| Nibrin|gs|NBN LY419300

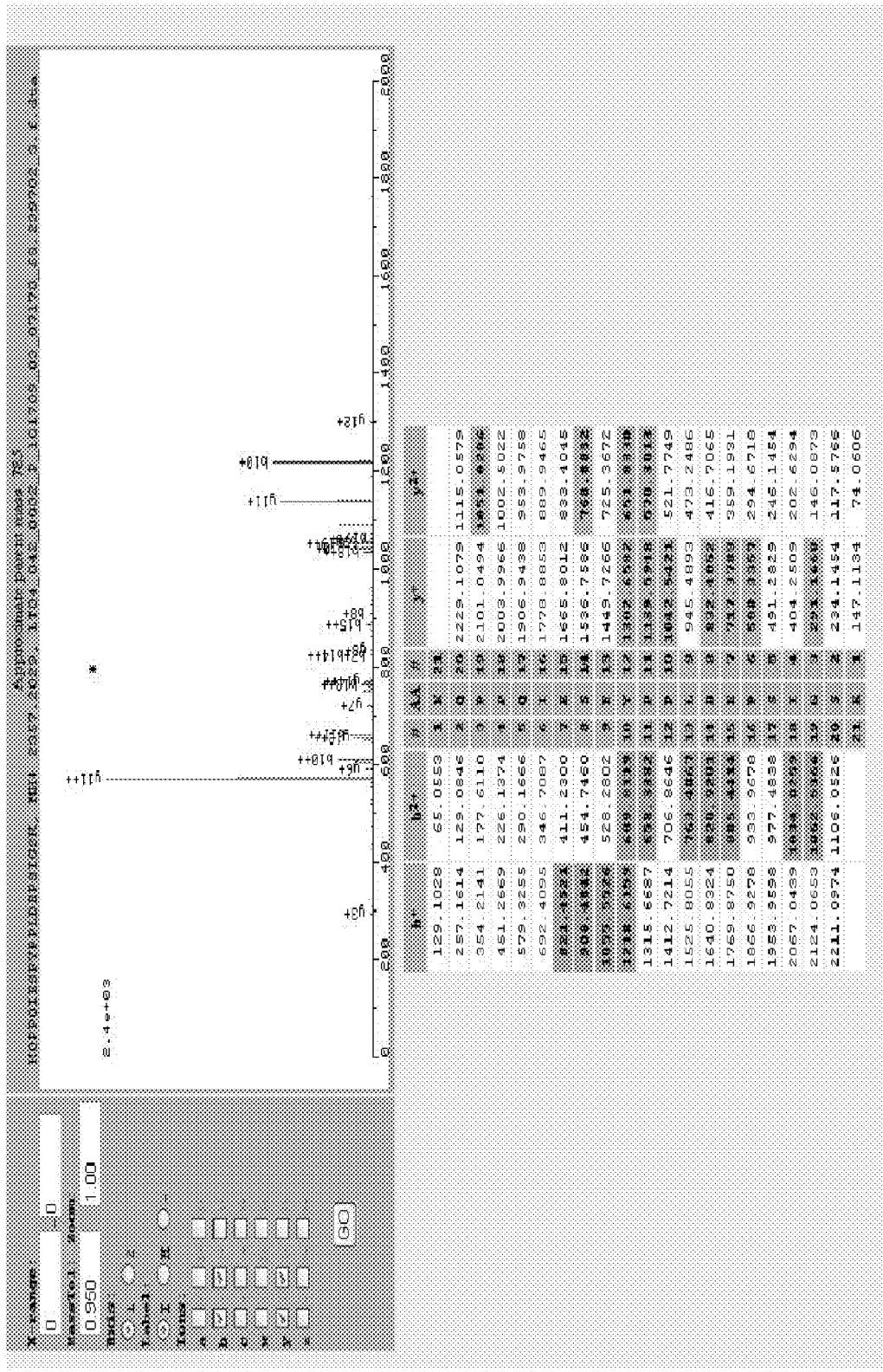
FIG. 1 cont. -- gi|IPI00299463.1|sp|O60934|rs|NP_002476| Nibrin|gs|NBN
LY419300

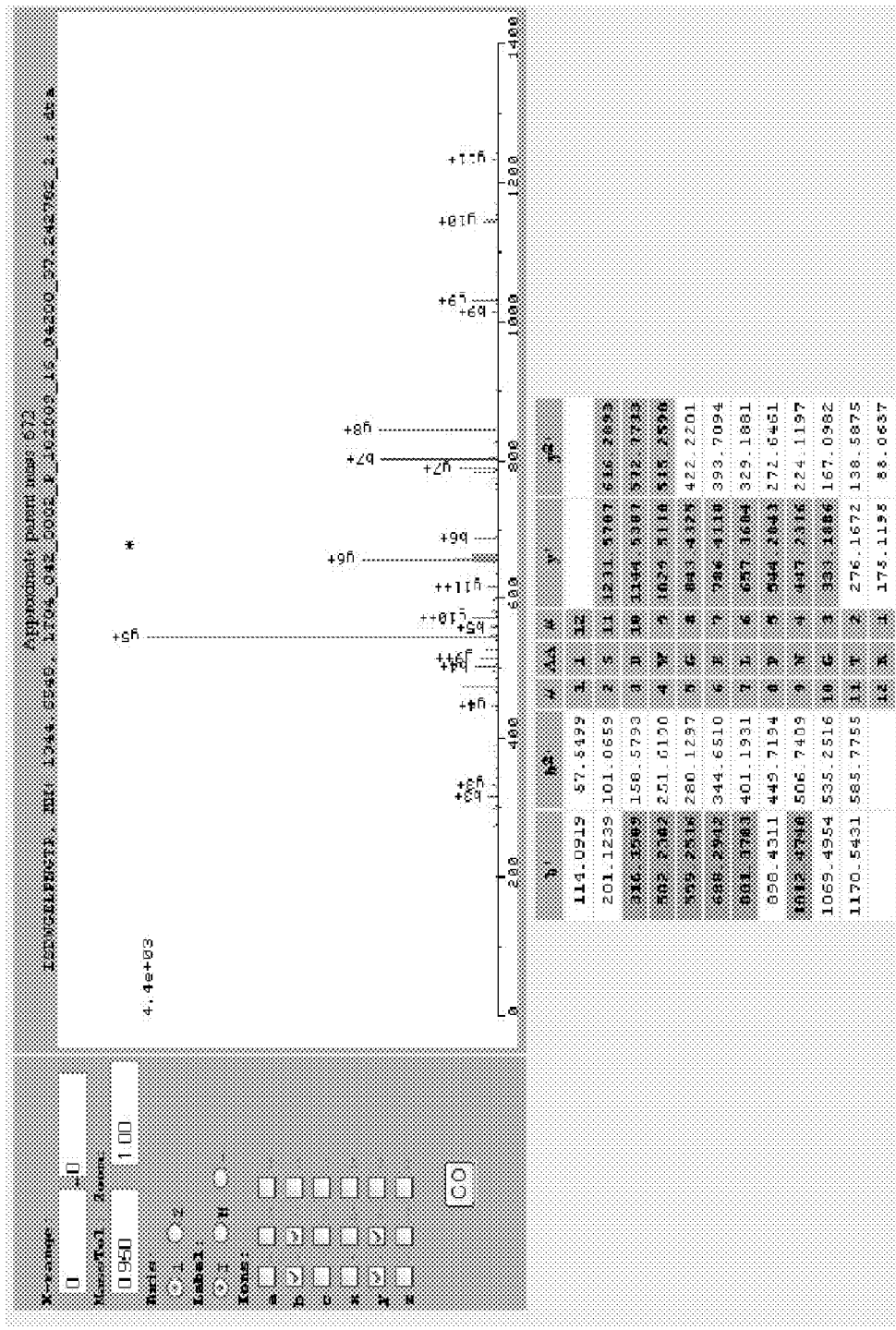
FIG. 1 cont. -- gi|IPI00005014.2|sp|P11309-1|rs|| Isoform 1 of Protooncogene serine/threonine-protein kinase Pim-1|gs|PIM1
LY419183

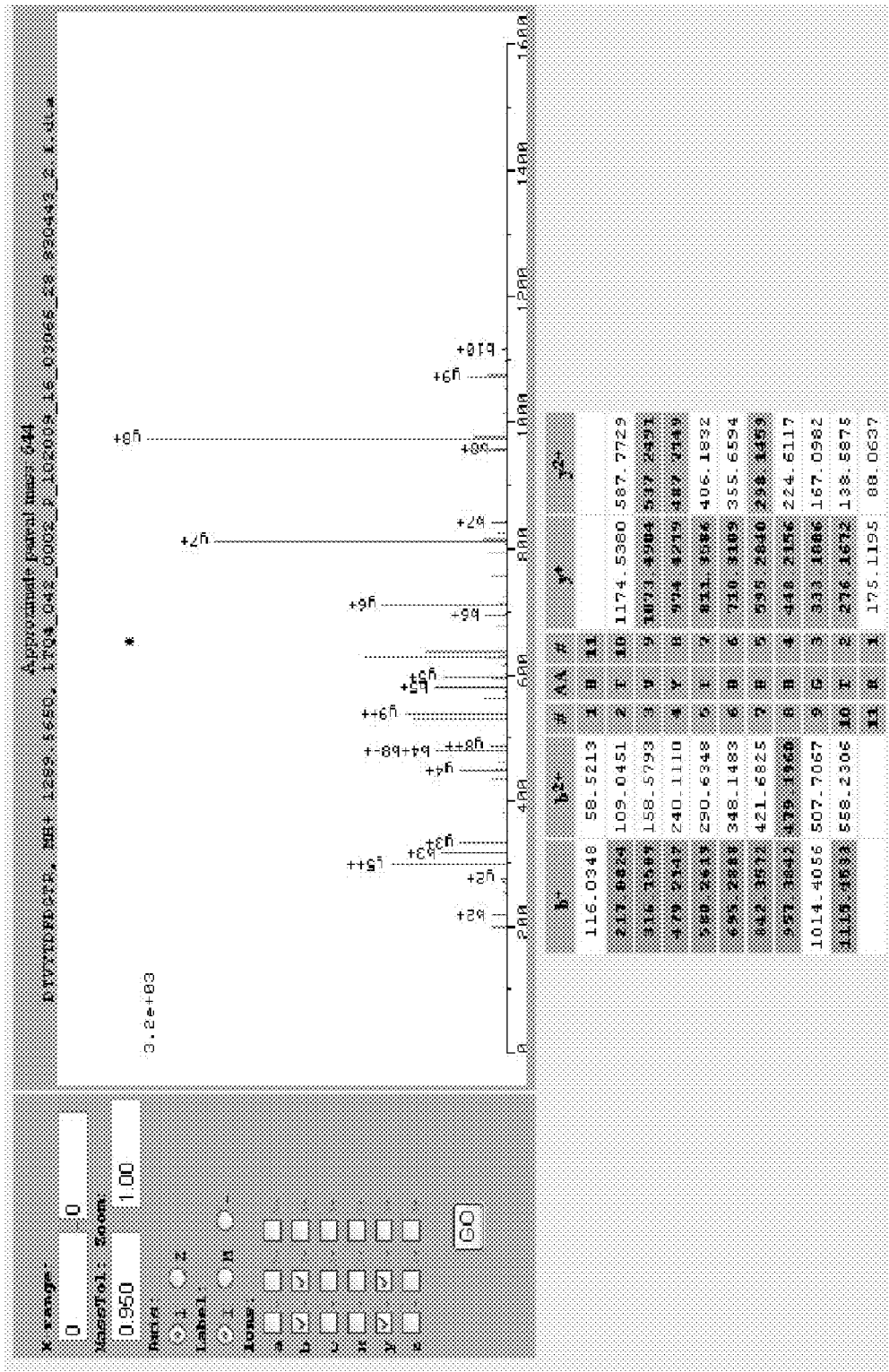
FIG. 1 cont. -- gi||PI00005014.2|sp|P11309-1|rs|| Isoform 1 of Protooncogene serine/threonine-protein kinase Pim-1|gs|PIM1 LY419183

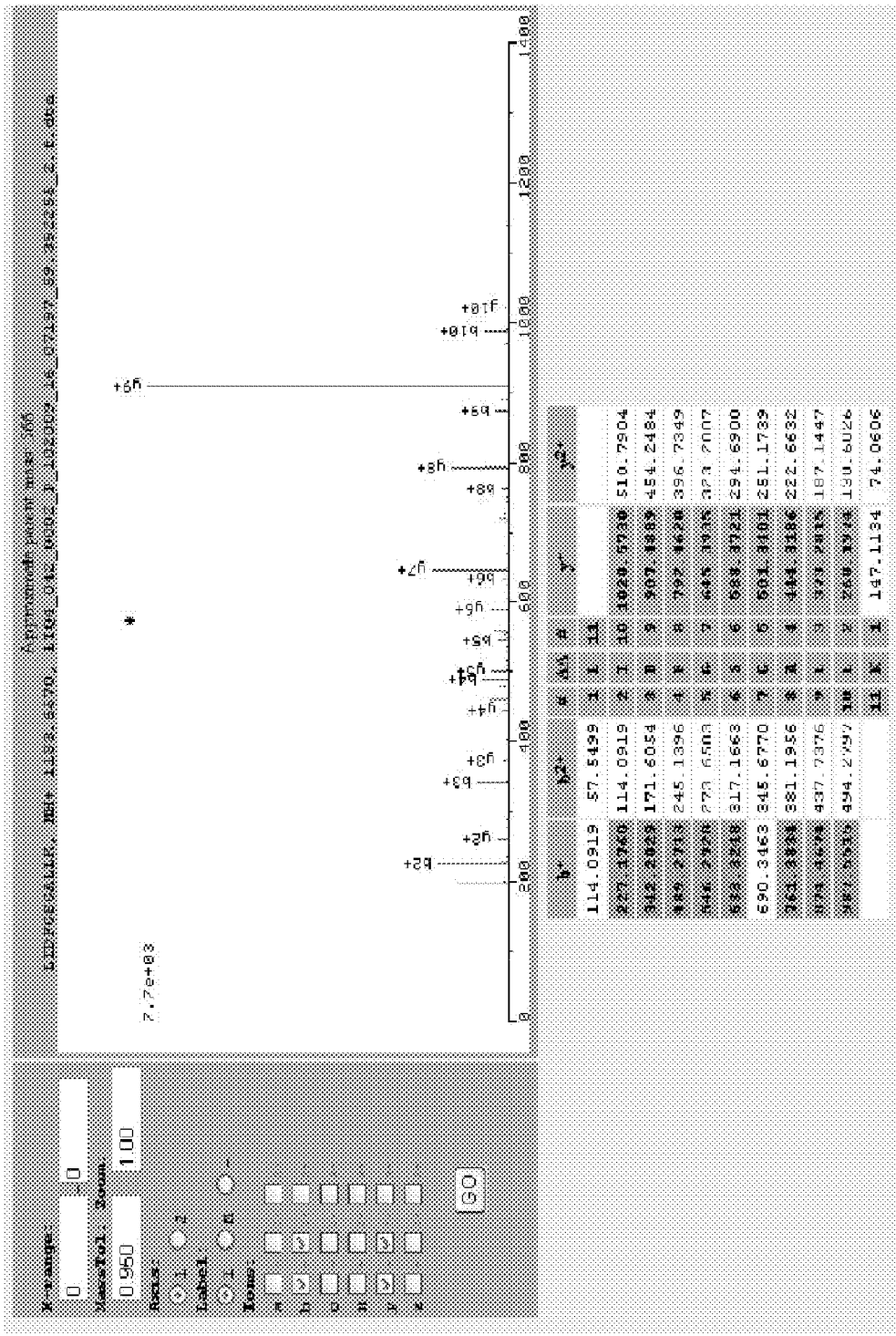
FIG. 1 cont. -- gi|IPI00005014.2|sp|P11309-1|rs|| Isoform 1 of Protooncogene serine/threonine-protein kinase Pim-1|gs|PIM1 LY419183

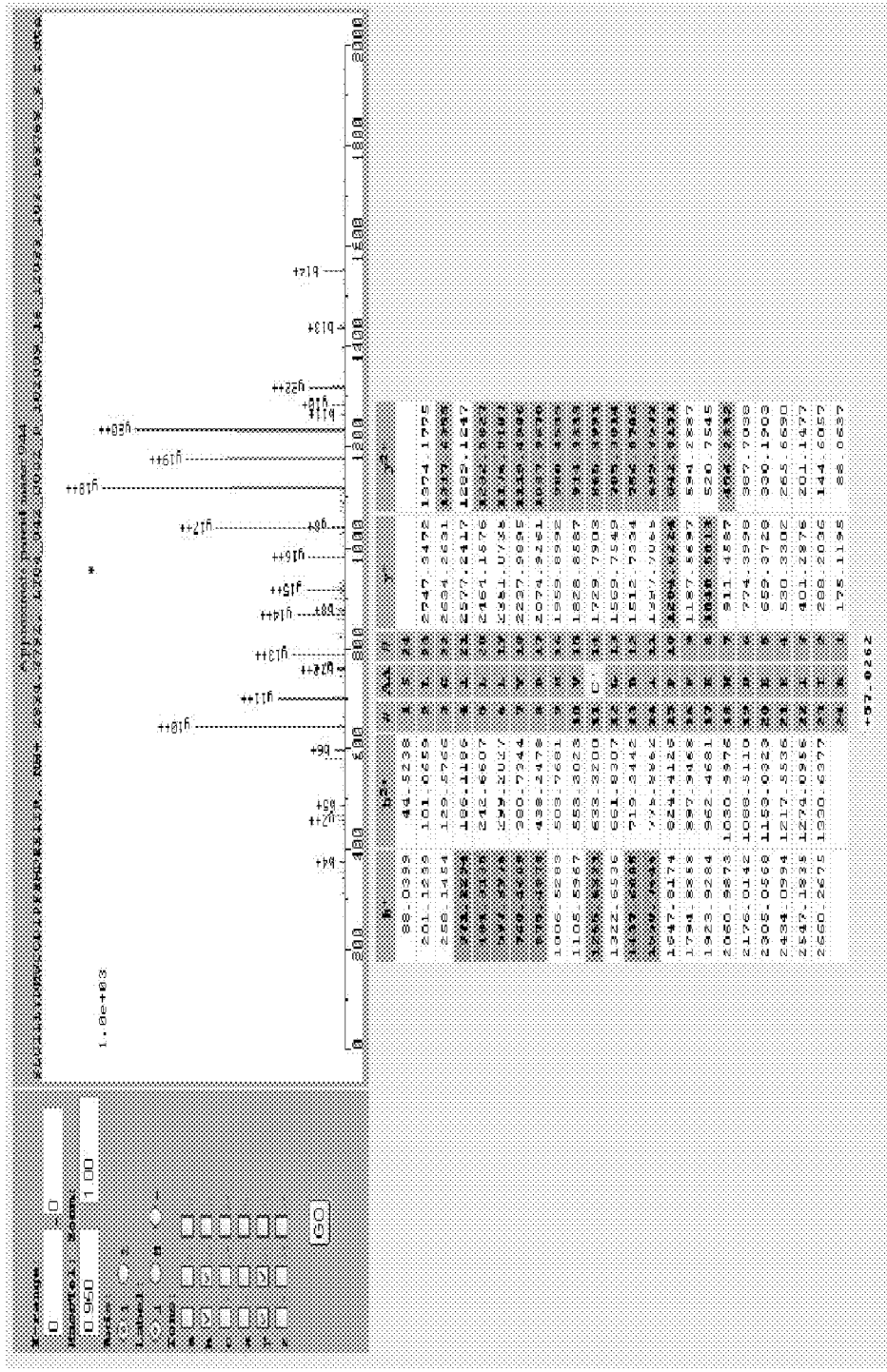
FIG. 1 cont. -- gi|IPI00005014.2|sp|P11309-1|rs|| Isoform 1 of Protooncogene serine/threonine-protein kinase Pim-1|gs|PIM1 LY419183

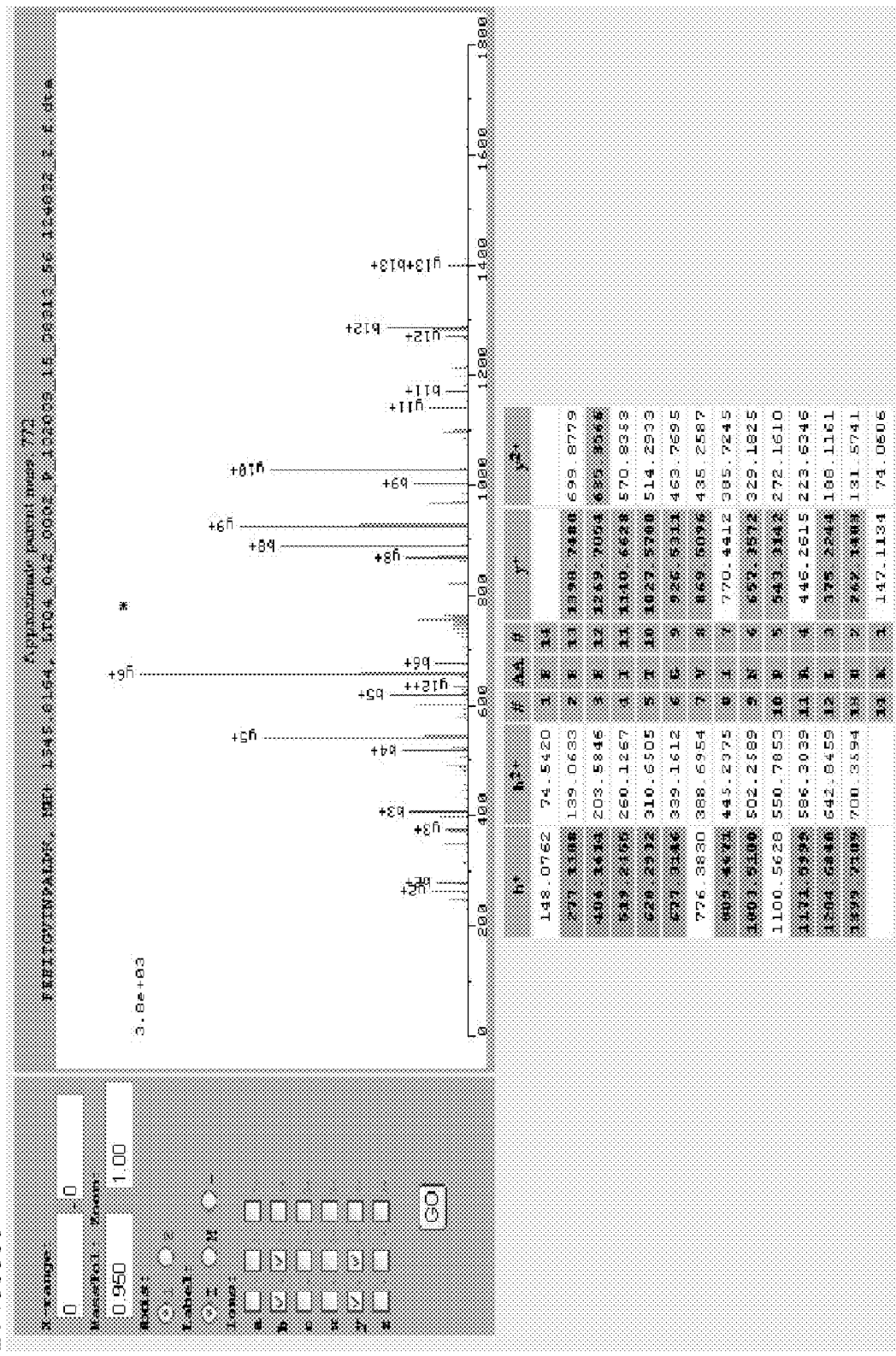
FIG. 1 cont. -- gi|IPI00008497.1|sp|P11926|rs|NP_002530| Ornithine decarboxylase|gs|ODC1 LY400909

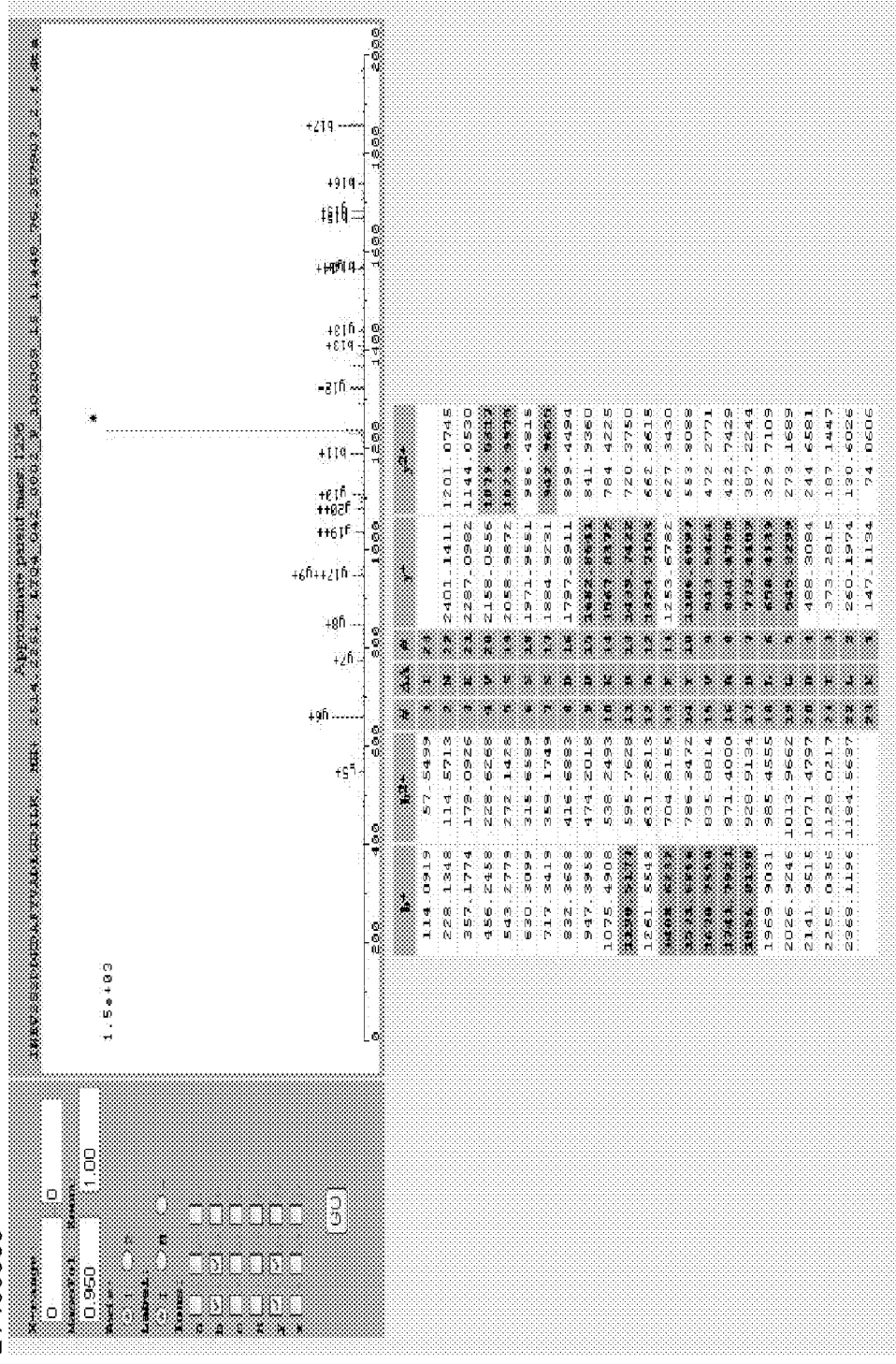
FIG. 1 cont. -- gi|IPI00008497.1|sp|P11926|rs|NP_002530| Ornithine decarboxylase|gs|ODC1 LY400909

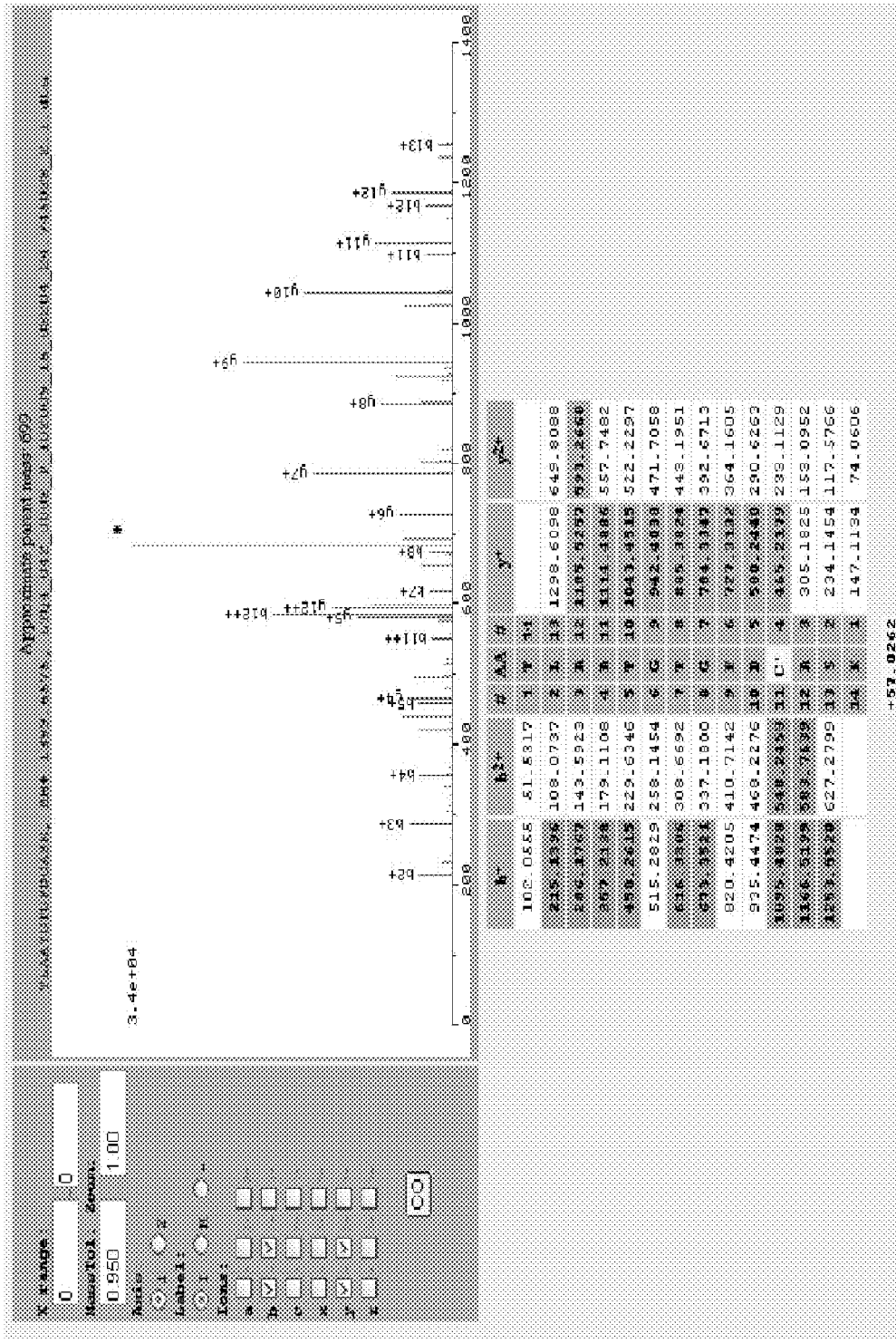
FIG. 1 cont.— gi|IPI00008497.1|sp|P11926|rs|NP_002530| Ornithine decarboxylase|gs|ODC1 LY400909

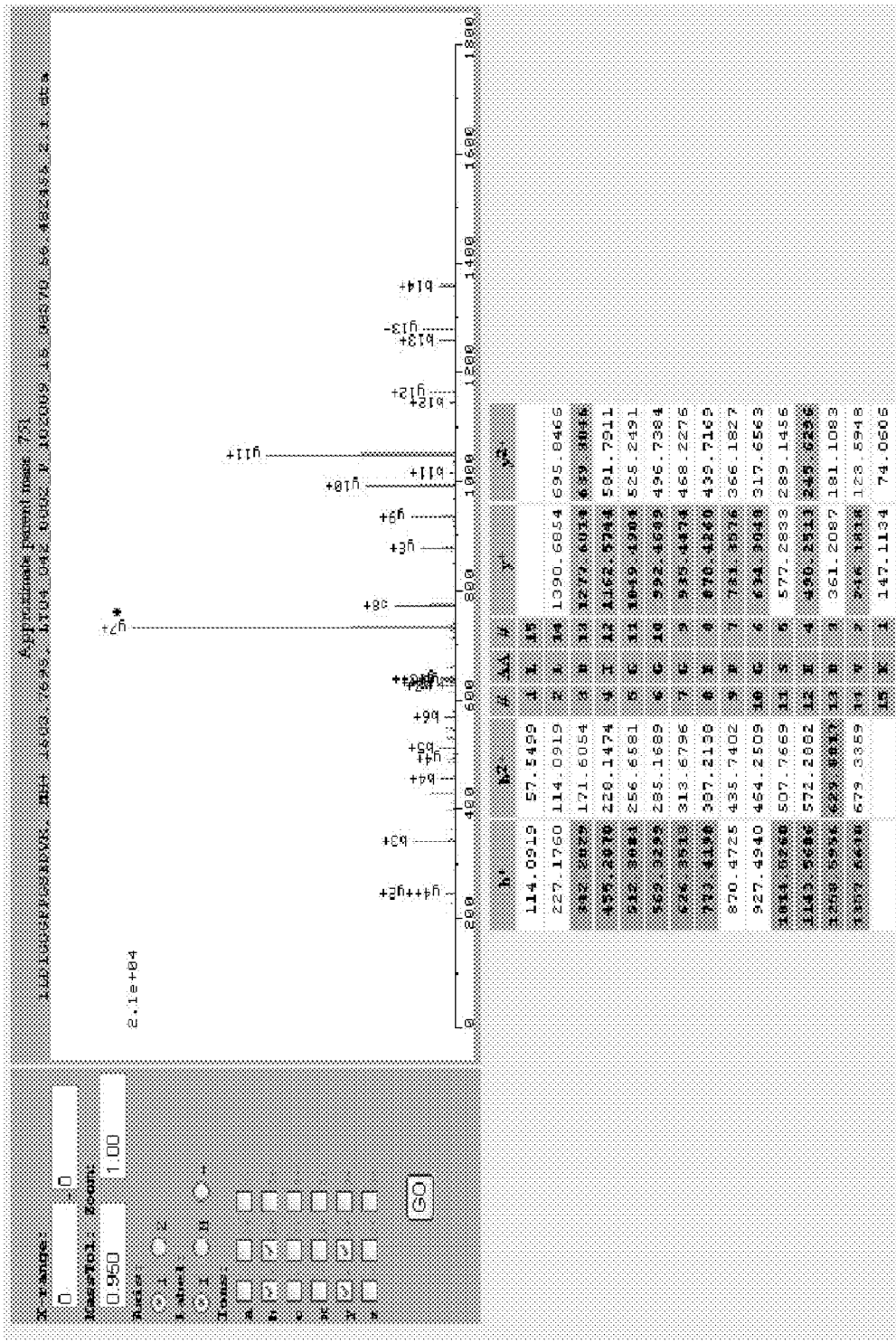
FIG. 1 cont. -- gi|IPI00008497.1|sp|P11926|rs|NP_002530| Ornithine decarboxylase|gs|ODC1 LY400909

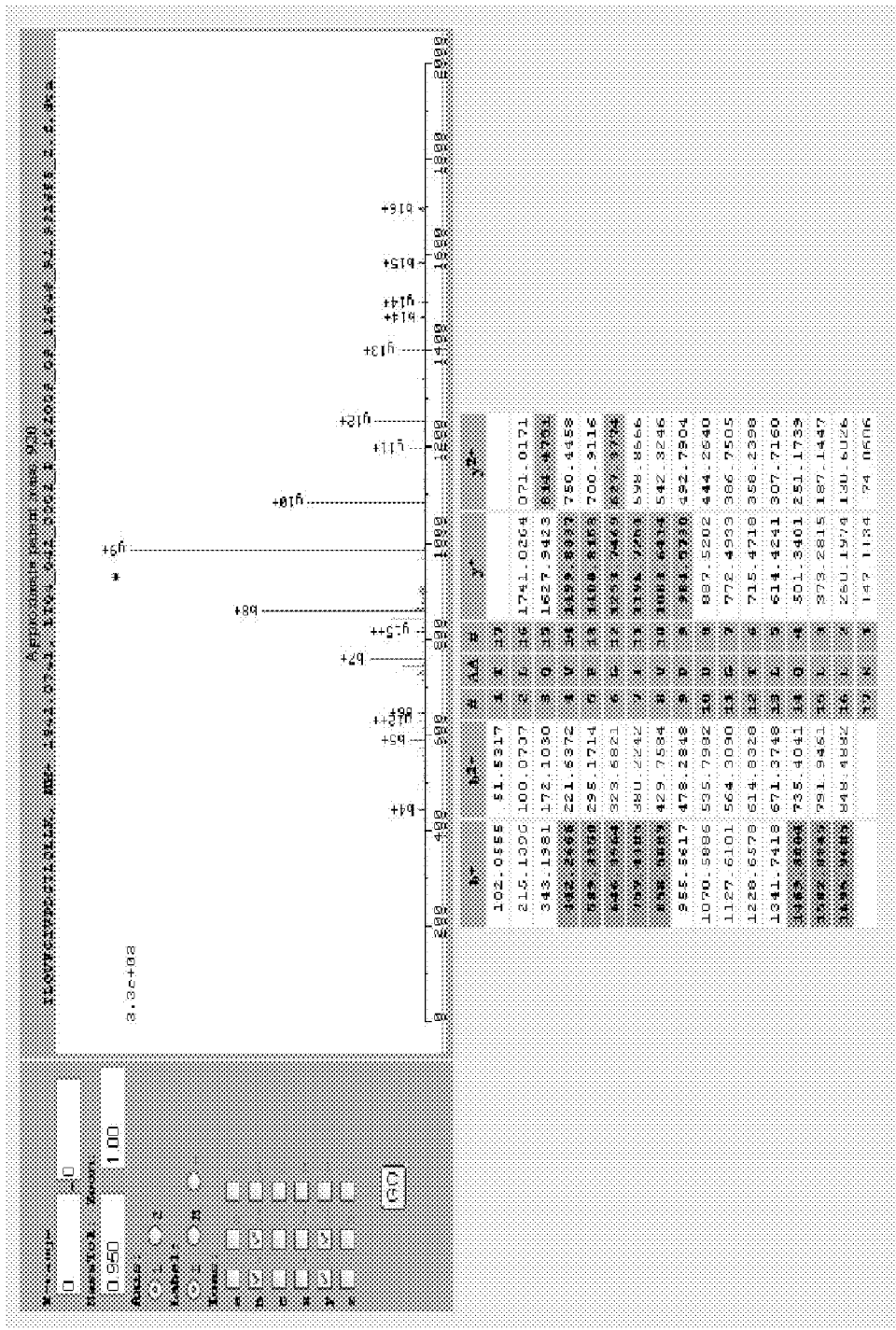
FIG. 1 cont. -- gi|IPI00178899.1|sp|Q13309-1|rs|NP_005974| Isoform 1 of S-phase kinase-associated protein 2|gs|SKP2 LY401815

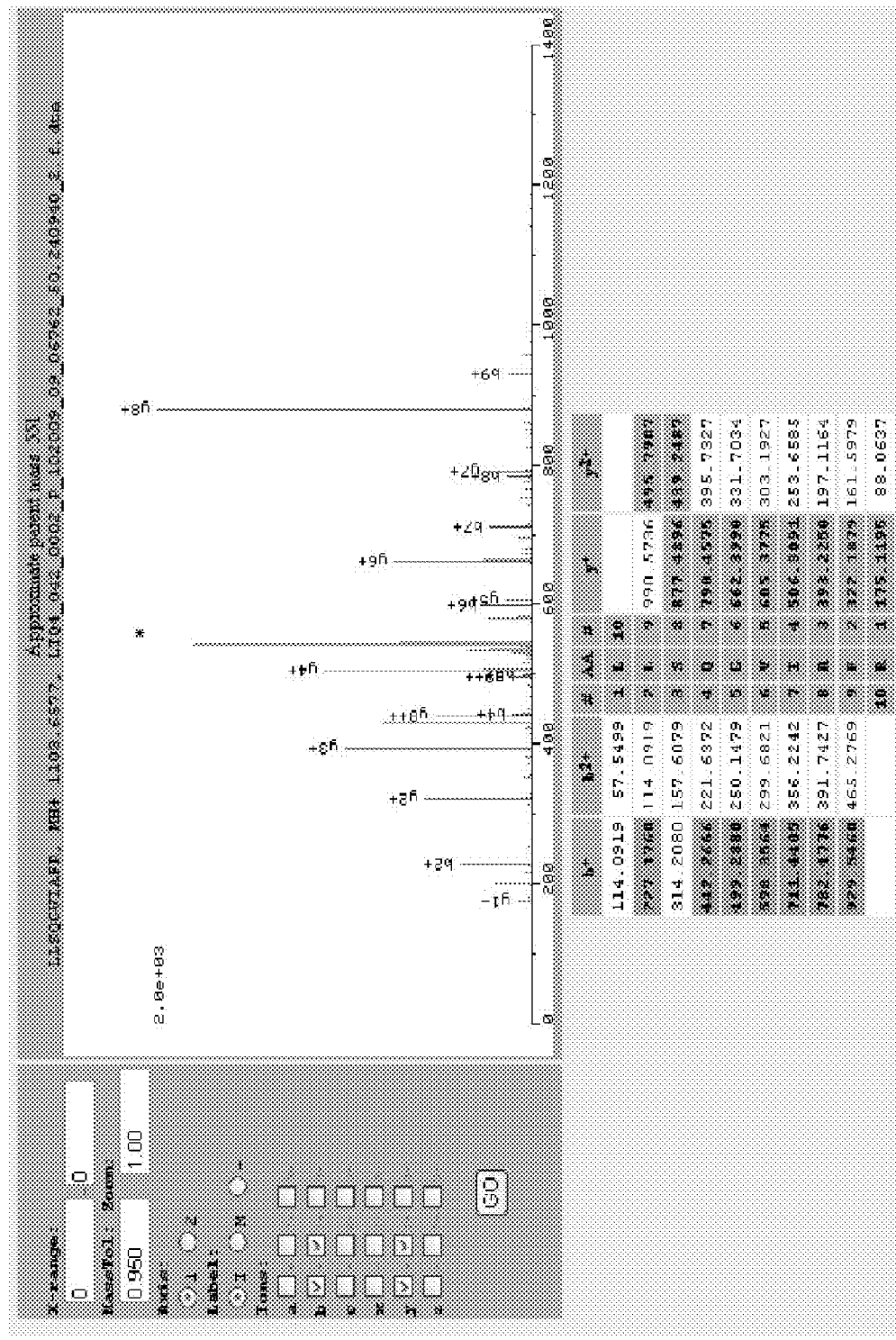
FIG. 1 cont. -- gi|IPI00178899.1|sp|Q13309-1|rs|NP_005974| Isoform 1 of S-phase kinase-associated protein 2|gs|SKP2 LY401815

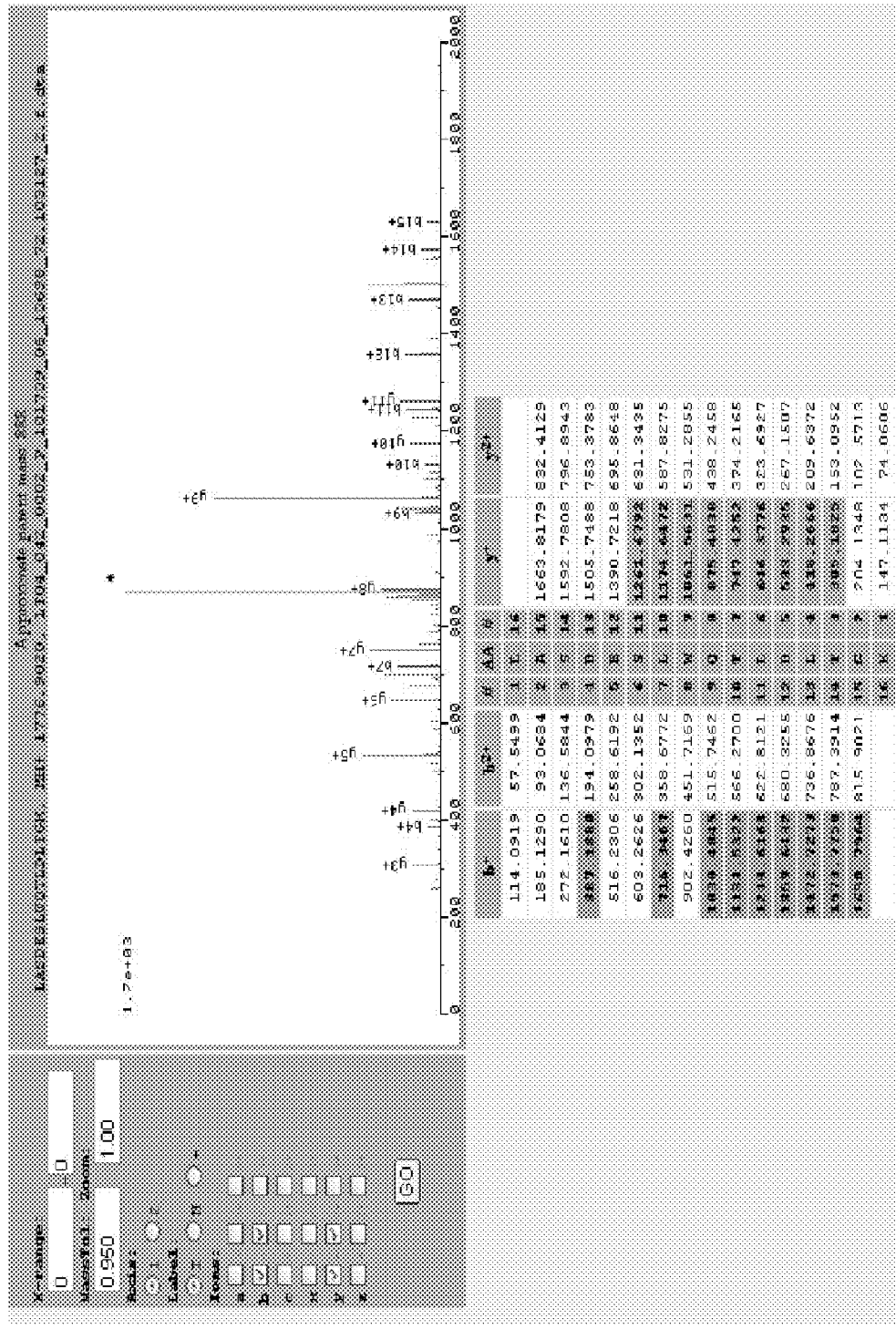
FIG. 1 cont. -- gi|IPI00178899.1|sp|Q13309-1|rs|NP_005974| Isoform 1 of S-phase kinase-associated protein 2|gs|SKP2 LY401815

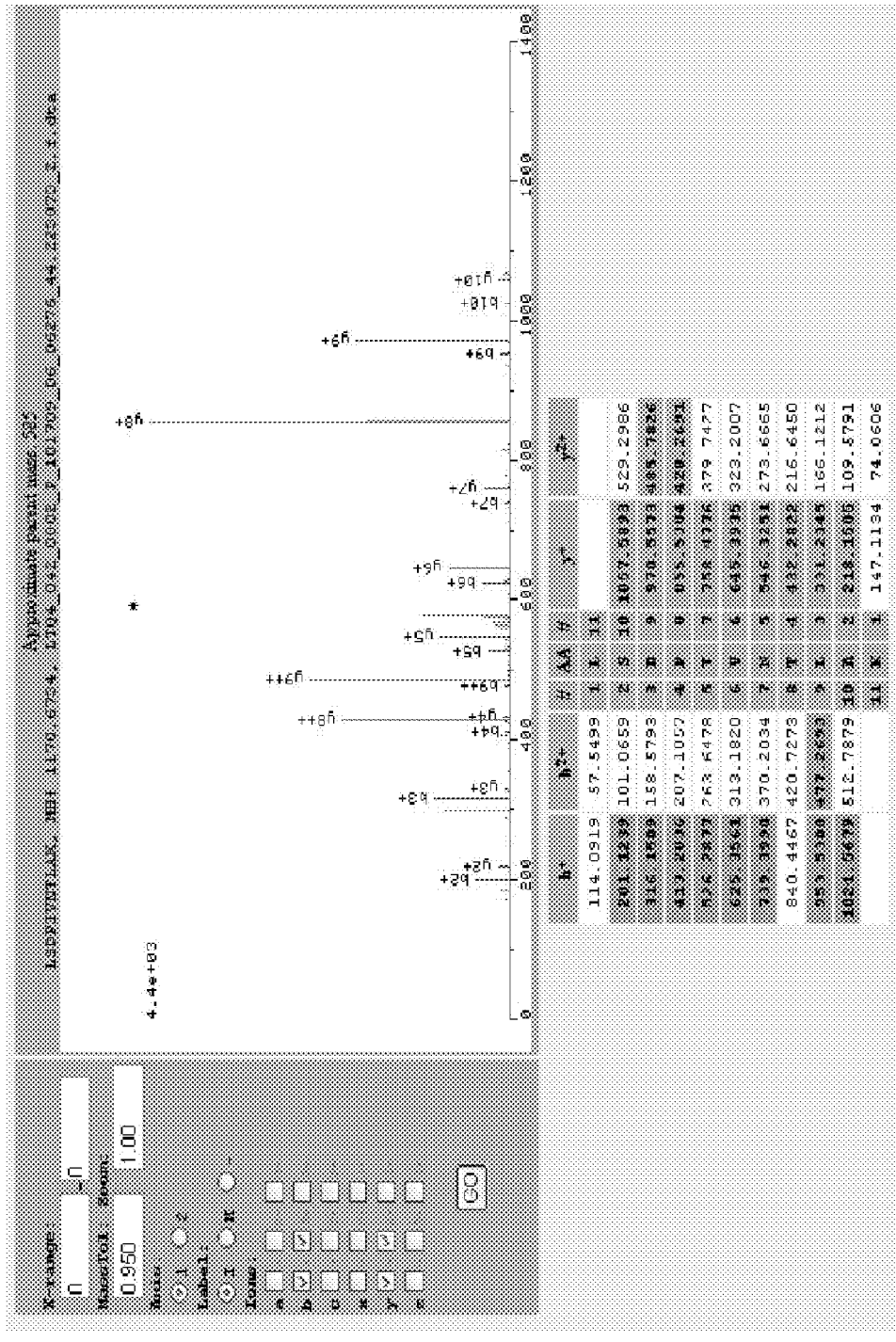
FIG. 1 cont. -- gi|IPI00178899.1|sp|Q13309-1|rs|NP_005974| Isoform 1 of S-phase kinase-associated protein 2|gs|SKP2 LY401815

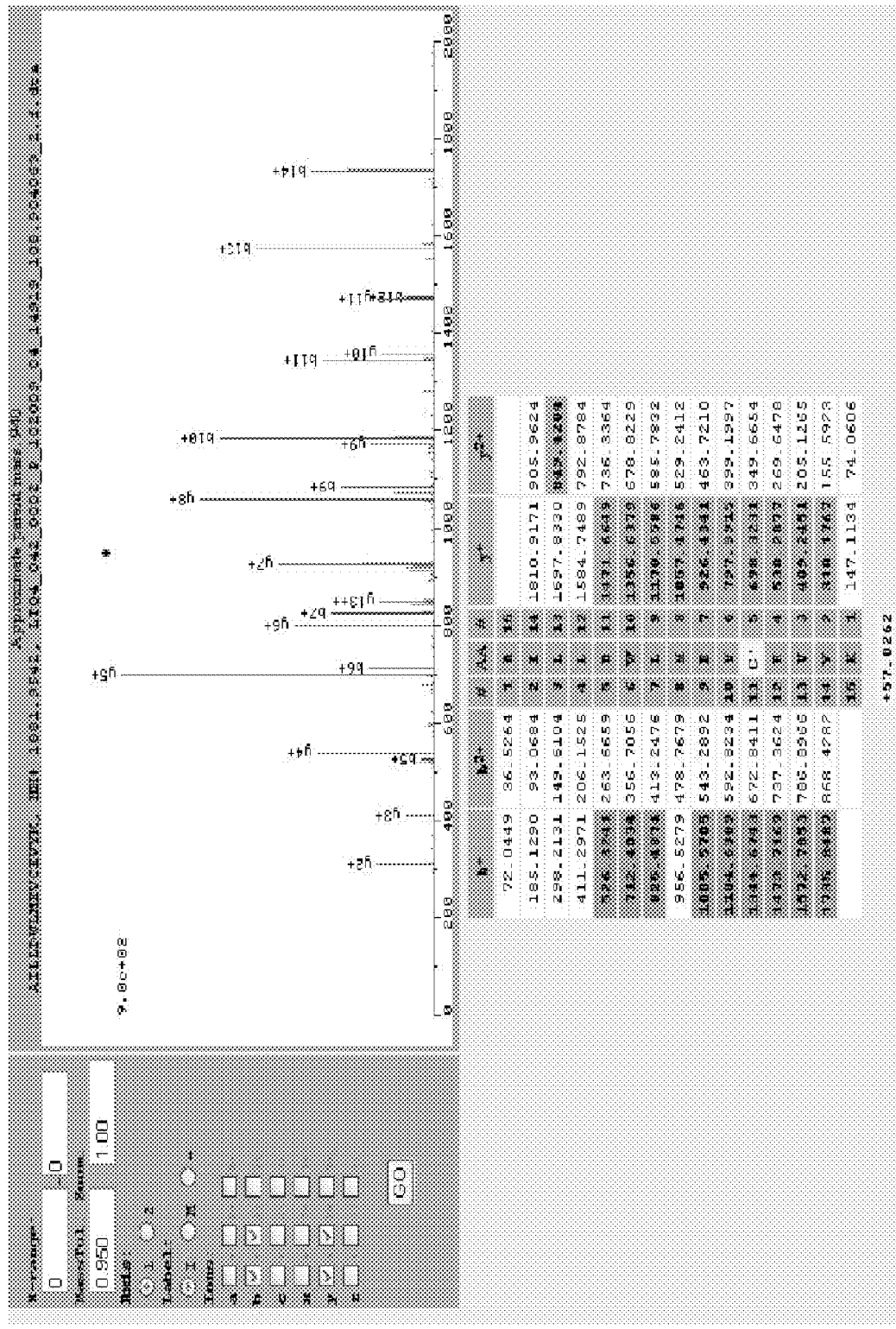
FIG. 1 cont. -- gi|IPI00031077.1|sp|P24864-1|rs|NP_001229| Isoform E1L of G1/S-specific cyclin-E1|gs|CCNE1
LY400495

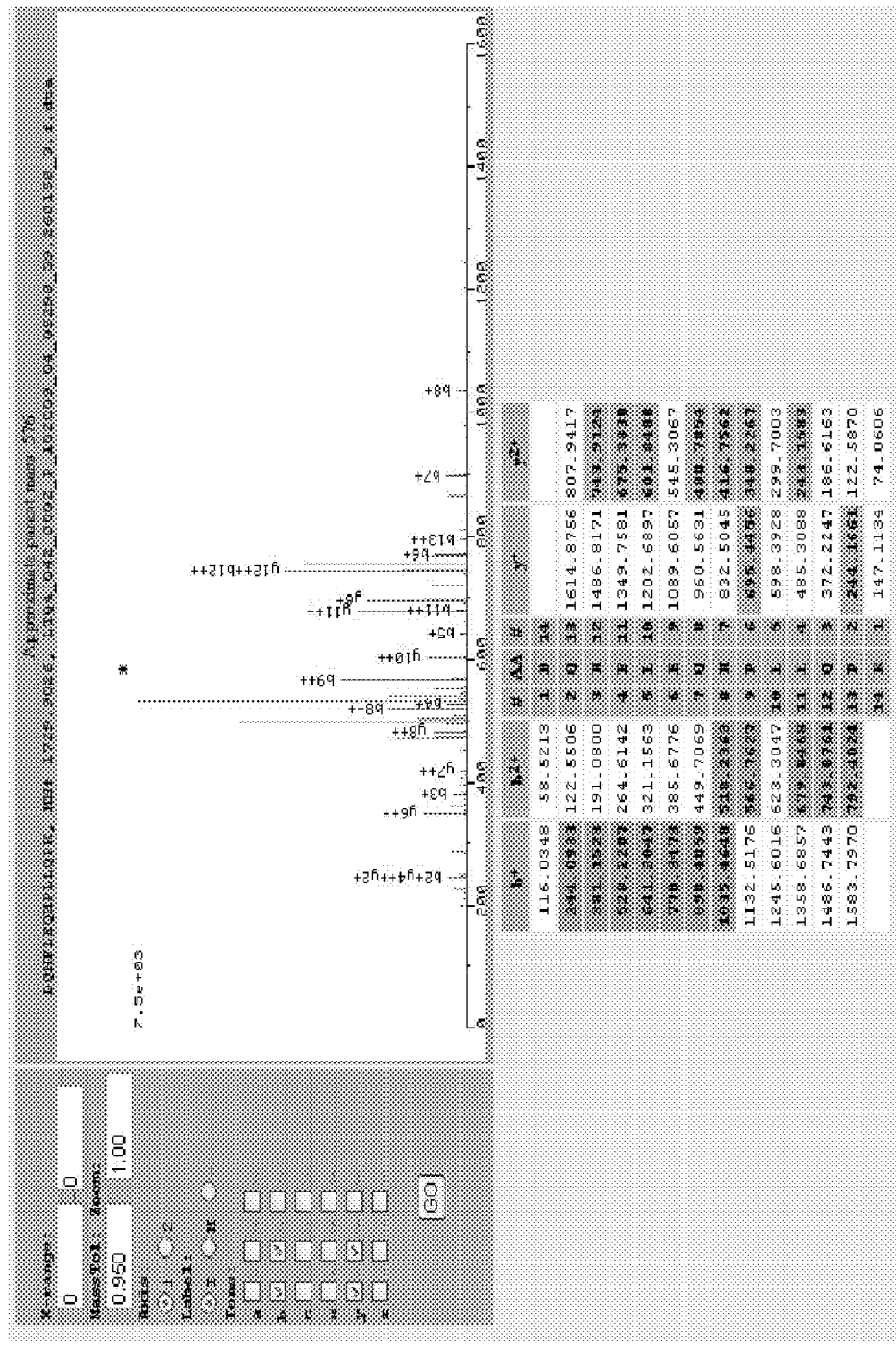
FIG. 1 cont. -- gi|IPI00031077.1|sp|P24864-1|rs|NP_001229| Isoform E1L of G1/S-specific cyclin-E1|gs|CCNE1 LY400495

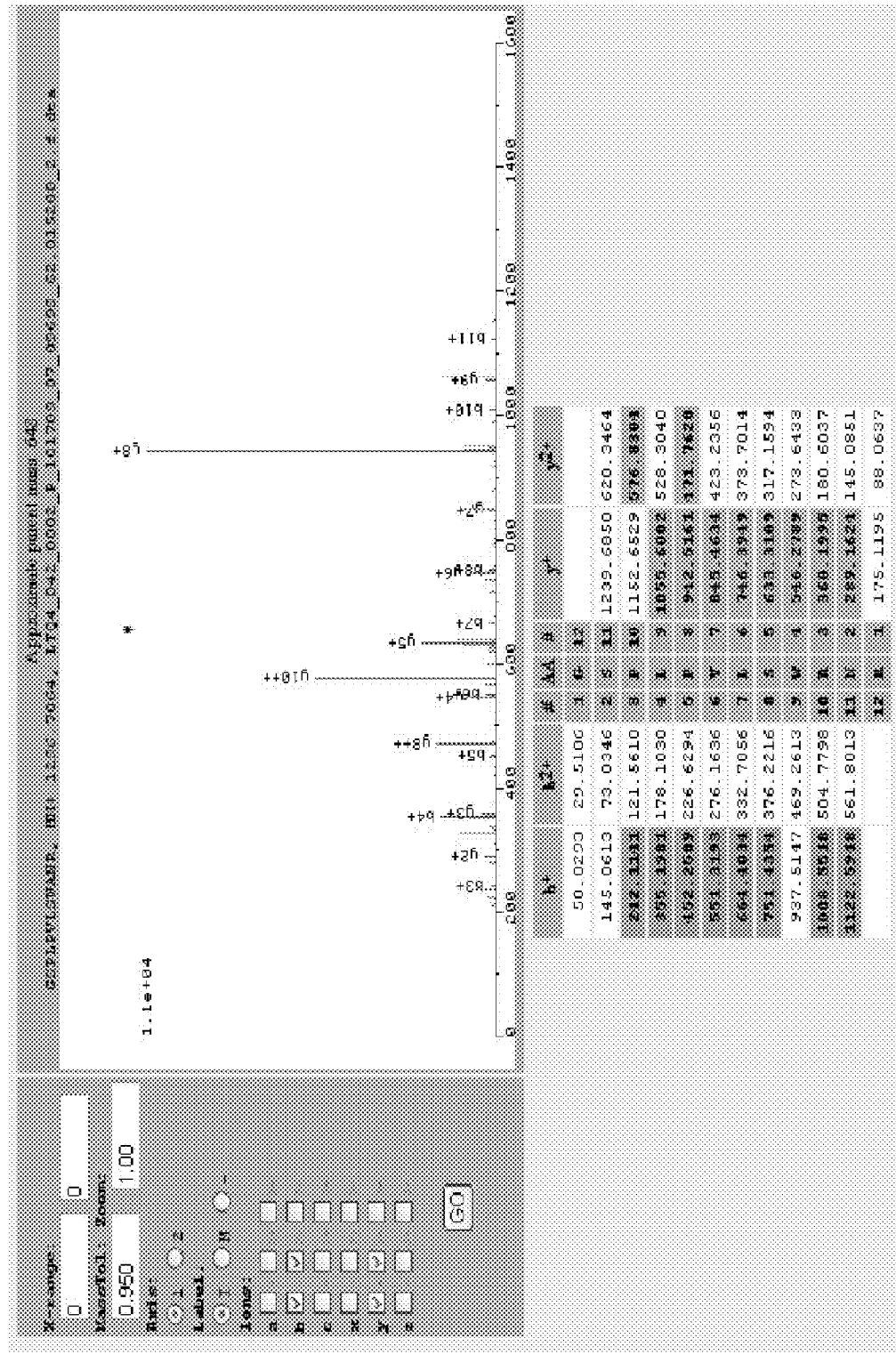
FIG. 1 cont. -- gi|IPI00031077.1|sp|P24864-1|rs|NP_001229| Isoform E1L of G1/S-specific cyclin-E1|gs|CCNE1 LY400495

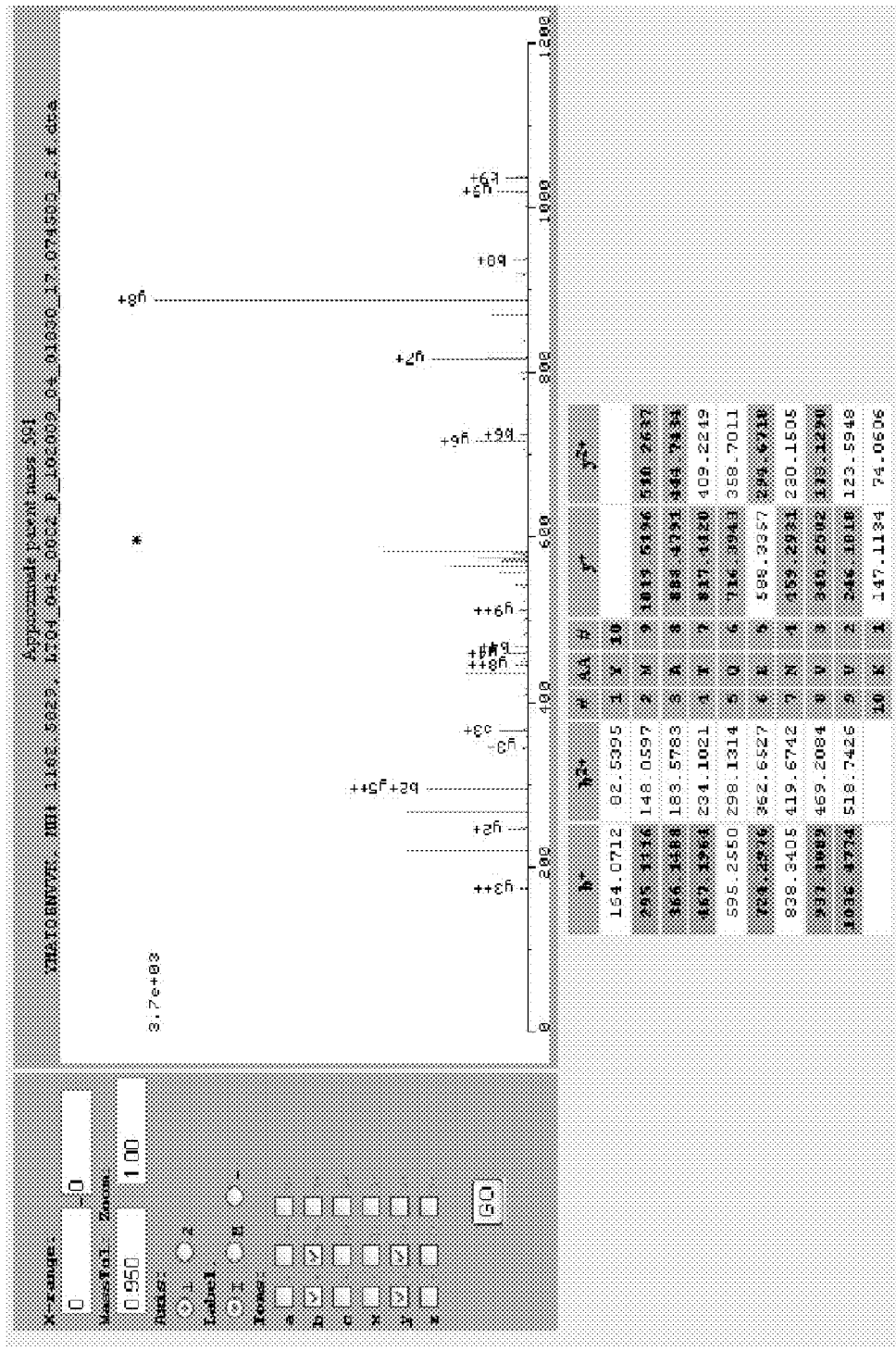
FIG. 1 cont. – gi|IPI00031077.1|sp|P24864-1|rs|NP_001229| Isoform E1L of G1/S-specific cyclin-E1|gs|CCNE1 LY400495

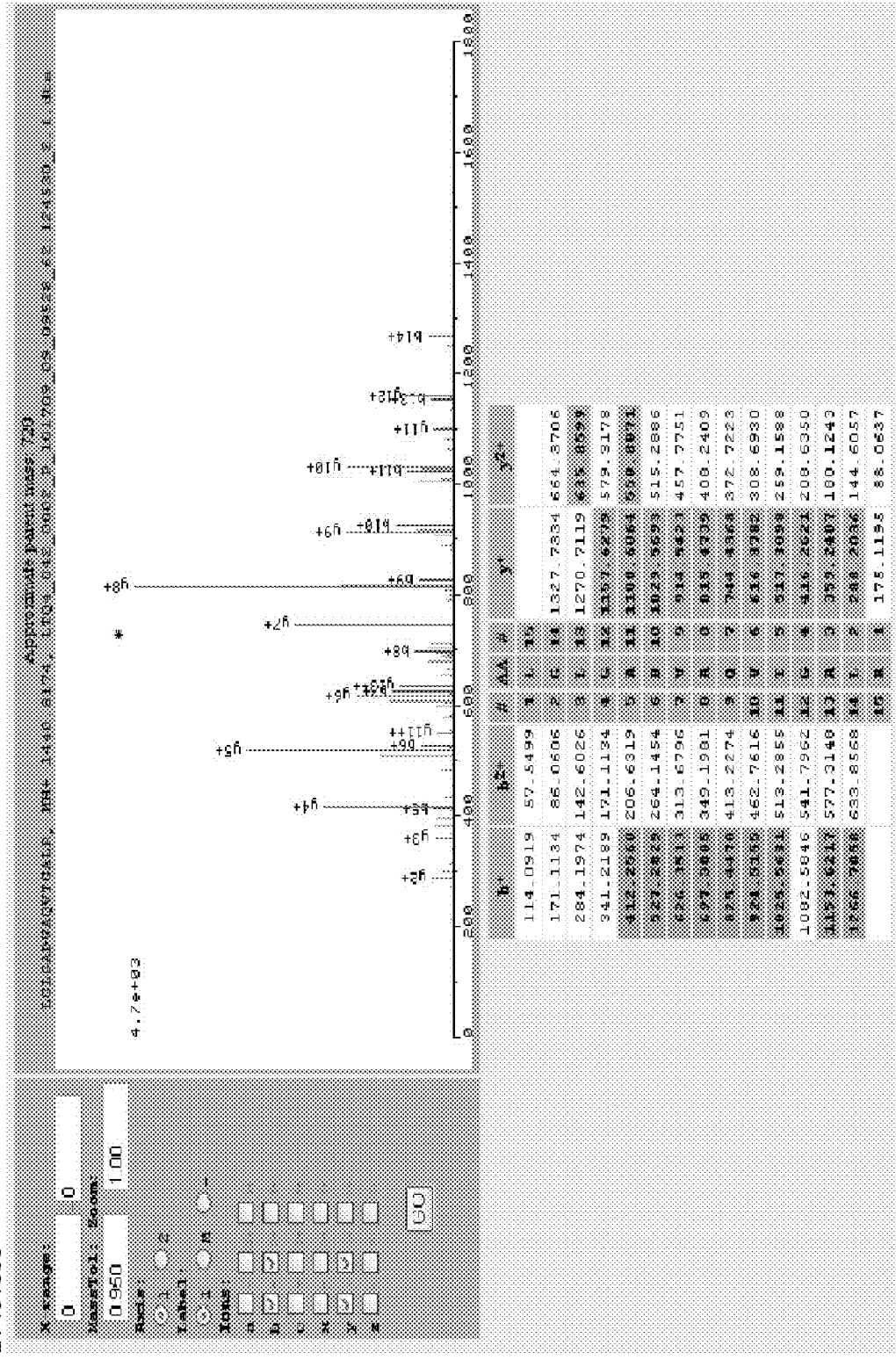
FIG. 1 cont. -- gi|IPI00027509.4|sp|P14780|rs|NP_004985| Matrix metalloproteinase-9|gs|MMP9
LY401553

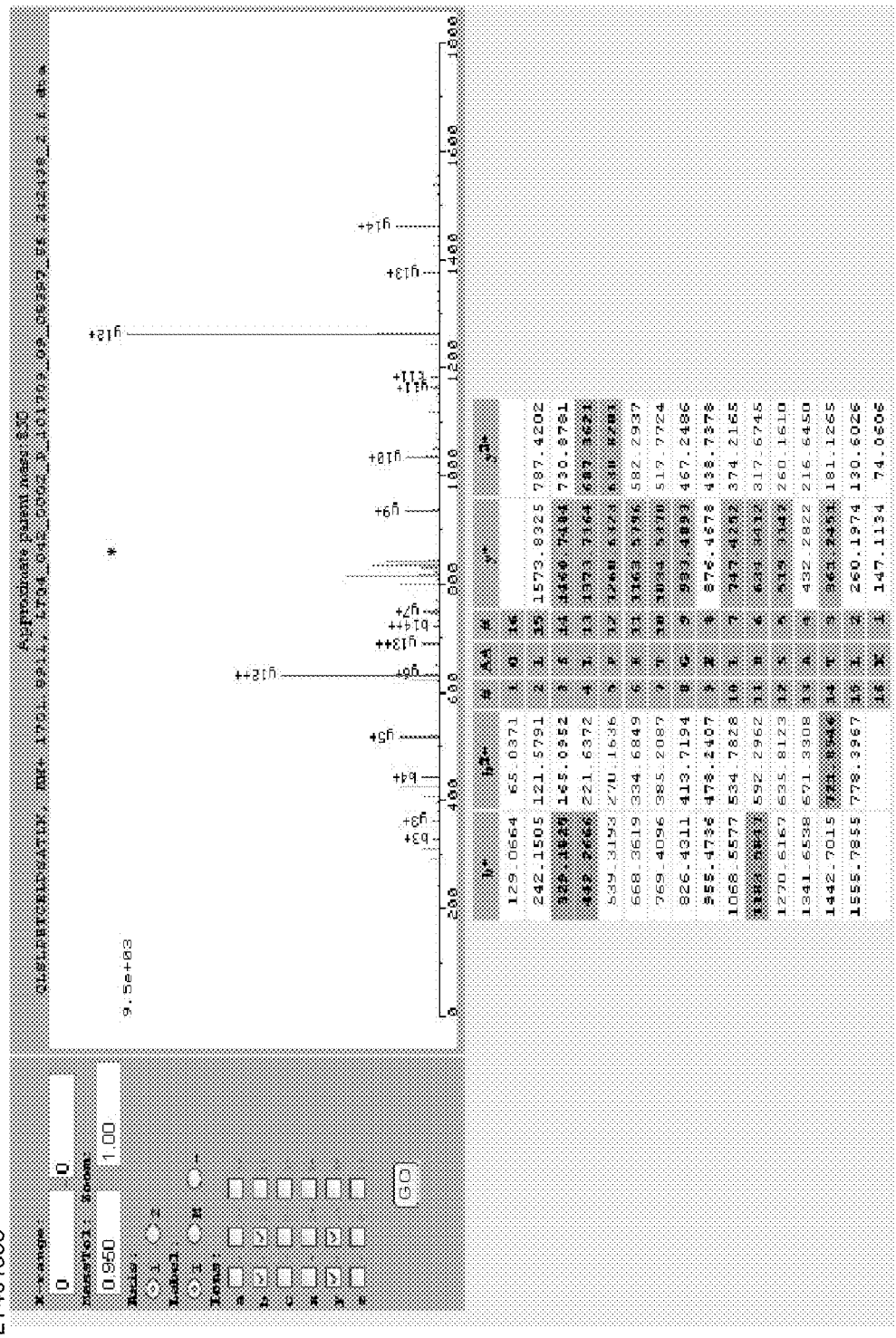
FIG. 1 cont. -- gi|IPI00027509.4|sp|P14780|rs|NP_004985| Matrix metalloproteinase-9|gs|MMP9 LY401553

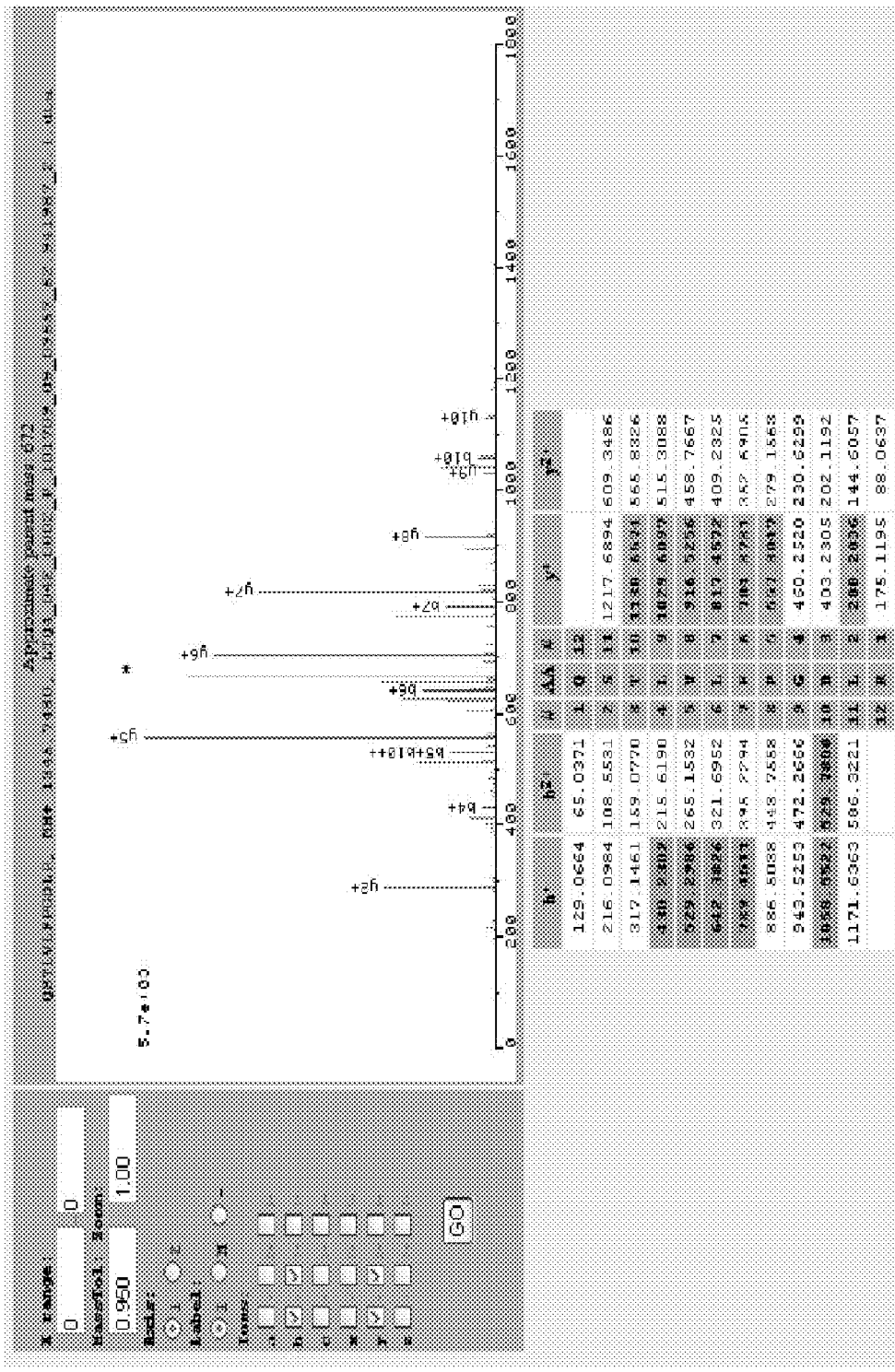
FIG. 1 cont. -- gi||IPI00027509.4|sp|P14780|rs|NP_004985] Matrix metalloproteinase-9|gs|MMP9
LY401553

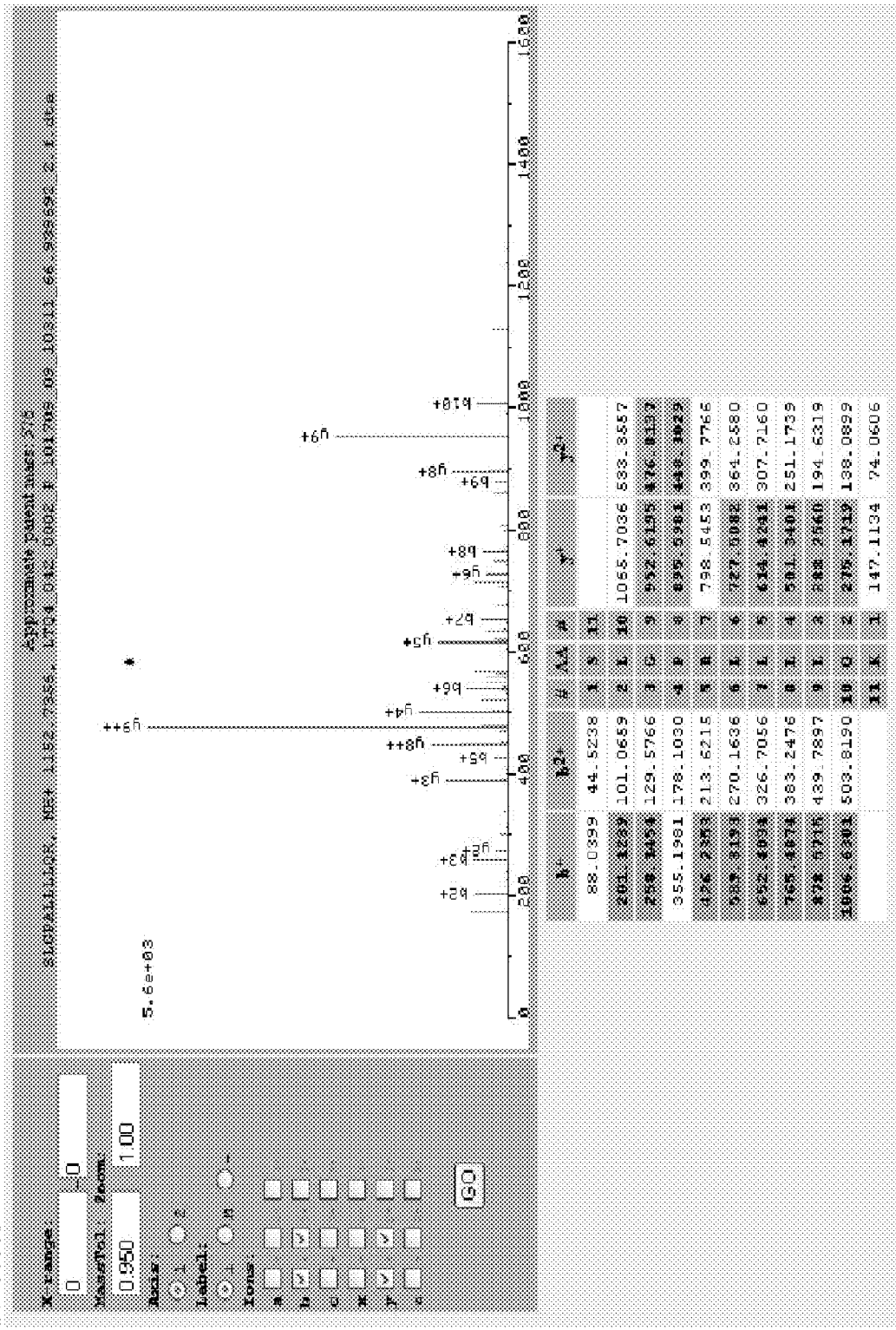
FIG. 1 cont. -- gi||PIO0027509.4|sp|P14780|rs|NP_004985| Matrix metalloproteinase-9|gs|MMP9 LY401553

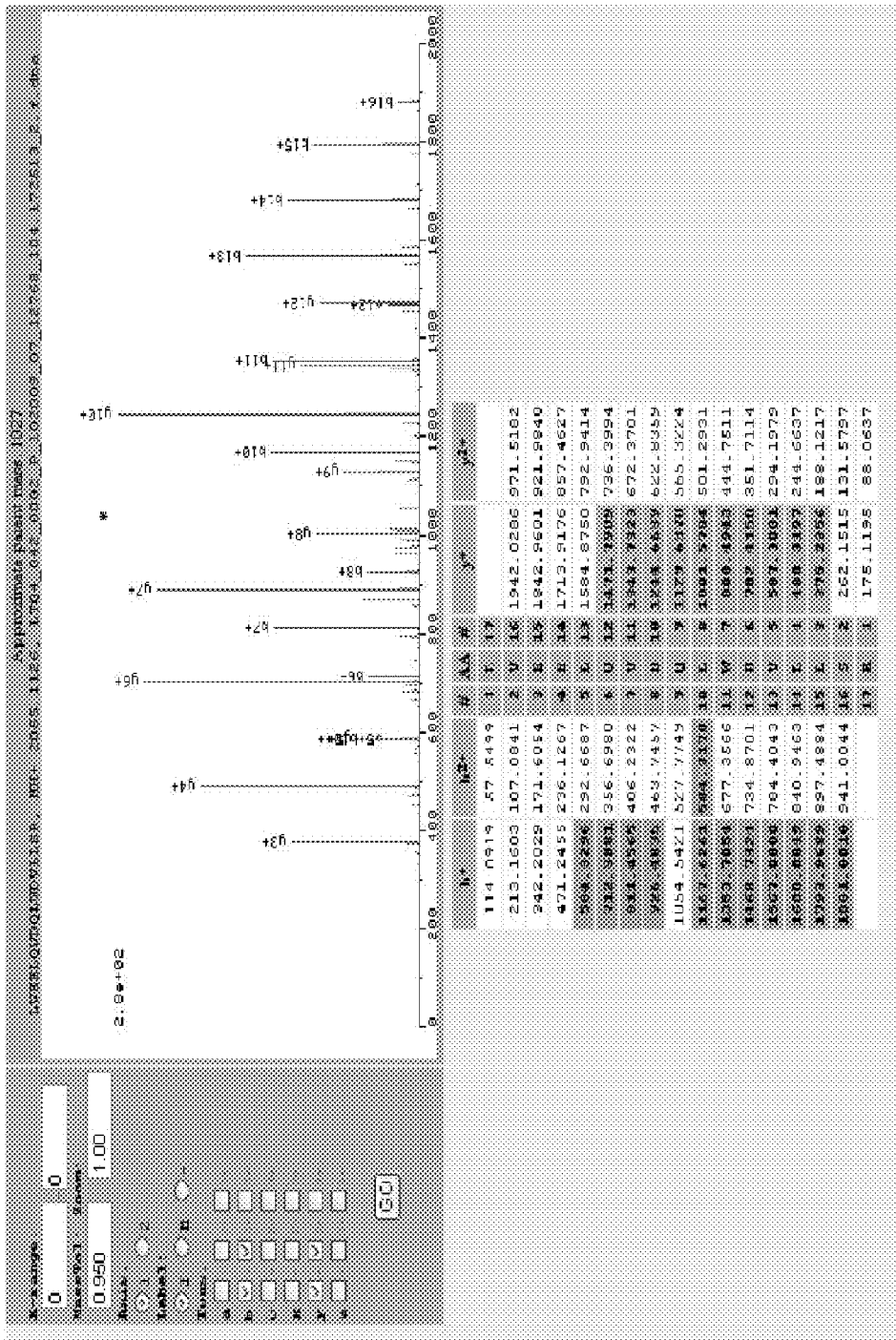
FIG. 1 cont. – gi|g ||IPI00216934.1|sp|P55211-2|rs|NP_127463| Isoform 2 of Caspase-9|gs|CASP9 LY409796

FIG. 1 cont. -- gi|g |IPI00216934.1|sp|P55211-2|rs|NP_127463| Isoform 2 of Caspase-9|gs|CASP9
LY409796
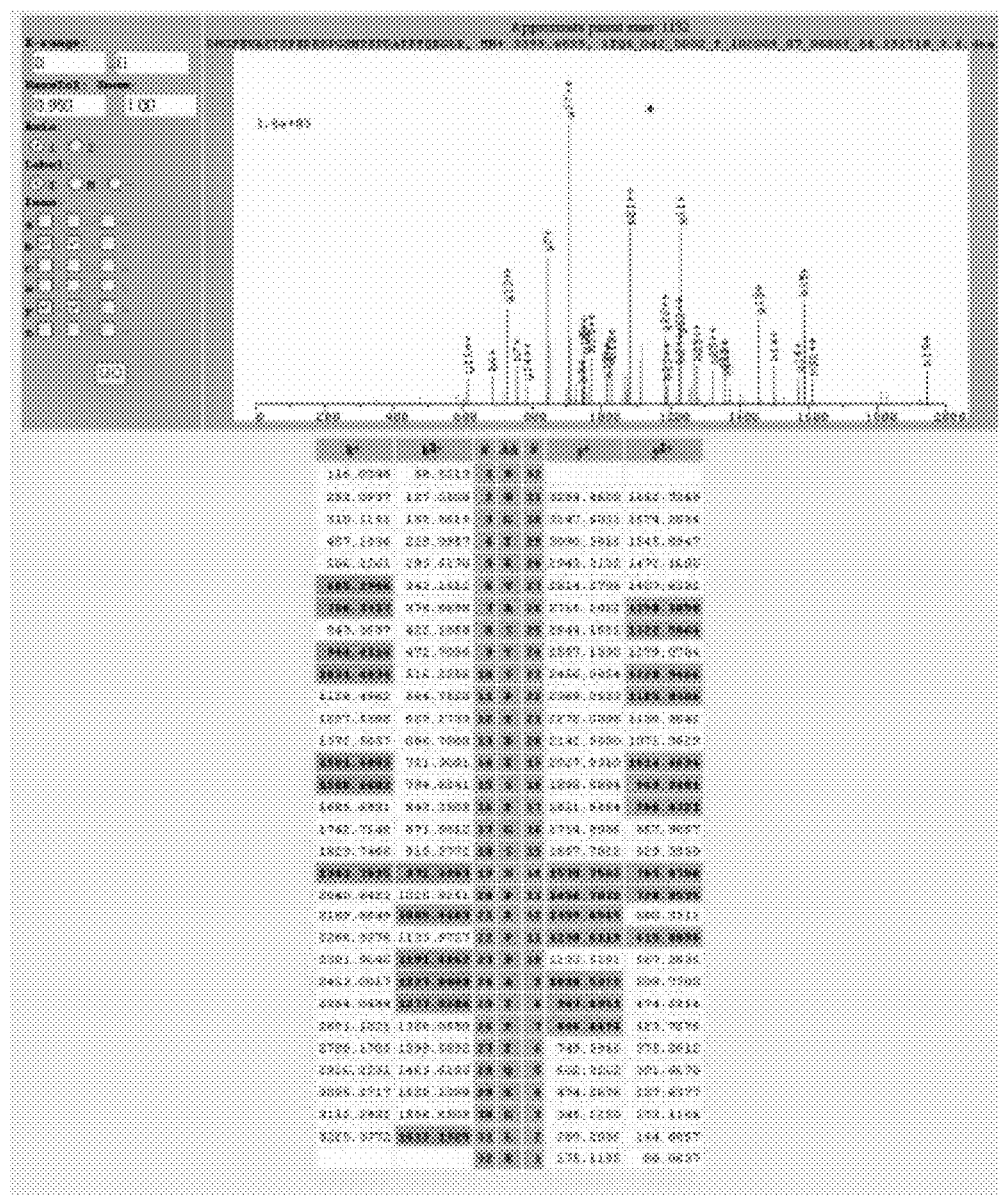

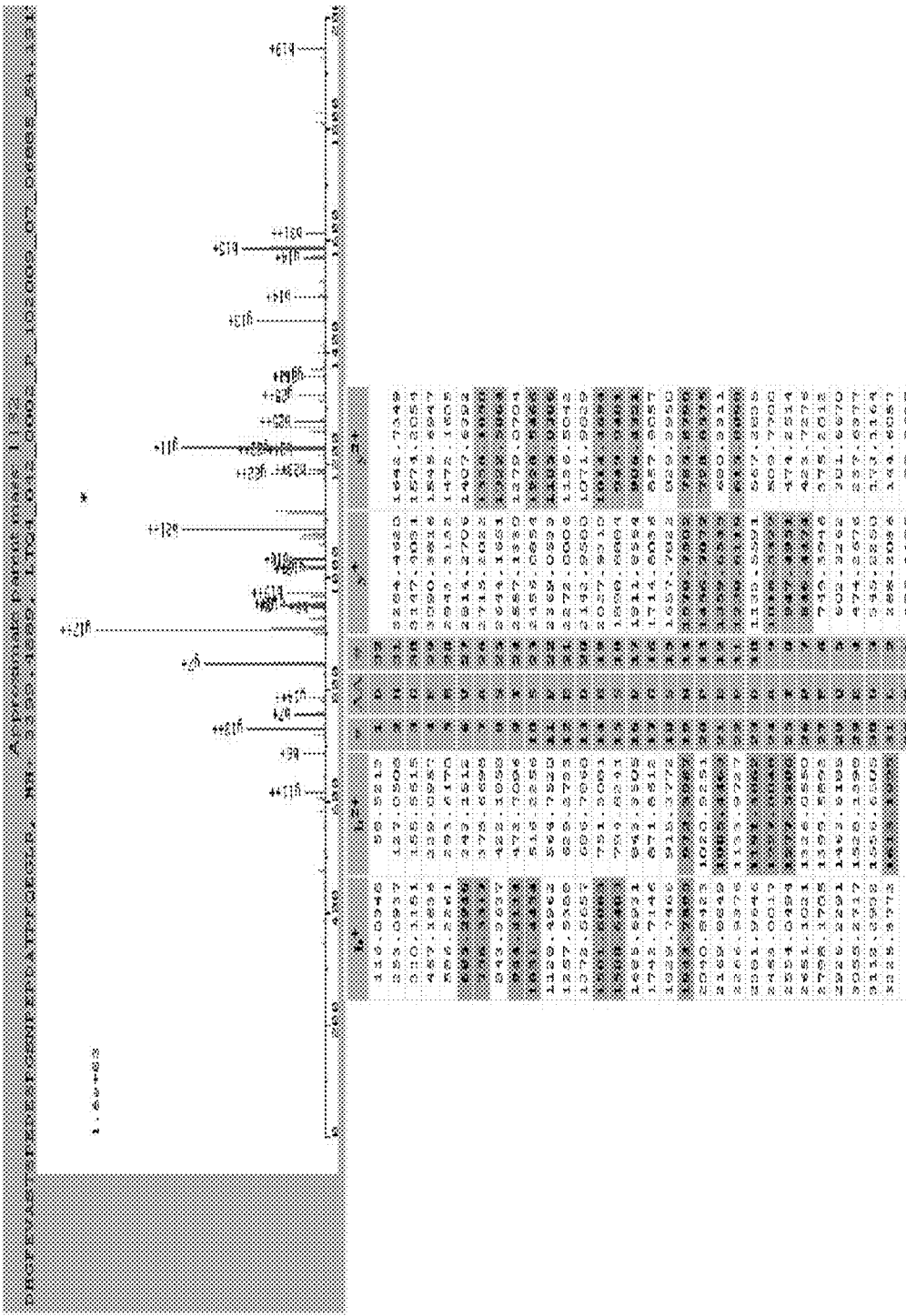
FIG. 1 cont. -- DHGFEVASTSPEDESPGSNPEPDATPFQEGLR, MH+ 3399.4889

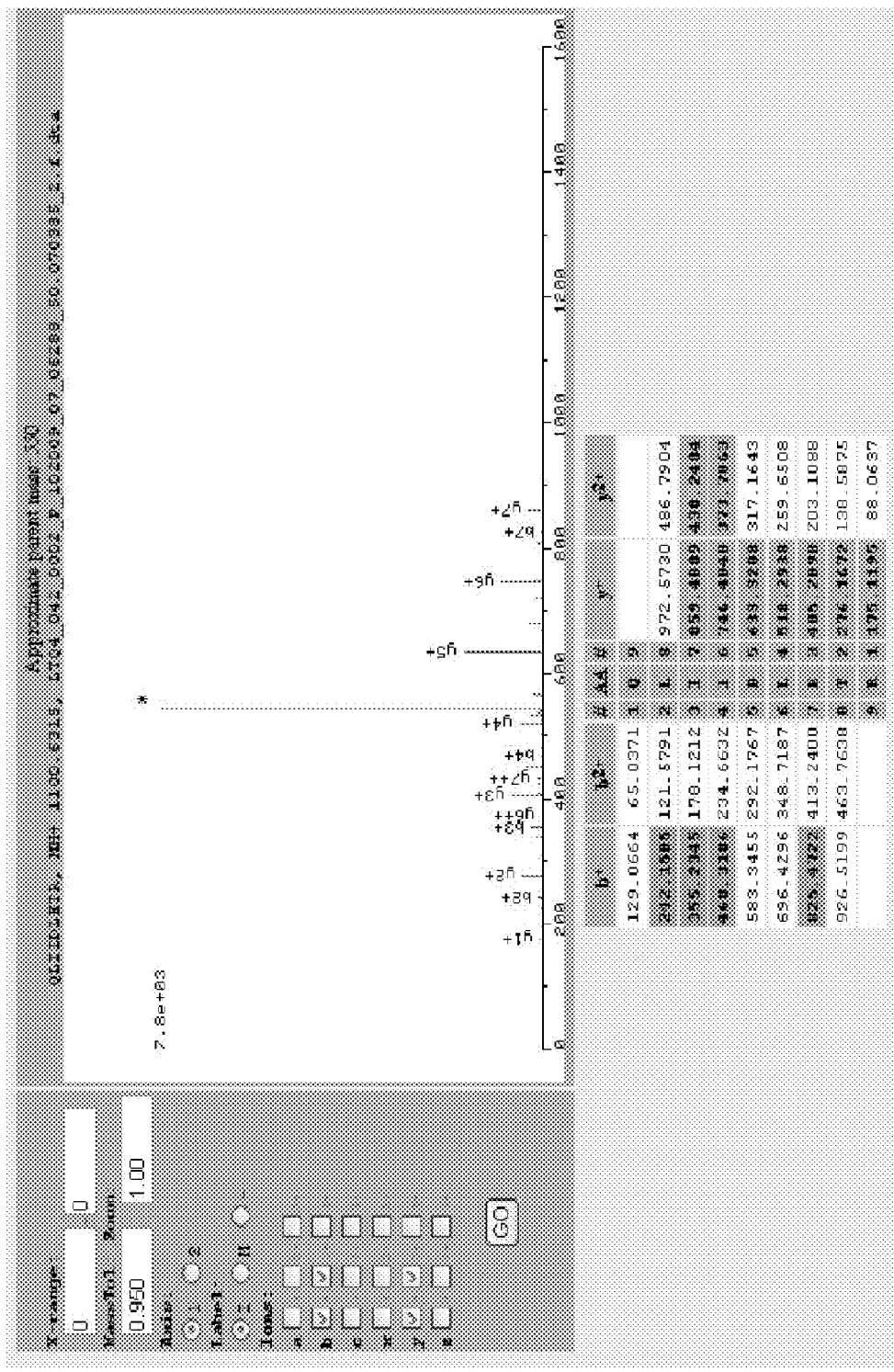
FIG. 1 cont. -- gi|g ||PI00216934.1|sp|P55211-2|rs|NP_127463| Isoform 2 of Caspase-9|gs|CASP9
LY409796

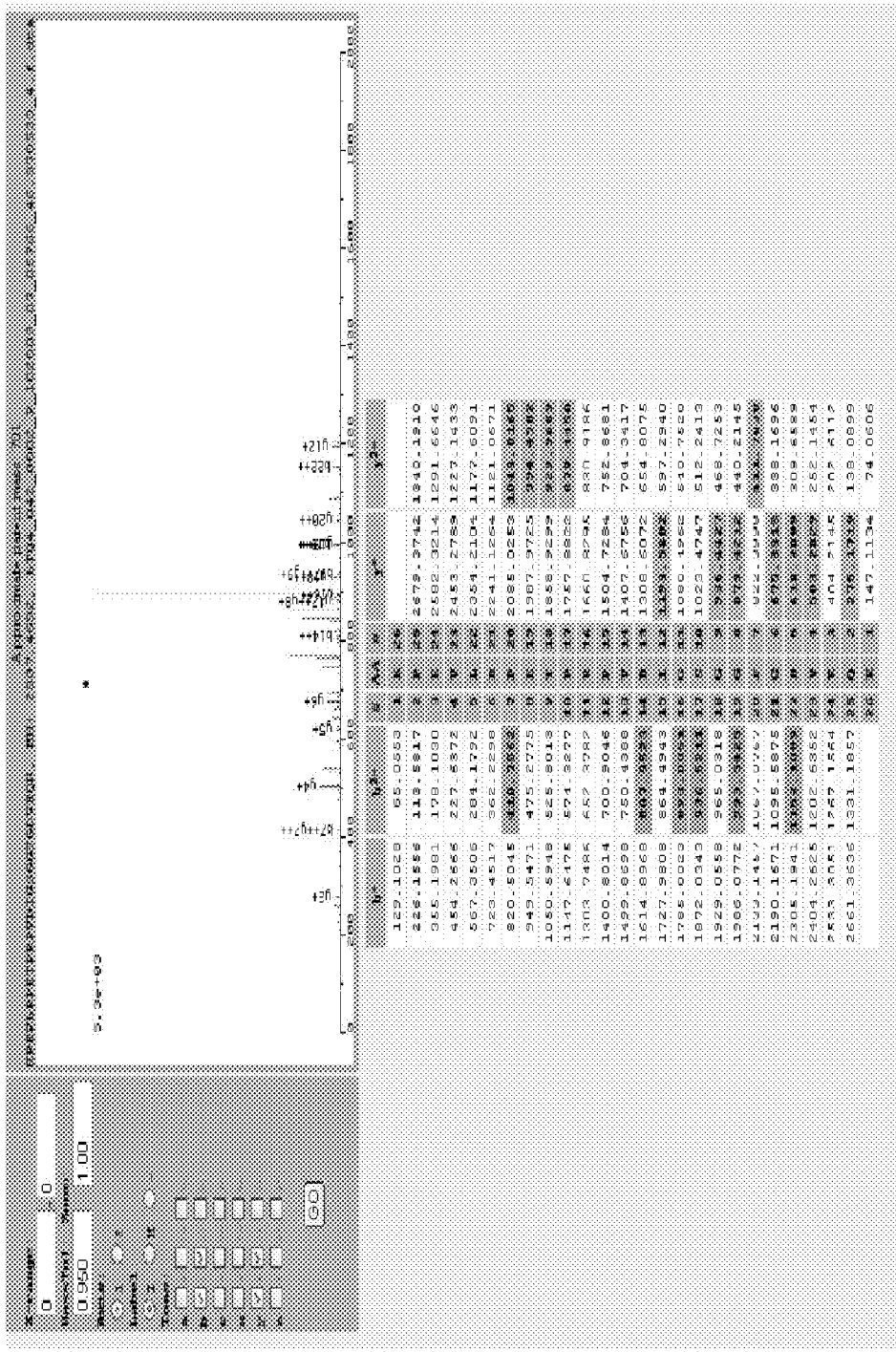
FIG. 1 cont. -- gi|g |IPI00216934.1|sp|P55211-2|rs|NP_127463| Isoform 2 of Caspase-9|gs|CASP9 LY409796

FIG. 1 cont. -- gi|IPI00019983.1|sp|Q07817-1|rs|NP_612815| Isoform Bcl-X(L) of Bcl-2-like protein 1|gs|BCL2L1
LY403363
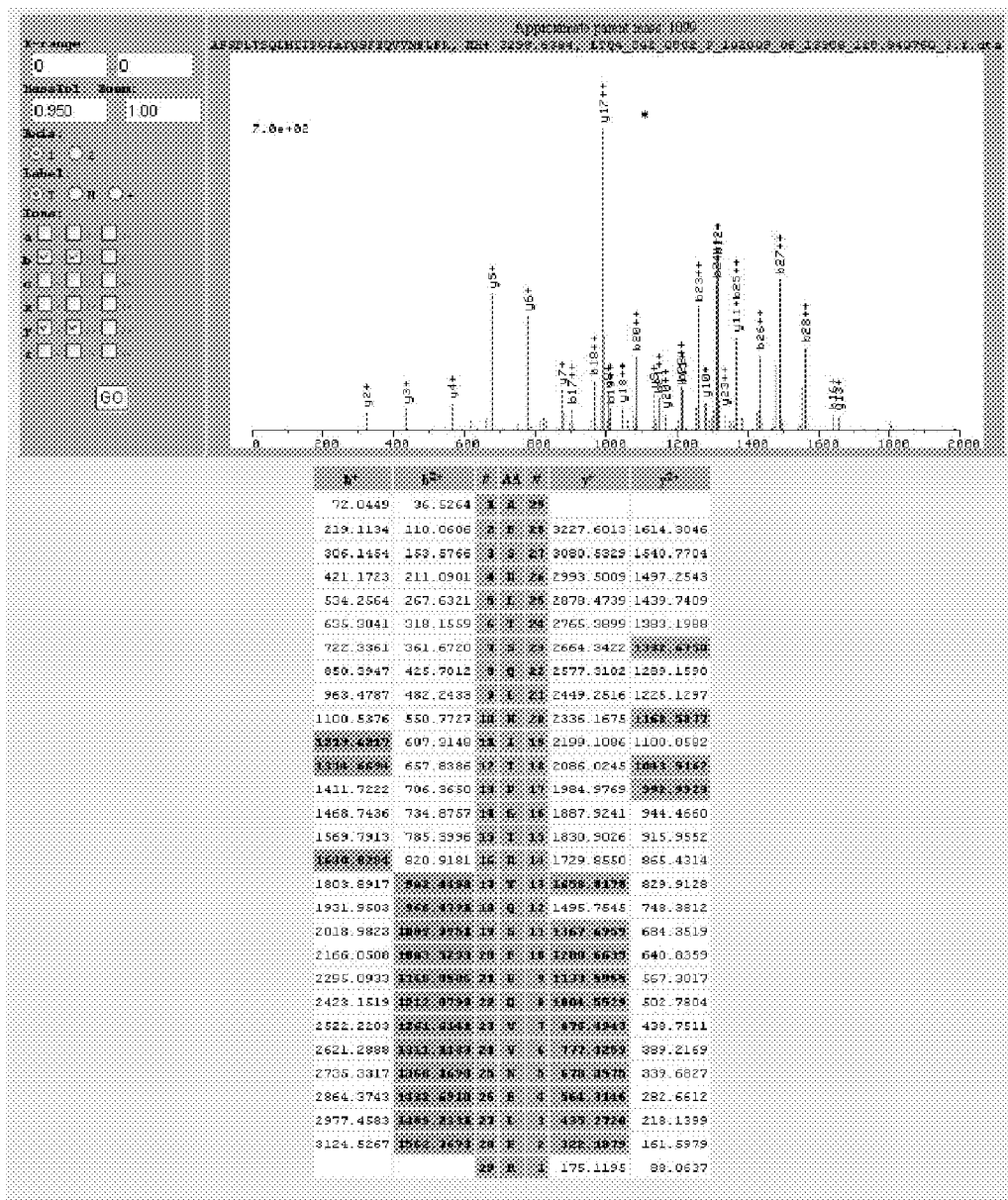

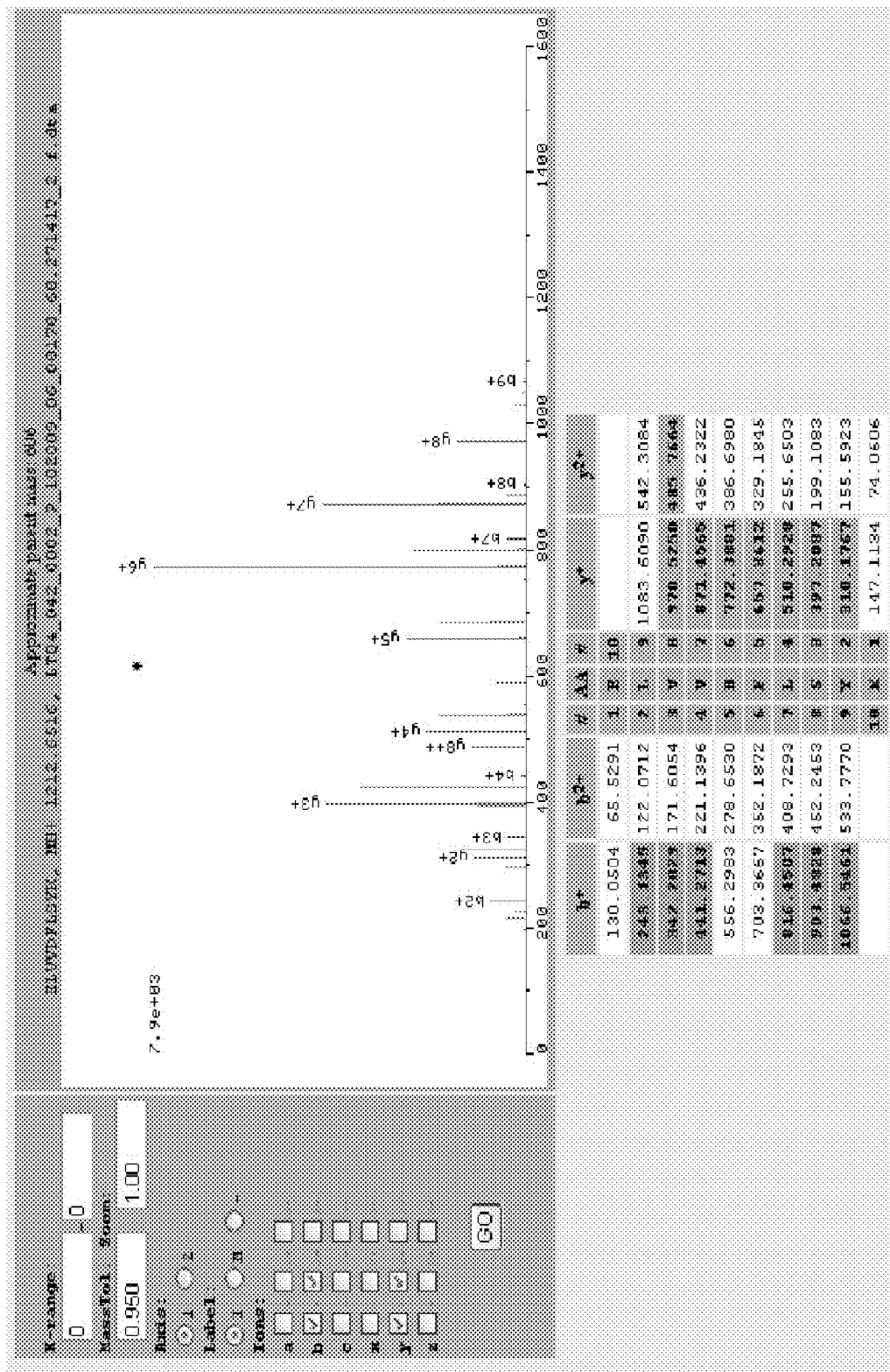
FIG. 1 cont. -- gi|IPI00019983.1|sp|Q07817-1|rs|NP_612815| Isoform Bcl-X(L) of Bcl-2-like protein 1|gs|BCL2L1
LY403363

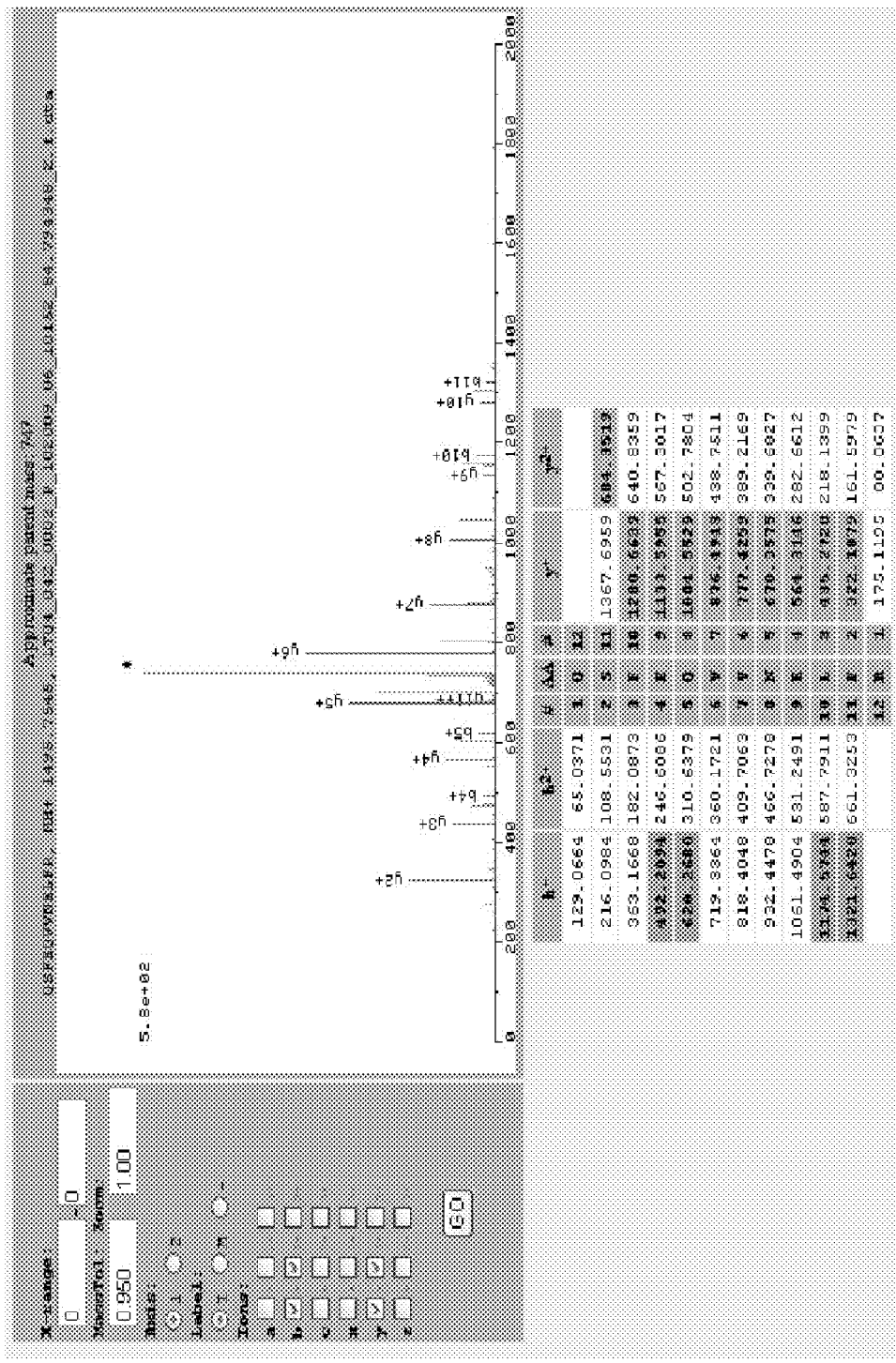
FIG. 1 cont. -- gi|IPI00019983.1|sp|Q07817-1|rs|NP_612815| Isoform Bcl-X(L) of Bcl-2-like protein 1|gs|BCL2L1 LY403363

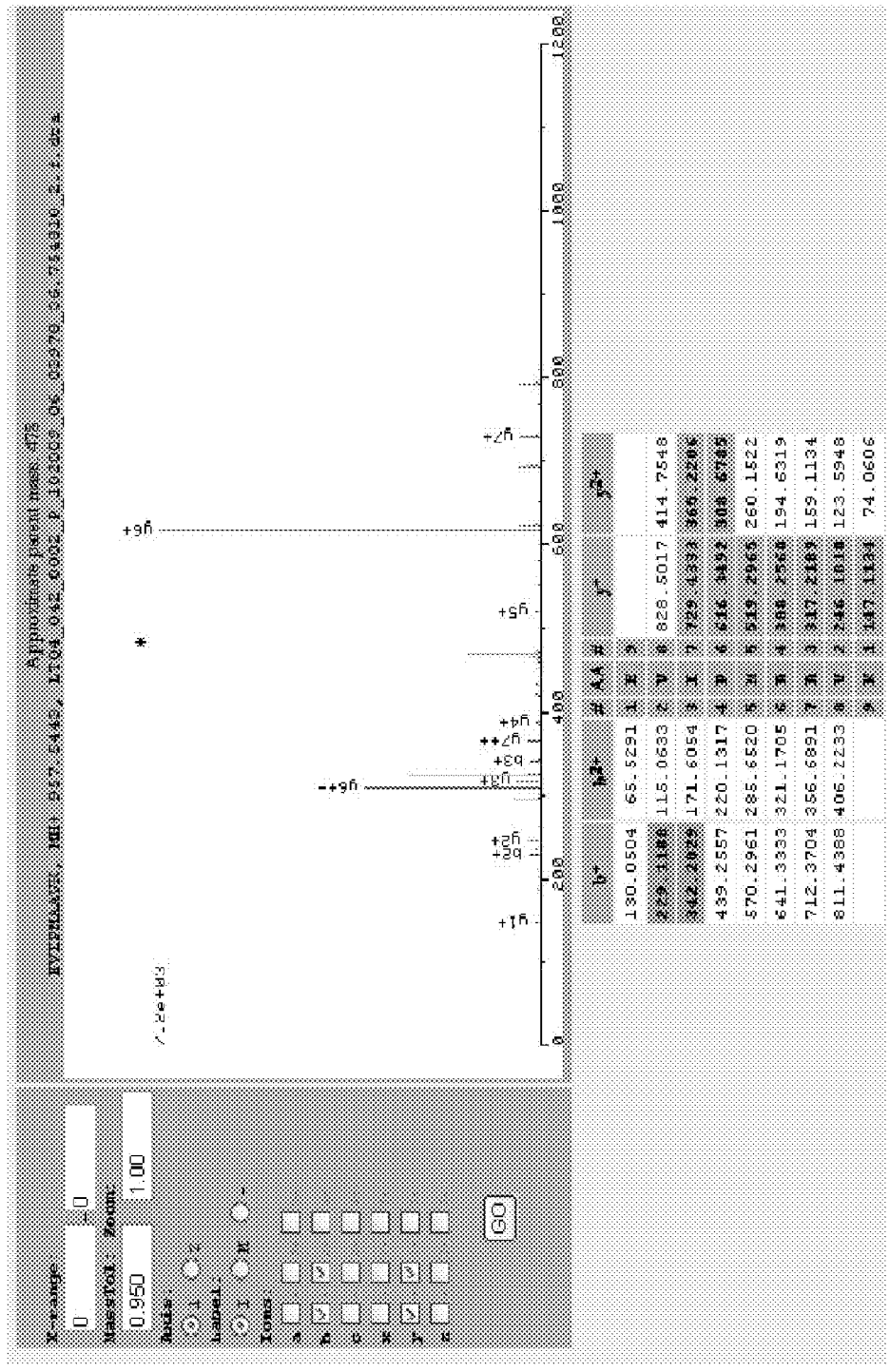
FIG. 1 cont. -- gi|IPI00019983.1|sp|Q07817-1|rs|NP_612815| Isoform Bcl-X(L) of Bcl-2-like protein 1|gs|BCL2L1 LY403363

FIG. 1 cont. -- gi|IPI00002569.3|sp|Q13541|rs|NP_004086| Eukaryotic translation initiation factor 4E-binding protein 1|gs|EIF4EBP1
LY401322
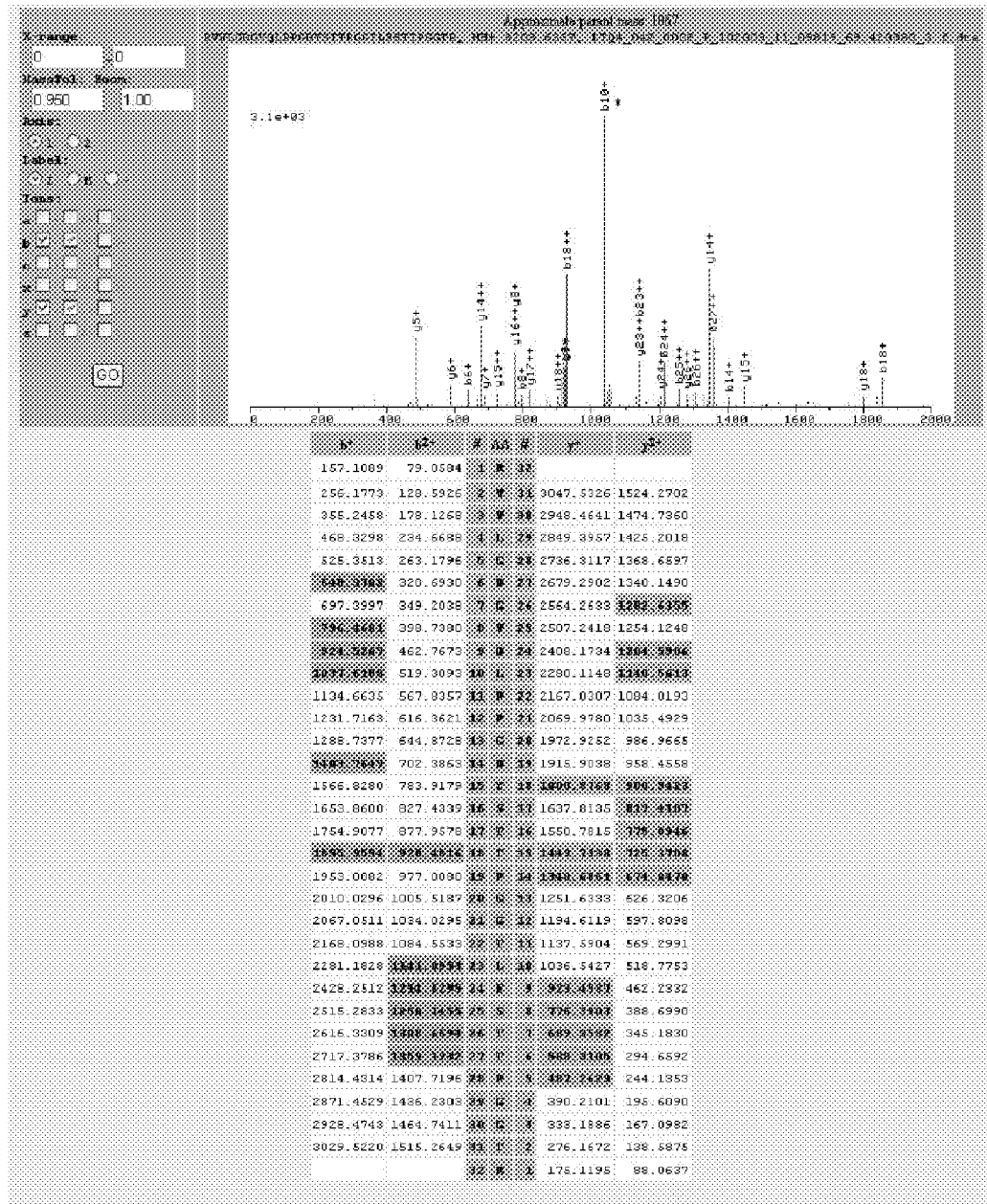

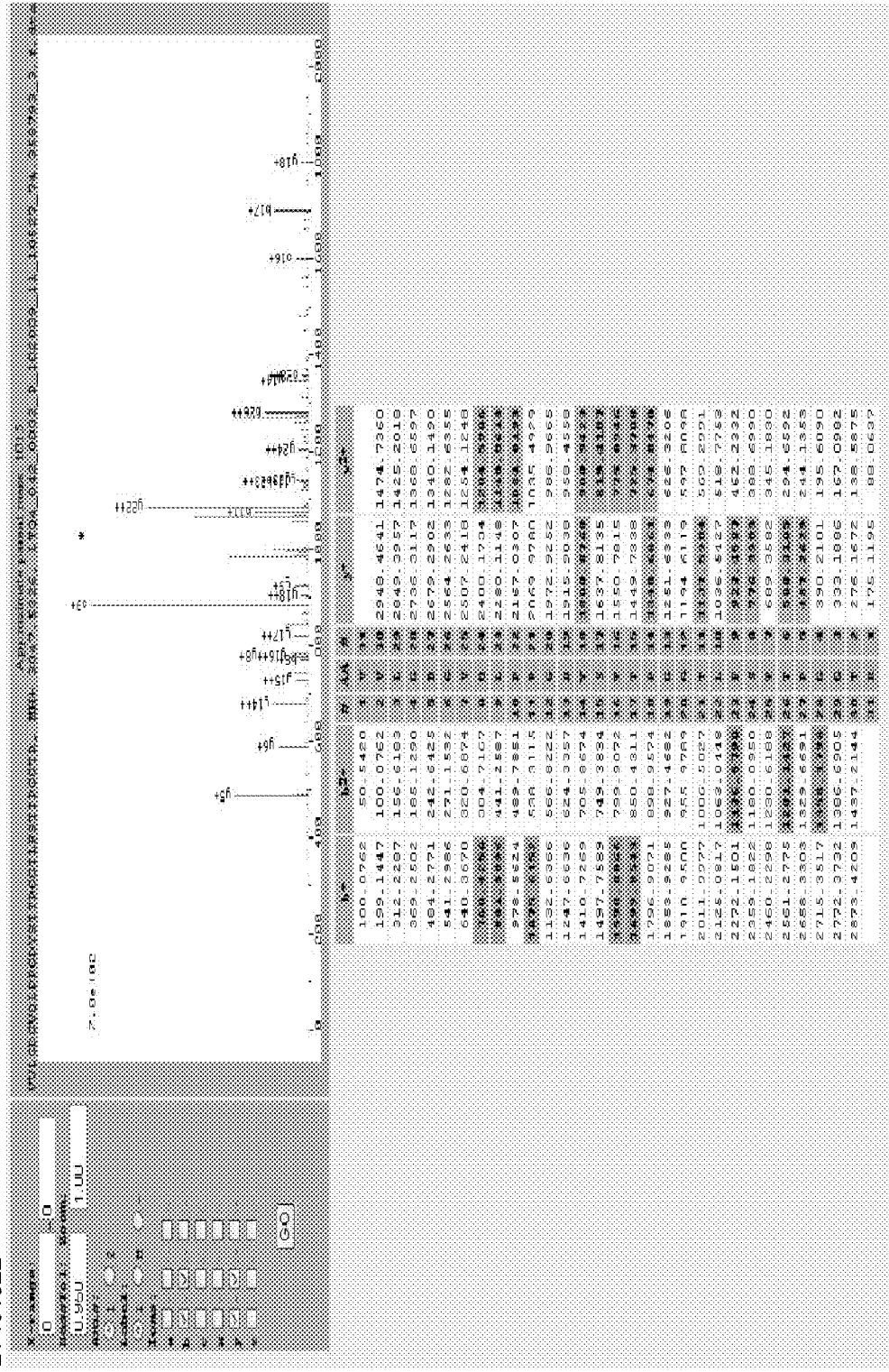
FIG. 1 cont. -- gi|PI00002569.3|sp|Q13541|rs|NP_004086| Eukaryotic translation initiation factor 4E-binding protein 1|gs|EIF4EBP1
LY401322

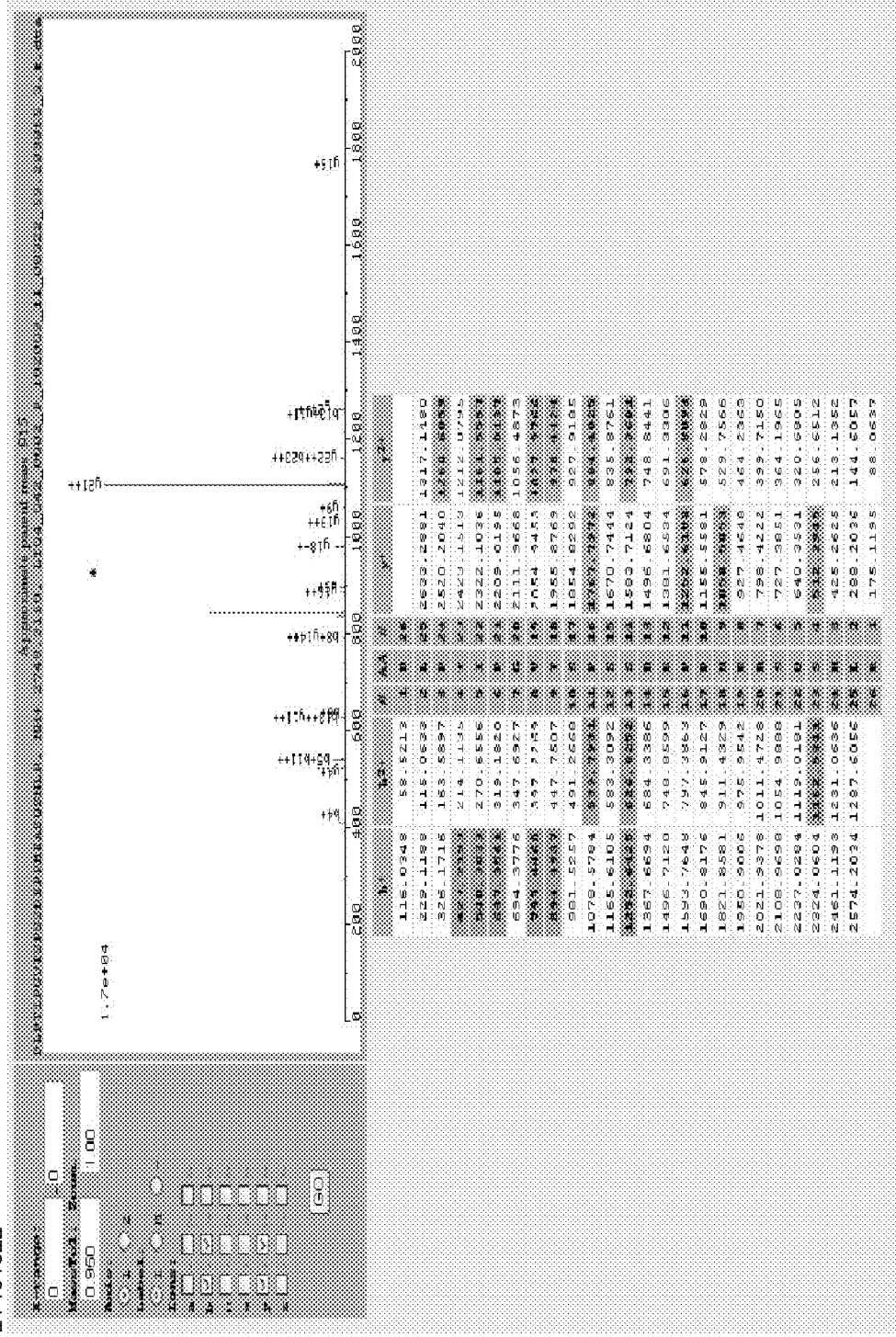
FIG. 1 cont. -- gi|IPI00002569.3|sp|Q13541|rs|NP_004086| Eukaryotic translation initiation factor 4E-binding protein 1|gs|EIF4EBP1 LY401322

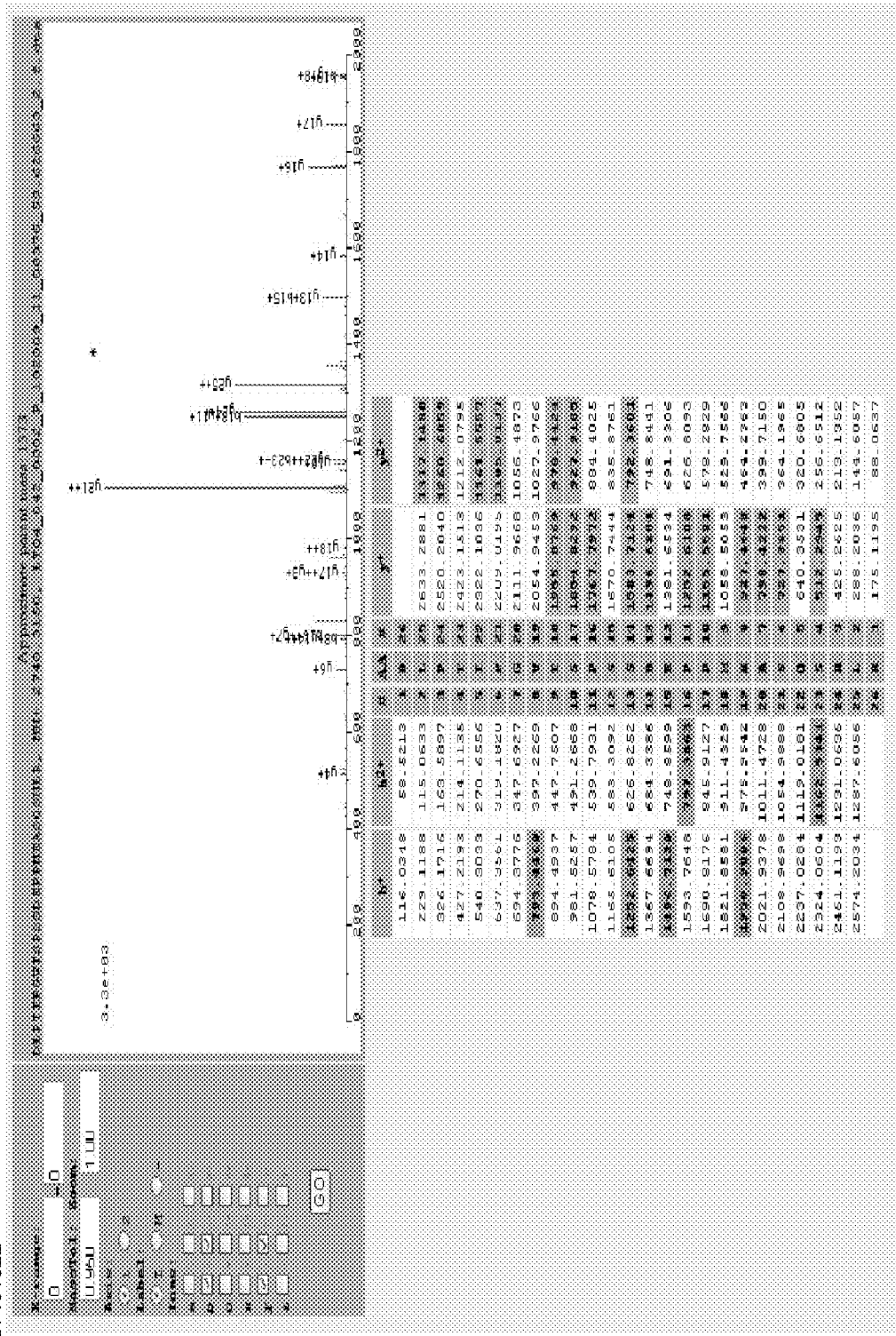
FIG. 1 cont. -- gi|PI00002569.3|sp|Q13541|rs|NP_004086| Eukaryotic translation initiation factor 4E-binding protein 1|gs|EIF4EBP1 LY401322

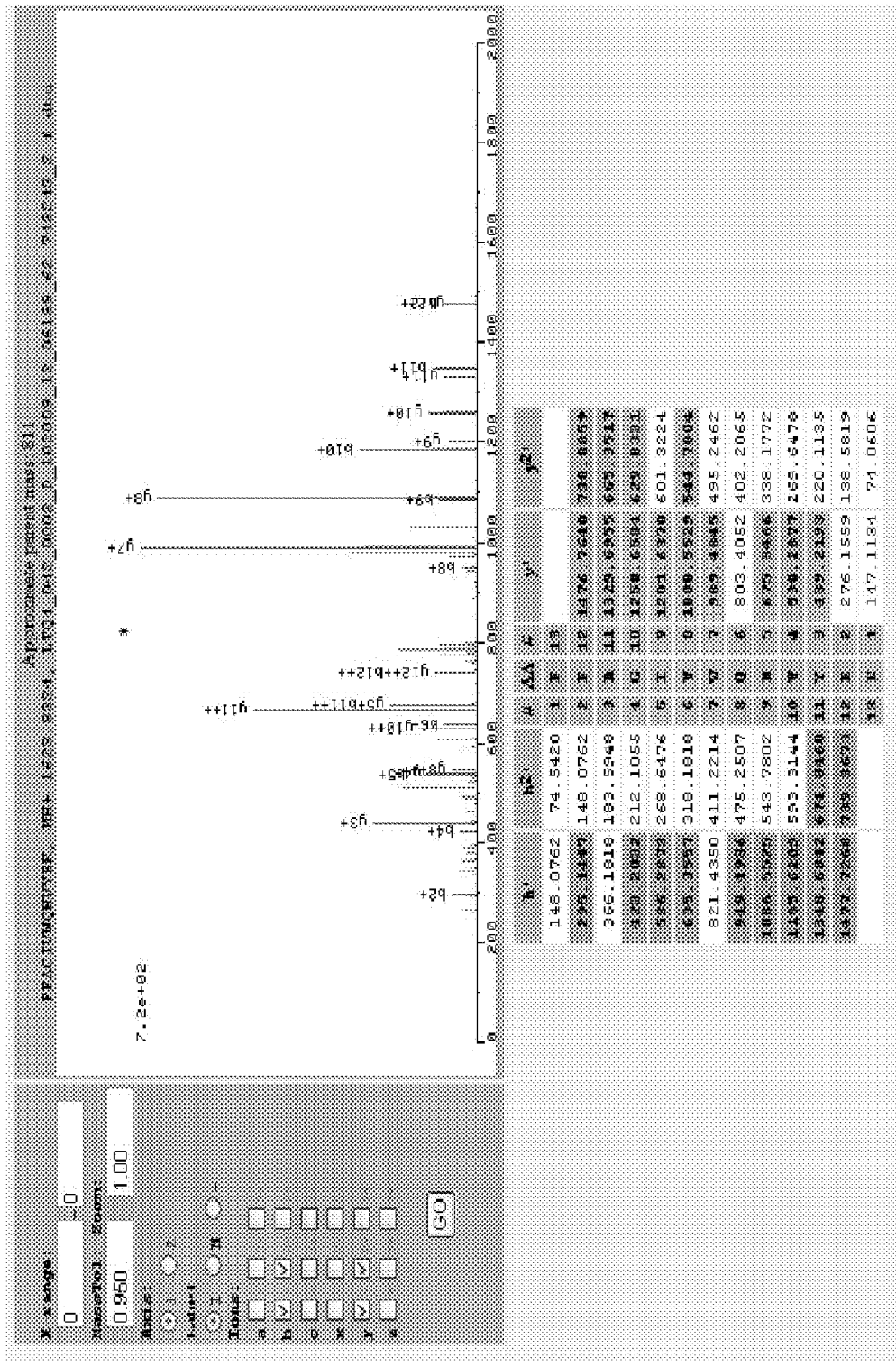
FIG. 1 cont. -- gi|IPI00012866.2|sp|P31749|rs|NP_001014431;NP_001014432;NP_005154|RAC-alpha serine/threonine-protein kinase|gs|AKT1 LY423056

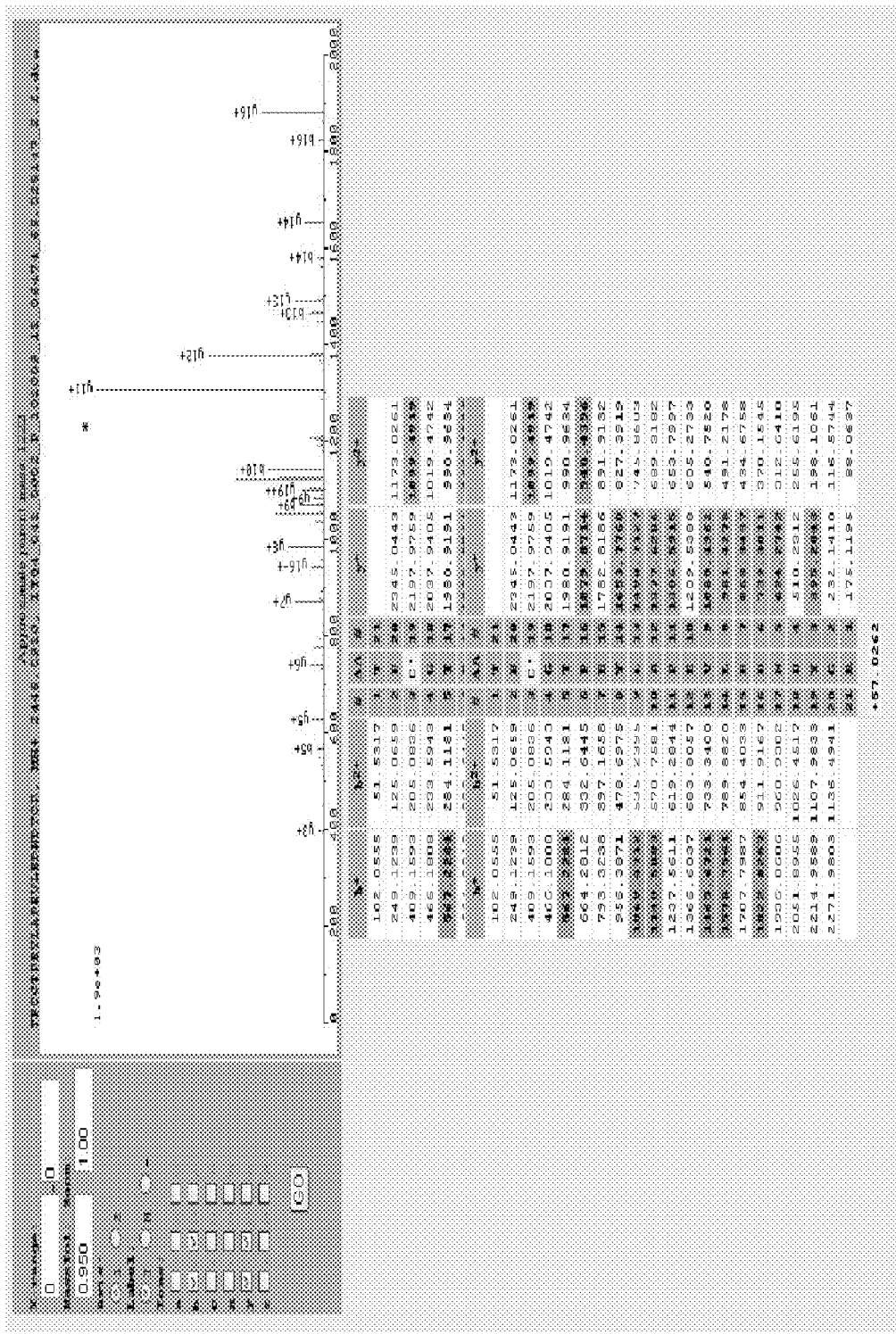
FIG. 1 cont. -- gi|PI00012866.2|sp|P31749|rs|NP_001014431;NP_001014432;NP_005154|RAC-alpha serine/threonine-protein kinase|gs|AKT1
LY423056

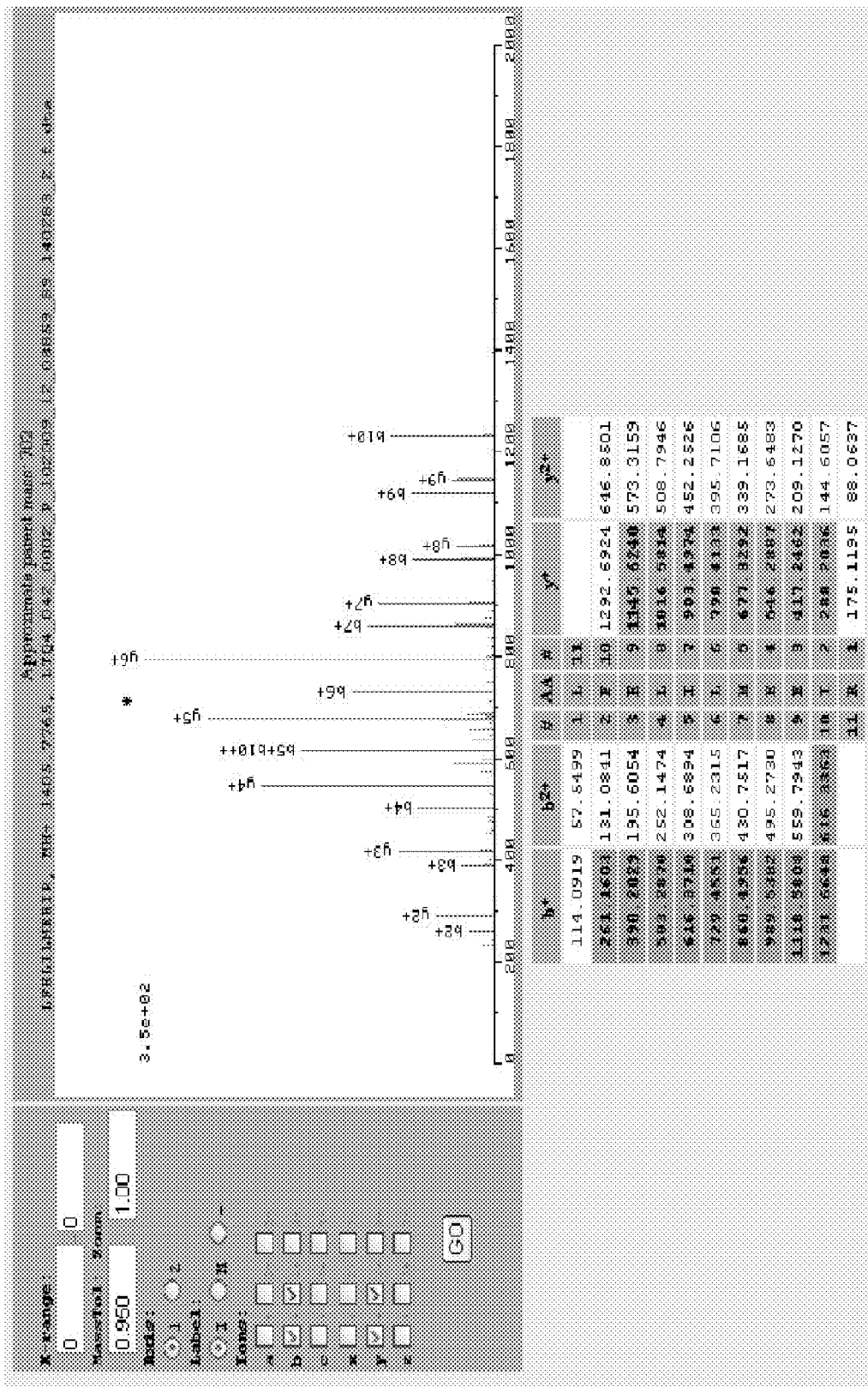
FIG. 1 cont. -- gi|IPI00012866.2|sp|P31749|rs|NP_001014431;NP_001014432;NP_005154|RAC-alpha serine/threonine-protein kinase|gs|AKT1 LY423056

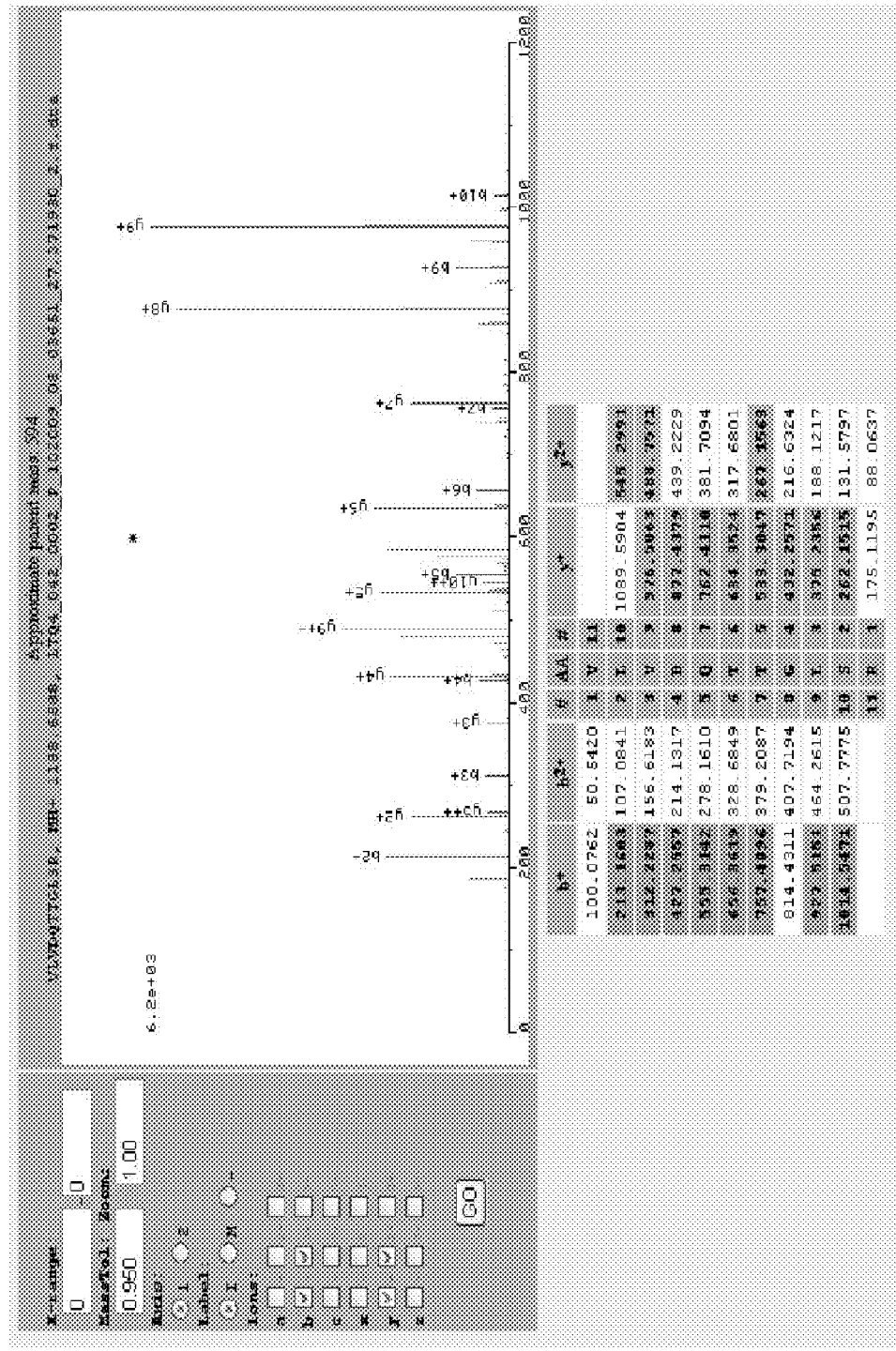
FIG. 1 cont. -- gi|IPI00301936.4|sp|Q15717|rs|NP_001410| cDNA FLJ60076, highly similar to ELAV-like protein 1|gs|ELAVL1 LY400549

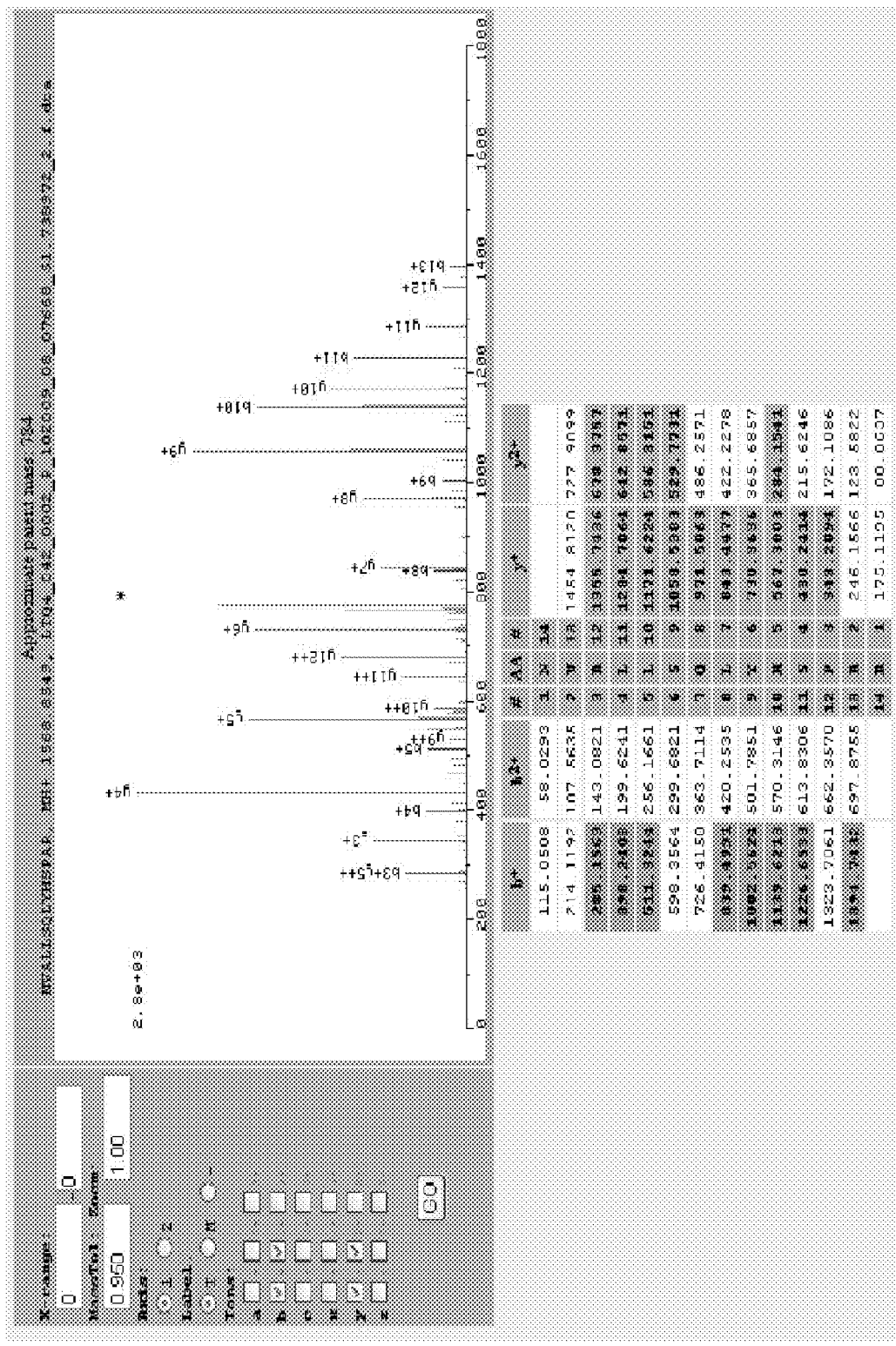
FIG. 1 cont. -- gi|IPI00301936.4|sp|Q15717|rs|NP_001410| cDNA FLJ60076, highly similar to ELAV-like protein 1|gs|ELAVL1 LY400549

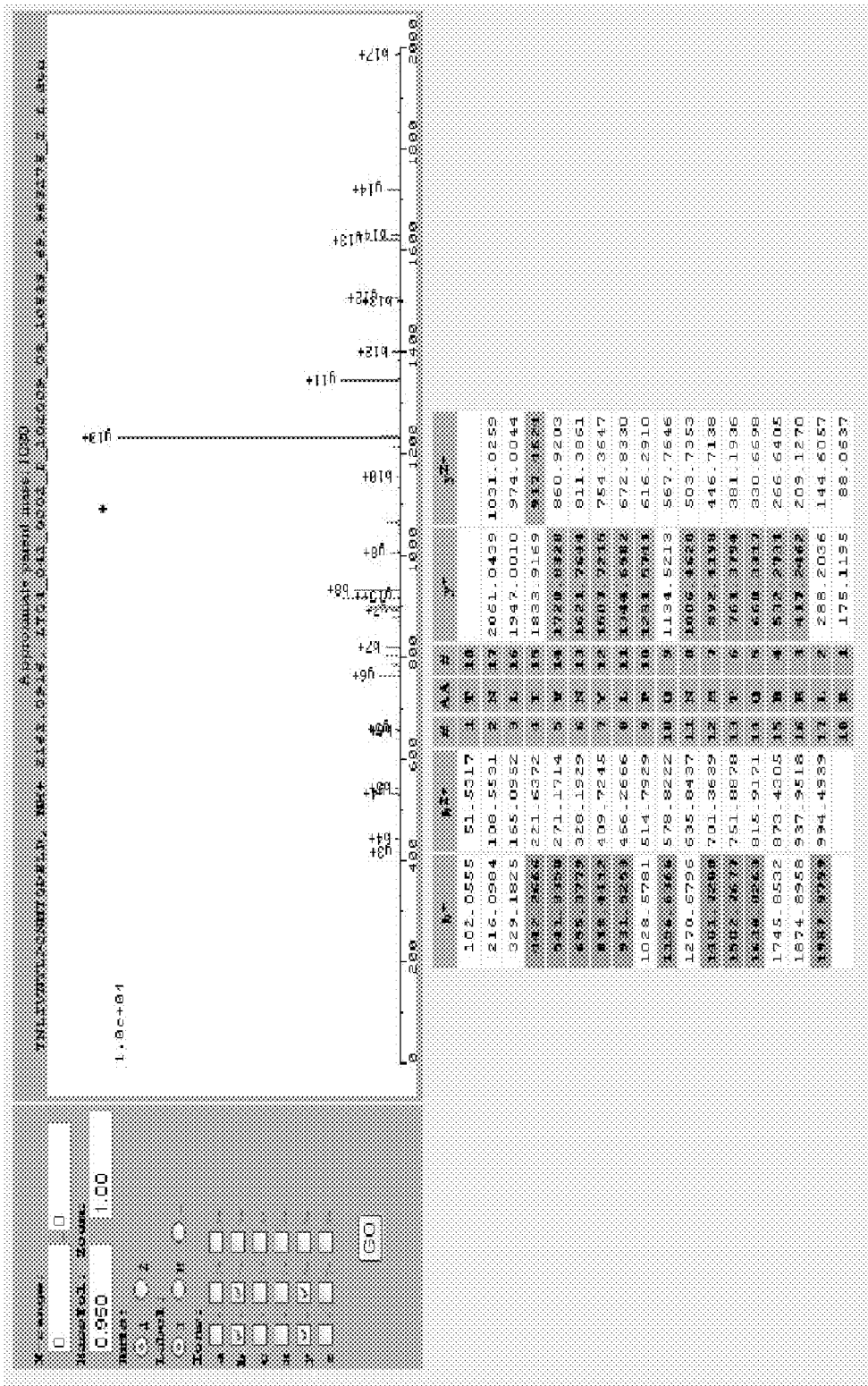
FIG. 1 cont. -- gi|IPI00301936.4|sp|Q15717|rs|NP_001410| cDNA FLJ60076, highly similar to ELAV-like protein 1|gs|ELAVL1 LY400549

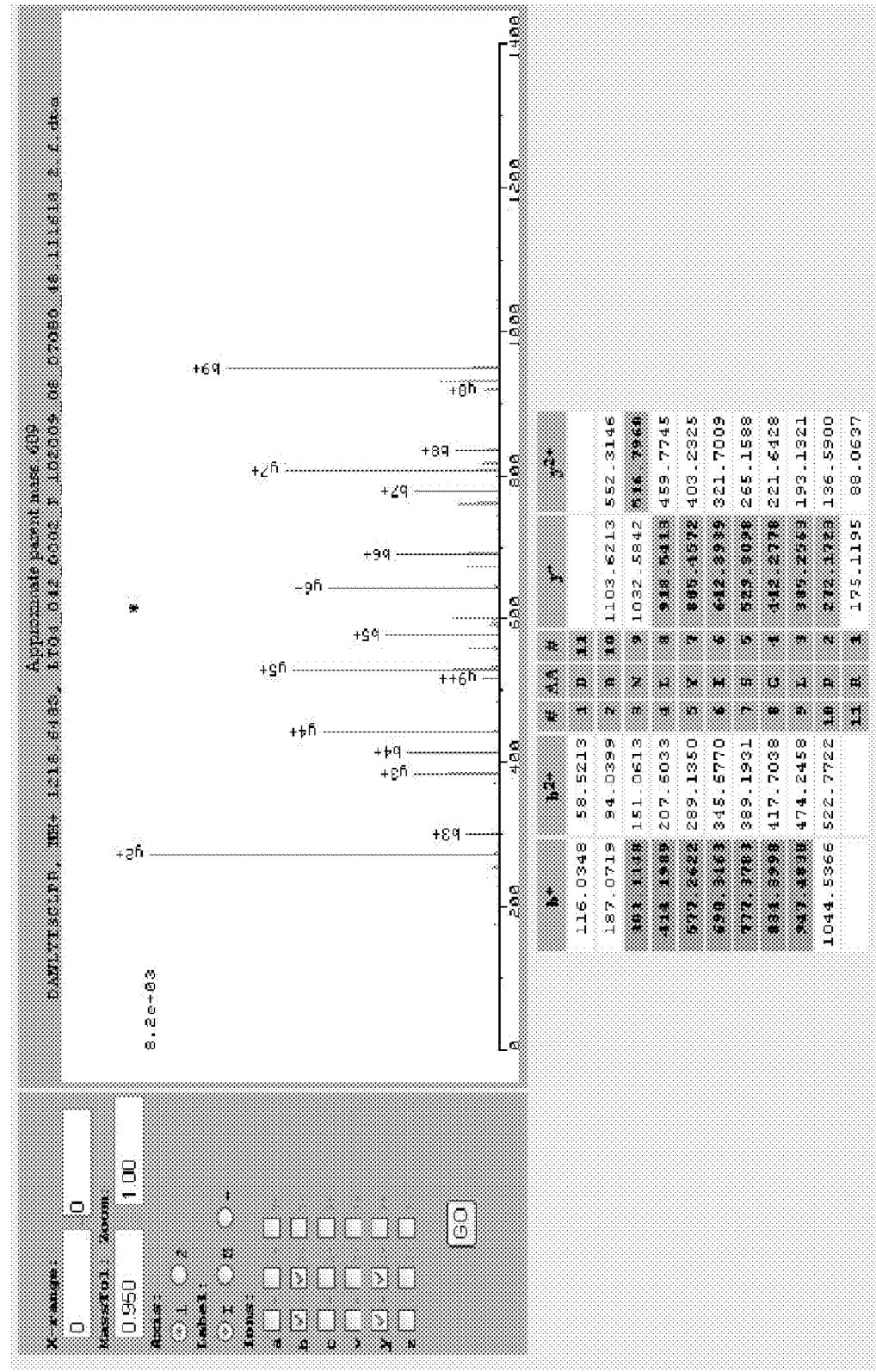
FIG. 1 cont. -- gi|PI00301936.4|sp|Q15717|rs|NP_001410| cDNA FLJ60076, highly similar to ELAV-like protein 1|gs|ELAVL1 LY400549

FIGURE 2

```
SEQ ID NO: 3 (cyclin D1 NP_444284.1)
1    mehqllccev etirraypda nllndrvlra mlkaeetcap svsyfkcvqk evlpsmrkiv
61   atwmlevcee qkceeevfpl amnyldrfls lepvkksrlq llgatcmfva skmketiplt
121  aeklciytdn sirpeellqm elllvnklkw nlaamtphdf iehflskmpe aeenkqiirk
181  haqtfvalca tdvkfisnpp smvaagsvva avqglnlrsp nnflsyyrlt rflsrvikcd
241  pdclracqeq ieallesslr qaqqnmdpka aeeeeeeeee vdlactptdv rdvdi SEQ ID NO: 4 (Vascular endothelial growth factor A NP_003367.4)
1    mtdrqtdtap spsyhllpgr rrtvdaaasr gqgpepapgg gvegvgargv alklfvqllg
61   csrfggavvr ageaepsgaa rsassgreep qpeegeeeee keeergpqwr lgarkpgswt
121  geaavcadsa paarapqala rasgrggrva rrgaeesgpp hspsrrgsas ragpgraset
181  mnfllswvhw slalllylhh akwsqaapma egggqnhhev vkfmdvyqrs ychpietlvd
241  ifqeypdeie yifkpscvpl mrcggccnde glecvptees nitmqimrik phqgqhigem
301  sflqhnkcec rpkkdrarqe kksvrgkgkg qkrkrkksry kswsvpcgpc serrkhlfvq
361  dpqtckcsck ntdsrckarq lelnertcrc dkprr SEQ ID NO: 5 (ornithine decarboxylase 1 NP_002530.1)
1    mnnfgneefd chfldegfta kdildqkine vsssddkdaf yvadlgdilk khlrwlkalp
61   rvtpfyavkc ndskaivktl aatgtgfdca skteiqlvqs lgvpperiiy anpckqvsqi
121  kyaanngvqm mtfdsevelm kvarahpkak lvlriatdds kavcrlsvkf gatlrtsrll
181  lerakelnid vvgvsfhvgs gctdpetfvq aisdarcvfd mgaevgfsmy lldigggfpg
241  sedvklkfee itgvinpald kyfpsdsgvr iiaepgryyv asaftlavni iakkivlkeq
301  tgsddedess eqtfmyyvnd gvygsfncil ydhahvkpll qkrpkpdeky ysssiwgptc
361  dgldriverc dlpemhvgdw mlfenmgayt vaaastfngf qrptiyyvms gpawqlmqqf
421  qnpdfppeve eqdastlpvs cawesgmkrh raacasasin v SEQ ID NO: 6: (nibrin NP_002476.2)
1 mwkllpaagp aggepyrllt gveyvvgrkn cailiendqs isrnhavlta nfsvtnlsqt
61 deipvltlkd nskygtfvne ekmqngfsrt lksgdgitfg vfgskfriey eplvacsscl
121 dvsgktalnq ailqlggftv nnwteecthl vmvsvkvtik ticalicgrp ivkpeyftef
181 lkaveskkqp pqiesfyppl depsigsknv dlsgrqerkq ifkgktfifl nakqhkklss
241 avvfgggear liteeneeeh nfflapgtcv vdtgitnsqt lipdcqkkwi qsimdmlqrq
301 glrpipeaei glavifmttk nycdpqghps tglktttpgp slsqgvsvde klmpsapvnt
361 ttyvadtese qadtwdlser pkeikvskme qkfrmlsqda ptvkesckts snnnsmvsnt
421 lakmripnyq lsptklpsin kskdrasqqq qtnsirnyfq pstkkrerde enqemsscks
481 arietscsll eqtqpatpsl wknkeqhlse nepvdtnsdn nlftdtdlks ivknsasksh
541 aaeklrsnkk remddvaied evleqlfkdt kpeleidvkv qkqeedvnvr krprmdietn
601 dtfsdeavpe sskisqenei gkkrelkeds lwsakeisnn dklqddseml pkklllltefr
661 slviknstsr npsginddyg qlknfkkfkk vtypgagklp hiiggsdlia hharkntele
721 ewlrqemevq nqhakeesla ddlfrynpyl krrr SEQ ID NO: 7: (pim-1 oncogene  NP_002639.1)
1    mllskinsla hlraapcndl hatklapgke keplesqyqv gpllgsggfg svysgirvsd
61   nlpvaikhve kdrisdwgel pngtrvpmev vllkkvssgf sgvirlldwf erpdsfvlil
121  erpepvqdlf dfiterqalq eelarsffwq vleavrhchn cgvlhrdikd enilidlnrg
181  elklidfgsg allkdtvytd fdgtrvyspp ewiryhryhg rsaavwslgi llydmvcgdi
241  pfehdeeiir gqvffrqrvs secqhlirwc lalrpsdrpt feeiqnhpwm qdvllpqeta
301  eihlhslspg psk
```

FIGURE 2 (continued)

```
SEQ ID NO: 8 (v-akt murine thymoma viral oncogene homolog 1  NP_001014432.1)
1    msdvaivkeg wlhkrgeyik twrpryfllk ndgtfigyke rpqdvdqrea plnnfsvaqc
61   qlmkterprp ntfiirclqw ttviertfhv etpeereewt taiqtvadgl kkqeeeemdf
121  rsgspsdnsg aeemevslak pkhrvtmnef eylkllgkgt fgkvilvkek atgryyamki
181  lkkevivakd evahtltenr vlqnsrhpfl talkysfqth drlcfvmeya nggelffhls
241  rervfsedra rfygaeivsa ldylhseknv vyrdlklenl mldkdghiki tdfglckegi
301  kdgatmktfc gtpeylapev ledndygrav dwwglgvvmy emmcgrlpfy nqdheklfel
361  ilmeeirfpr tlgpeaksll sgllkkdpkq rlgggsedak eimqhrffag ivwqhvyekk
421  lsppfkpqvt setdtryfde eftaqmitit ppdqddsmec vdserrphfp qfsysasgta SEQ ID NO: 9 (Eukaryotic translation initiation factor 4E binding protein 1
NP_004086.1)
1    msggsscsqt psraipatrr vvlgdgvqlp pgdysttpgg tlfsttpggt riiydrkflm
61   ecrnspvtkt pprdlptipg vtspssdepp measqshlrn spedkragge esqfemdi SEQ ID NO: 10 (Cyclin A2  NP_001228.1)
1    mlgnsapgpa treagsalla lqqtalqedq eninpekaap vqqprtraal avlksgnprg
61   laqqqrpktr rvaplkdlpv ndehvtvppw kanskqpaft ihvdeaekea qkkpaesqki
121  eredalafns aislpgprkp lvpldypmdg sfesphtmdm sivledekpv svnevpdyhe
181  dihtylreme vkckpkvgym kkqpditnsm railvdwlve vgeeyklqne tlhlavnyid
241  rflssmsvlr gklqlvgtaa mllaskfeei yppevaefvy itddtytkkq vlrmehlvlk
301  vltfdlaapt vnqfltqyfl hqqpanckve slamflgels lidadpylky lpsviagaaf
361  hlalytvtgq swpeslirkt gytleslkpc lmdlhqtylk apqhaqqsir ekyknskyhg
421  vsllnppetl nl SEQ ID NO: 11 (HuR (ELAV-like 1)  NP_001410)
1    msngyedhma edcrgdigrt nlivnylpqn mtqdelrslf ssigevesak lirdkvaghs
61   lgygfvnyvt akdaeraint lnglrlqskt ikvsyarpss evikdanlyi sglprtmtqk
121  dvedmfsrfg riinsrvlvd qttglsrgva firfdkrsea eeaitsfngh kppgssepit
181  vkfaanpnqn knvallsqly hsparrfggp vhhqaqrfrf spmgvdhmsg lsgvnvpgna
241  ssgwcifiyn lgqdadegil wqmfgpfgav tnvkvirdfn tnkckgfgfv tmtnyeeaam
301  aiaslngyrl gdkilqvsfk tnkshk
```

FIGURE 3

Akt

| | | | | |
|---|---|---|---|---|
| 1014.103 | 1013.481 | 31 | 39 | 0 NDGTFIGYK (SEQ ID No. 12) |
| 1053.099 | 1052.467 | 215 | 222 | 0 YSFQTHDR (SEQ ID No.13) |
| 1142.194 | 1141.547 | 40 | 48 | 0 ERPQDVDQR (SEQ ID No.14) |
| 1212.259 | 1211.476 | 113 | 121 | 0 QEEELMDFR (SEQ ID No.15) |
| 1244.326 | 1243.583 | 87 | 96 | 0 TFHVETPEER (SEQ ID No.16) |
| 1273.472 | 1272.606 | 145 | 154 | 0 VTMNEFEYLK (SEQ ID No.17) |
| 1284.348 | 1283.610 | 190 | 200 | 0 DEVAHTLTENR (SEQ ID No.18) |
| 1290.398 | 1289.604 | 347 | 356 | 0 LPFYNQDHEK (SEQ ID No.19) |
| 1305.521 | 1304.654 | 77 | 86 | 0 CLQWTTVIER (SEQ ID No.20) |
| | | | | (1)+C2H3ON@C |
| 1405.722 | 1404.768 | 357 | 367 | 0 LFELILMEEIR (SEQ ID No.21) |
| 1499.736 | 1498.836 | 65 | 76 | 0 TERPRPNTFIIR (SEQ ID No. 22) |
| 1623.874 | 1622.824 | 407 | 419 | 0 FFAGIVWQHVYEK (SEQ ID No. 23) |
| 1652.787 | 1651.774 | 466 | 480 | 0 RPHFPQFSYSASGTA (SEQ ID No. 24) |
| 1661.829 | 1660.830 | 97 | 111 | 0 EEWTTAIQTVADGLK (SEQ ID No. 25) |
| 1803.002 | 1801.921 | 421 | 436 | 0 LSPPFKPQVTSETDTR (SEQ ID No. 26) |
| 1850.150 | 1848.886 | 49 | 64 | 0 EAPLNNFSVAQCQLMK (SEQ ID No. 27) |
| | | | | (1)+C2H3ON@C |
| 1942.156 | 1940.951 | 252 | 268 | 0 FYGAEIVSALDYLHSEK (SEQ ID No. 28) |
| 2120.279 | 2118.973 | 122 | 142 | 0 SGSPSDNSGAEEMEVSLAKPK (SEQ ID No.29) |
| 2160.594 | 2158.946 | 329 | 346 | 0 AVDWWGLGVVMYEMMCGR (SEQ ID No. 30) |
| | | | | (1)+C2H3ON@C |
| 2290.652 | 2289.071 | 223 | 241 | 0 LCFVMEYANGGELFFHLSR (SEQ ID No. 31) |
| | | | | (1)+C2H3ON@C |
| 2446.634 | 2445.079 | 308 | 328 | 0 TFCGTPEYLAPEVLEDNDYGR (SEQ ID No. 32) |
| | | | | (1)+C2H3ON@C |
| 3470.728 | 3468.431 | 437 | 465 | 0 YFDEEFTAQMITITPPDQDDSMECVDSER (SEQ ID No. 33) |
| | | | | (1)+C2H3ON@C |

Pim1

| | | | | |
|---|---|---|---|---|
| 1008.142 | 1007.539 | 96 | 105 | 0 VSSGFSGVIR (SEQ ID No.34) |
| 1027.337 | 1026.614 | 86 | 94 | 0 VPMEVVLLK (SEQ ID No. 35) |
| 1055.239 | 1054.602 | 58 | 67 | 0 VSDNLPVAIK (SEQ ID No. 36) |
| 1133.353 | 1132.649 | 184 | 194 | 0 LIDFGSGALLK (SEQ ID No. 37) |
| 1146.311 | 1145.586 | 206 | 214 | 0 VYSPPEWIR (SEQ ID No. 38) |
| 1197.337 | 1196.560 | 14 | 24 | 0 AAPCNDLHATK (SEQ ID No. 39) |
| | | | | (1)+C2H3ON@C |
| 1214.341 | 1213.630 | 170 | 179 | 0 DENILIDLNR (SEQ ID No. 40) |
| 1228.395 | 1227.602 | 259 | 268 | 0 VSSECQHLIR (SEQ ID No. 41) |
| | | | | (1)+C2H3ON@C |
| 1289.321 | 1288.557 | 195 | 205 | 0 DTVYTDFDGTR (SEQ ID No. 42) |
| 1289.468 | 1288.566 | 157 | 166 | 0 HCHNCGVLHR (SEQ ID No. 43) |
| | | | | (2)+C2H3ON@C |
| 1344.447 | 1343.646 | 74 | 85 | 0 ISDWGELPNGTR (SEQ ID No. 44) |
| 1381.597 | 1380.719 | 146 | 156 | 0 SFFWQVLLAVR (SEQ ID No. 45) |
| 2697.985 | 2696.344 | 32 | 57 | 0 EPLESQYQVGPLLGSGGFGSVYSGIR (SEQ ID No.46) |
| 3349.834 | 3347.620 | 222 | 250 | 0 SAAVWSLGILLYDMVCGDIPFEHDEEIIR (SEQ ID No. 47) |
| | | | | (1)+C2H3ON@C |
| 3836.360 | 3833.966 | 106 | 136 | 0 LLDWFERPDSFVLILERPEPVQDLFDFITER (SEQ ID No. 48) |

FIGURE 3 (continued)

Nibrin

| | | | | |
|---|---|---|---|---|
| 1017.104 | 1016.513 | 532 | 540 | 0ISQENEIGK (SEQ ID No. 49) |
| 1089.278 | 1088.553 | 313 | 322 | 0MLSQDAPTVK (SEQ ID No. 50) |
| 1160.335 | 1159.623 | 344 | 353 | 0IPNYQLSPTK (SEQ ID No. 51) |
| 1175.325 | 1174.553 | 561 | 570 | 0LQDDSEMLPK (SEQ ID No. 52) |
| 1189.290 | 1188.577 | 634 | 642 | 0NTELEEWLR (SEQ ID No. 53) |
| 1194.263 | 1193.556 | 654 | 663 | 0EESLADDLFR (SEQ ID No. 54) |
| 1249.389 | 1248.646 | 156 | 168 | 0LSSAVVFGGGEAR (SEQ ID No. 55) |
| 1260.329 | 1259.621 | 364 | 374 | 0ASQQQQTNSIR (SEQ ID No. 56) |
| 1271.392 | 1270.619 | 11 | 23 | 0SGDGITFGVFGSK (SEQ ID No.57) |
| 1286.445 | 1285.676 | 487 | 497 | 0DTKPELEIDVK (SEQ ID No. 58) |
| 1341.468 | 1340.614 | 643 | 653 | 0QEMEVQNQHAK (SEQ ID No. 59) |
| 1356.411 | 1355.496 | 387 | 397 | 0DEENQEMSSCK (SEQ ID No. 60) |
| | | | | (2)HC2H3ON@C |
| 1420.499 | 1419.663 | 589 | 601 | 0NPSGINDDYGQLK (SEQ ID No. 61) |
| 1420.720 | 1419.700 | 207 | 217 | 0WIQSIMDMLQR (SEQ ID No. 62) |
| 1567.697 | 1566.730 | 327 | 341 | 0TSSNNNSMVSNTLAK (SEQ ID No. 63) |
| 1573.707 | 1572.699 | 239 | 252 | 0NYCDPQGHPSTGLK (SEQ ID No. 64) |
| | | | | (2)HC2H3ON@C |
| 1702.836 | 1701.842 | 253 | 269 | 0TTTPGPSLSQGVSVDEK (SEQ ID No. 65) |
| 1706.969 | 1705.937 | 617 | 632 | 0LPHIGGSDLIAHHAR (SEQ ID No. 66) |
| 2023.245 | 2021.950 | 470 | 486 | 0EMDDVAIEDEVLEQLFK (SEQ ID No. 67) |
| 2027.304 | 2025.938 | 26 | 43 | 0IEYEPLVACSSCLDVSGK (SEQ ID No. 68) |
| | | | | (2)HC2H3ON@C |
| 2115.213 | 2113.899 | 513 | 531 | 0MDIETNDTFSDEAVPESSK (SEQ ID No. 69) |
| 2229.472 | 2228.100 | 107 | 126 | 0QPPQIESFYPPLDEPSIGSK (SEQ ID No. 70) |
| 2284.749 | 2283.266 | 218 | 238 | 0QGLRPIPEAEIGLAVIFMTTK (SEQ ID No. 71) |
| 2289.592 | 2288.135 | 401 | 420 | 0IETSCSLLEQTQPATPSLWK (SEQ ID No. 72) |
| | | | | (2)HC2H3ON@C |
| 2656.209 | 2654.396 | 79 | 100 | 0TICALICGRPIVKPEYFTEFLK (SEQ ID No. 73) |
| | | | | (2)HC2H3ON@C |
| 2875.954 | 2874.279 | 423 | 447 | 0EQHLSENEPVDTNSDNNLFTDTDLK (SEQ ID No. 74) |
| 3453.743 | 3451.608 | 270 | 300 | 0LMPSAPVNTTTYVADTESEQADTWDLSERPK (SEQ ID No. 75) |
| 3475.008 | 3472.748 | 44 | 74 | 0TALNQAILQLGGFTVNNWTEECTHLVMVSVK (SEQ ID No. 76) |
| | | | | (2)HC2H3ON@C |

FIGURE 3 (continued)

ODC

| | | | | |
|---|---|---|---|---|
| 1027.101 | 1026.477 | 262 | 270 | 0 YFPSDSGVR (SEQ ID No. 77) |
| 1093.112 | 1092.493 | 28 | 37 | 0 INEVSSSDDK (SEQ ID No. 78) |
| 1399.544 | 1398.644 | 79 | 92 | 0 TLAATGTGFDCASK (SEQ ID No. 79) |
| | | | | (1)+C2H3ON@C |
| 1439.628 | 1438.734 | 38 | 50 | 0 DAFYVADLGDILK (SEQ ID No. 80) |
| 1545.753 | 1544.808 | 248 | 261 | 0 FEEITGVINPALDK (SEQ ID No. 81) |
| 1665.907 | 1664.909 | 93 | 107 | 0 TEIQLVQSLGVPPER (SEQ ID No. 82) |
| 1744.064 | 1742.960 | 278 | 293 | 0 YYVASAFTLAVNIIAK (SEQ ID No. 83) |
| 1877.021 | 1875.809 | 350 | 365 | 0 YYSSSIWGPTCDGLDR (SEQ ID No. 84) |
| | | | | (1)+C2H3ON@C |
| 2278.613 | 2277.011 | 122 | 141 | 0 YAANNGVQMMTFDSEVELMK (SEQ ID No. 85) |
| 2522.715 | 2521.031 | 1 | 21 | 0 MNNFGNEEFDCHFLDEGFTAK (SEQ ID No. 86) |
| | | | | (1)+C2H3ON@C |
| 3098.526 | 3096.391 | 217 | 245 | 0 CVFDMGAEVGFSMYLLDIGGGFPGSEDVK (SEQ ID No. 87) |
| | | | | (1)+C2H3ON@C |
| 3320.642 | 3318.582 | 186 | 216 | 0 ELNIDVVGVSFHVGSGCTDPETFVQAISDAR (SEQ ID No. 88) |
| | | | | (1)+C2H3ON@C |

VEGF

| | | | | |
|---|---|---|---|---|
| 1015.048 | 1014.473 | 71 | 81 | 0 AGEAEPSGAAR (SEQ ID No. 89) |
| 1192.448 | 1191.643 | 54 | 63 | 0 LFVQLLGCSR (SEQ ID No. 90) |
| | | | | (1)+C2H3ON@C |
| 1307.342 | 1306.590 | 153 | 165 | 0 GAEESGPPHSPSR (SEQ ID No. 91) |
| 1333.425 | 1332.518 | 319 | 329 | 0 QENPCGPCSER (SEQ ID No. 92) |
| | | | | (2)+C2H3ON@C |
| 1372.568 | 1371.660 | 332 | 342 | 0 HLFVQDPQTCK (SEQ ID No. 93) |
| | | | | (1)+C2H3ON@C |
| 1591.701 | 1590.775 | 31 | 48 | 0 GQGPEPAPGGGVEGVGAR (SEQ ID No. 94) |
| 1687.645 | 1686.674 | 88 | 101 | 0 EEPQPEEGEEEEEK (SEQ ID No. 95) |
| 1739.906 | 1738.863 | 5 | 20 | 0 QTDTAPSPSYHLLPGR (SEQ ID No. 96) |
| 2002.195 | 2000.937 | 115 | 134 | 0 KPGSWTGEAAVCADSAPAAR (SEQ ID No. 97) |
| | | | | (1)+C2H3ON@C |
| 2133.332 | 2131.985 | 203 | 222 | 0 WSQAAPMAEGGGQNHHEVVK (SEQ ID No. 98) |
| 2229.551 | 2228.127 | 289 | 307 | 0 IKPHQGQHIGEMSFLQHNK (SEQ ID No. 99) |
| 3061.448 | 3059.222 | 263 | 288 | 0 CGGCCNDEGLECVPTEESNITMQIMR (SEQ ID No. 100) |
| | | | | (4)+C2H3ON@C |
| 3081.635 | 3079.610 | 177 | 202 | 0 ASETMNFLLSWVHWSLALLLYLHHAK (SEQ ID No. 101) |

FIGURE 3 (continued)

```
Cyclin D1
```

| | | | | |
|---|---|---|---|---|
| 1001.145 | 1000.544 | 115 | 123 | 0 ETIPLTAEK (SEQ ID No. 102) |
| 1059.168 | 1058.481 | 261 | 269 | 0 QAQQNMDPK (SEQ ID No. 103) |
| 1260.372 | 1259.593 | 219 | 228 | 0 SPNNFLSYYR (SEQ ID No. 104) |
| 1261.357 | 1260.609 | 16 | 26 | 0 AYPDANLLNDR (SEQ ID No. 105) |
| 1488.638 | 1487.660 | 34 | 46 | 0 AEETCAPSVSYFK (SEQ ID No. 106) (1)+C2H3ON@C |
| 1538.896 | 1537.799 | 99 | 112 | 0 LQLLGATCMFVASK (SEQ ID No. 107) (1)+C2H3ON@C |
| 1560.794 | 1559.776 | 181 | 194 | 0 HAQTFVALCATDVK (SEQ ID No. 108) (1)+C2H3ON@C |
| 1736.043 | 1734.832 | 59 | 72 | 0 IVATWMLEVCEEQK (SEQ ID No. 109) (1)+C2H3ON@C |
| 1746.959 | 1745.861 | 246 | 260 | 0 ACQEQIEALLESSLR (SEQ ID No. 110) (1)+C2H3ON@C |
| 1818.129 | 1816.826 | 1 | 14 | 0 MEHQLLCCEVETIR (SEQ ID No. 111) (1)+C2H3ON@C |
| 1886.137 | 1884.838 | 73 | 87 | 0 CEEEVFPLAMNYLDR (SEQ ID No. 112) (1)+C2H3ON@C |
| 2157.481 | 2156.051 | 150 | 167 | 0 WNLAAMTPHDFIEHFLSK (SEQ ID No. 113) |
| 2398.813 | 2397.283 | 195 | 218 | 0 FISNPPSMVAAGSVVAAVQGLNLR (SEQ ID No. 114) |
| 2550.604 | 2549.059 | 270 | 291 | 0 AAEEEEEEEEEVDLACTPTDVR (SEQ ID No. 115) (1)+C2H3ON@C |
| 2905.430 | 2903.513 | 124 | 147 | 0 LCIYTDNSIRPEELLQMELLLVNK (SEQ ID No. 116) (1)+C2H3ON@C |

FIGURE 3 (continued)

eIF4E-BP1

| | | | | |
|---|---|---|---|---|
| 1312.376 | 1311.528 | 107 | 118 | 0AGGEESQFEMDI (SEQ ID No. 117) |
| 1341.446 | 1340.544 | 1 | 13 | 0MSGGSSCSQTPSR (SEQ ID No. 118) |
| | | | | (1)+C2H3ON@C |
| 2749.008 | 2747.307 | 74 | 99 | 0DLPTIPGVTSPSSDEPPMEASQSHLR (SEQ ID No. 119) |
| 3048.357 | 3046.524 | 21 | 51 | 0VVLGDGVQLPPGDYSTTPGGTLFSTTPGGTR (SEQ ID No. 120) |

Cyclin A2

| | | | | |
|---|---|---|---|---|
| 1025.176 | 1024.577 | 60 | 68 | 0GLAQQQRPK (SEQ ID No. 121) |
| 1039.264 | 1038.553 | 242 | 250 | 0FLSSMSVLR (SEQ ID No. 122) |
| 1061.184 | 1060.497 | 203 | 211 | 0QPDITNSMR (SEQ ID No. 123) |
| 1135.248 | 1134.589 | 401 | 410 | 0APQHAQQSIR (SEQ ID No. 124) |
| 1171.343 | 1170.581 | 1 | 12 | 0MLGNSAPGPATR (SEQ ID No. 125) |
| 1415.761 | 1414.821 | 253 | 266 | 0LQLVGTAAMLLASK (SEQ ID No. 126) |
| 1484.629 | 1483.730 | 96 | 108 | 0QPAFTIHVDEAEK (SEQ ID No. 127) |
| 1657.844 | 1656.847 | 123 | 138 | 0EDALAFNSAISLPGPR (SEQ ID No. 128) |
| 1666.895 | 1665.872 | 418 | 432 | 0YHGVSLLNPPETLNL (SEQ ID No. 129) |
| 1745.953 | 1744.878 | 77 | 91 | 0DLPVNDEHVTVPPWK (SEQ ID No. 130) |
| 1763.020 | 1761.918 | 212 | 226 | 0AILVDWLVEVGEEYK (SEQ ID No. 131) |
| 1799.017 | 1797.937 | 227 | 241 | 0LQNETLHLAVNYIDR (SEQ ID No. 132) |
| 2324.721 | 2323.202 | 329 | 349 | 0VESLAMFLGELSLIDADPYLK (SEQ ID No. 133) |
| 2511.946 | 2510.254 | 380 | 400 | 0TGYTLESLKPCLMDLHQTYLK (SEQ ID No. 134) |
| | | | | (1)+C2H3ON@C |
| 2669.921 | 2668.247 | 267 | 288 | 0FEEIYPPEVAEFVYITDDTYTK (SEQ ID No. 135) |
| 2710.935 | 2709.345 | 13 | 37 | 0EAGSALLALQQTALQEDQENINPEK (SEQ ID No. 136) |
| 3161.652 | 3159.675 | 350 | 378 | 0YLPSVIAGAAFHLALYTVTGQSWPESLIR (SEQ ID No. 137) |
| 3265.741 | 3263.643 | 301 | 328 | 0VLTFDLAAPTVNQFLTQYFLHQQPANCK (SEQ ID No. 138) |
| | | | | (1)+C2H3ON@C |

FIGURE 3 (continued)

Hur

| 998.081 | 997.417 | 121 | 128 | 0DVEDMFSR (SEQ ID No. 139) |
|---|---|---|---|---|
| 1003.083 | 1002.488 | 183 | 191 | 0FAANPNQNK (SEQ ID No. 140) |
| 1188.346 | 1187.651 | 137 | 147 | 0VLVDQTTGLSR (SEQ ID No. 141) |
| 1218.375 | 1217.640 | 105 | 115 | 0DANLYISGLPR (SEQ ID No. 142) |
| 1233.355 | 1232.616 | 207 | 217 | 0FGGPVHHQAQR (SEQ ID No. 143) |
| 1335.523 | 1334.719 | 93 | 104 | 0VSYARPSSEVIK (SEQ ID No. 144) |
| 1353.492 | 1352.682 | 38 | 50 | 0SLFSSIGEVESAK (SEQ ID No. 145) |
| 1568.796 | 1567.847 | 192 | 205 | 0NVALLSQLYHSPAR (SEQ ID No. 146) |
| 1714.835 | 1713.618 | 1 | 14 | 0MSNGYEDHMAEDCR (SEQ ID No. 147) (1)+C2H3ON@C |
| 1783.017 | 1781.910 | 56 | 72 | 0VAGHSLGYGFVNYVTAK (SEQ ID No. 148) |
| 2162.452 | 2161.083 | 20 | 37 | 0TNLIVNYLPQNMTQDELR (SEQ ID No. 149) |
| 2612.833 | 2611.276 | 158 | 182 | 0SLAELAITSENGHKPPGSSEPITVK (SEQ ID No. 150) |
| 2613.955 | 2612.203 | 286 | 309 | 0GFGFVTMTNYEEAAMAIASLNGYR (SEQ ID No. 151) |

4E

| 997.207 | 996.522 | 43 | 49 | 0WALWFFK (SEQ ID No. 2) |
|---|---|---|---|---|
| 1348.453 | 1347.565 | 96 | 106 | 0DGIEPMWEDEK (SEQ ID No. 152) |
| 1392.556 | 1391.650 | 163 | 173 | 0IAIWTTECENR (SEQ ID No. 153) (1)+C2H3ON@C |
| 1503.675 | 1502.772 | 193 | 206 | 0TVIGYQSHADTATK (SEQ ID No. 154) |
| 1758.862 | 1757.822 | 22 | 36 | 0TESNQEVANPEHYIK (SEQ ID No. 155) |
| 2299.495 | 2298.057 | 1 | 21 | 0MATVEPETTPTPNPPTTEEEK (SEQ ID No. 156) |
| 3393.800 | 3391.574 | 129 | 157 | 0FWLETLLCLIGESFDDYSDDVCGAVVNVR (SEQ ID No. 157) |
| 3612.058 | 3609.658 | 66 | 95 | 0FDTVEDFWALYNHIQLSSNLMPGCDYSLFK (SEQ ID No. 158) (1)+C2H3ON@C |

FIGURE 4 eIF4E Regulon Element Mass-Selective Mass Spectrometry Detection Analytes eIF4E
EAVTHIGR (Seq. ID No. 159)
WALWFFK (Seq. ID No. 2)

Cyclin D1
WNLAAMTPHDFIEHFLSK (Seq. ID No. 113)
ACQEQIEALLESSLR (Seq. ID No.110)
AEETCAPSVSYFK (Seq. ID No. 106)
LCIYTDNSIRPEELLQMELLLVNK (Seq. ID No. 116)

Nibrin/NBS-1
NPSGINDDYGQLK (Seq. ID No. 61)
EMDDVAIEDEVLEQLFK (Seq. ID No. 67)
LLPAAGPAGGEPYR (Seq. ID No. 160)
KQPPQIESFYPPLDEPSIGSK (Seq. ID No. 161)

Pim-1
ISDWGELPNGTR (Seq. ID No. 44)
DTVYTDFDGTR (Seq. ID No. 42)
LIDFGSGALLK (Seq. ID No. 37)
SLGILLYDMVCGDIPEHDEEIIR (Seq. ID No. 162)

ODC
FEEITGVINPALDK (Seq. ID No. 81)
INEVSSSDDKDAFYVADLGDILK (Seq. ID No. 163)
TLAATGTGFDCASK (Seq. ID No. 79)
LLDIGGGFPGSEDVK (Seq. ID No. 164)

SKP2
TLQVFGIVPDGTLQLLK (Seq. ID No. 165)
LLSQGVIAFR (Seq. ID No. 166)
LASDESLWQTLDLTGK (Seq. ID No. 167)
LSDPIVNTLAK (Seq. ID No. 168)

Cyclin E1
AILLDWLMEVCEVYK (Seq. ID No. 169)
DQHFLEQHPLLQPK (Seq. ID No. 170)
GSPLPVLSWANR (Seq. ID No. 171)
YMATQENVVK (Seq. ID No. 172)

MMP9
LGLGADVAQVTGALR (Seq. ID No. 173)
QLSLPETGELDSATLK (Seq. ID No. 174)
QSTLVLFPGDLR (Seq. ID No. 175)
SLGPALLLLQK (Seq. ID No. 176)

Caspase 9
LVEELQVDQLMDVLLSR (Seq. ID No. 177)
DHGFEVASTSPEDESPGSNPEPDATPFQEGLR (Seq. ID 178)
QLIIDLETR (Seq. ID No. 179)
KPEVLRPETPRPVDIGSGFGDVEQK (Seq. ID No. 180)

Bcl-X(L)
AFSDLTSQLHITPGTAYQSFEQVVNELFR (Seq. ID No. 181)
ELVVDFLSYK (Seq. ID No. 182)
QSFEQVVNELFR (Seq. ID No. 183)
EVIPMAAVK (Seq. ID No. 184)

eIF4E-BP1
RVVLGDGVQLPPGDYSTTPGGTLFSTTPGGTR (Seq. ID No. 185)
VVLGDGVQLPPGDYSTTPGGTLFSTTPGGTR (Seq. ID No. 120)
DLPTIPGVTSPSSDEPPMEASQSHLR (Seq. ID No. 119)
DLPTIPGVTSPSSDEPPMEASQSHLR (Seq. ID No. 119)

AKT1
FFAGIVWQHVYEK (Seq. ID No. 23)
TFCGTPEYLAPEVLEDNDYGR (Seq. ID No. 32)
EEWTAIQTVADGLK (Seq. ID No. 25)
LFELIMEEIR (Seq. ID No. 186)

ELAVL1/HuR
DANLYISGLPR (Seq. ID No. 142)
VLVDQTTGLSR (Seq. ID No. 141)
NVALLSQLYHSPAR (Seq. ID No. 146)
TNLIVNYLPQNMTQDELR (Seq. ID No. 149)

MASS SPECTROMETRY ASSAY FOR EIF4E AND EIF4E REGULON ACTIVITY

CROSS-REFERENCE TO RELATED APPLICATIONS

This application is a continuation-in-part of PCT/US08/082,611, filed Nov. 6, 2008, which claims priority to U.S. Provisional Patent Application No. 60/985,787, filed Nov. 6, 2007. The entire contents of each of these applications are hereby incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 24, 2013, is named TXZ00201_corrected.txt and is 84 KB in size.

BACKGROUND

Mass spectrometry (MS) is well established as a robust assay platform for small molecules, but it is often considered only as an exploratory research tool for proteins and peptides. This is partly because of the limited throughput of mass spectrometry-based assays and the need for extensive sample processing for most target peptides and proteins especially when the concentration of the target molecule is low. If this limitation can be overcome, mass spectrometry-based assays have advantages relative to antibody-based assays. For example, synthesis of a reference peptide can be done within a few days when the amino acid sequence of the target protein is known, compared to the many months that it takes to generate an antibody against a peptide. Once the reference peptide is available, setting up mass spectrometric conditions to measure the target peptide takes less than a week. When multiple cycles of reagent generation and evaluation are involved, the difference in time to set up a mass spectrometry based assay and antibody-based assay can be even more significant. Despite these advantages, many target proteins are beyond the reach of mass spectrometry because of the need for target enrichment before analysis. The most commonly used method of target enrichment is the use of antibody, which negates the advantage of the mass spectrometry-based assay unless the desired antibodies are already available.

The eukaryotic translation initiation factor eIF4E ("4E") is involved in the modulation of cellular growth. Moderate overexpression of 4E leads to dysregulated growth and malignant transformation. Both the nuclear and cytoplasmic function of 4E contribute to its ability to transform cells. Overexpression of 4E in vivo results in frank tumor formation, and the onset of tumor formation is greatly enhanced when 4E overexpression is placed within the context of a myc mouse background, suggesting again that 4E acts in concert with other oncogenes to promote neoplastic transformation. 4E is believed to represent one of the seven genes whose expression, when up-regulated in cancers, is predictive of metastatic disease. A variety of studies have been done demonstrating that existence of elevated 4E activity within surgical margins is a poor prognosis factor.

In the nucleus, 4E is a critical node in an RNA regulon that impacts nearly every stage of cell cycle progression (Culjkovic, B., Topisirovic, I. and K. L. B. Borden (2007) Controlling gene expression through RNA regulons. *Cell Cycle* 6: 65-69; Culjkovic, B., Topisirovic, I., Skranbanek, L., Ruiz-Gutierrez, M., and K. L. B. Borden (2006) eIF4E is a central node of an RNA regulon thatgoverns cellular proliferation. *J Cell Biol* 175: 415-426; Keene, J. D. (2007) RNA regulons: Coordination of post-transcriptional events. *Nature Reviews Genetics* 8: 533-543). Specifically, 4E coordinately promotes the mRNA export, and in some cases also translation, of several genes involved in cell cycle progression. For example, 4E functions to promote export from the nucleus to the cytoplasm of at least two mRNAs, cyclin D1 and ornithine decarboxylase (ODC), while having no impact on the nuclear to cytoplasmic transport of GAPDH or actin mRNAs. Moreover, there is evidence that the mRNA export function of 4E is linked to its oncogenic transformation activity. Dysregulated expression of tumor suppressors and oncogenes that maintain and enhance the malignant phenotype have been described. Among these molecules are tumor suppressors like p53, Rb, and APC and oncogenes such as myc, cyclin D1 and 4E. Their interaction constitute a network of self-reinforcing feedback loops wherein inactivation of principal elements can lead to the reversal and at times even the sustained loss of the neoplastic phenotype.

4E is overexpressed in a wide variety of malignant cell lines and primary human tumors including tumors of the breast, colon, head and neck, thyroid, lung, non-Hodgkin's lymphoma, prostate, cervix, bladder and chronic and acute myelogenous leukemias. Consistently, even moderate overexpression of 4E in rodent cells leads to deregulated proliferation and malignant transformation.

Despite being essential for growth and survival of eukaryotes by acting at a critical step of cap-dependent translation and recruiting transcripts to the ribosome as a result of its specific interaction with the 5'-7-methylguanosine (m7G) mRNA cap structure, up-regulation of 4E does not increase translation of all cap-dependent transcripts, but only of a specific subset of 4E-sensitive transcripts.

As much as 70% of 4E is present in the nuclei of mammalian cells, where it associates with nuclear bodies in a wide variety of organism, including yeast, Xenopus and humans. Here, 4E promotes transport of mRNAs of a specific subset of transcripts such as cyclin D1, but not of housekeeping genes such as B-actin and GAPDH. Post-transcriptional regulation of gene expression at the level of 4E mediated mRNA transport and translation exhibits different gene specificities, with some gene being regulated at the level of transport (e.g. cyclin D1) and some at the level of translation (VEGF), others at both levels (ODC), and still yet others at neither level (GAPDH). Binding to the m7G cap is required both for mRNA transport and translation by 4E, both of which contribute to this ability to transform cells.

Past observation indicates that 4E's capacity to discriminate between cyclin D1 and GAPDH is surprising seeing that the traditional view is that 4E binds the m7G cap found on all mRNAs regardless of other sequence specific features. Thus, this functional discrimination presents a conundrum in terms of our understanding of 4E mRNA recognition in the nucleus.

Elevated 4E activity has been observed to mediate selectively the translation (but not transcription) of a subset of the total collection of mRNAs expressed within cells, tissues, organs. Specifically, within cells, tumors and/or cancers where 4E activity is present at elevated levels, the translation of mRNA transcripts possessing complex 5'UTR regions is selectively upregulated. The repertoire of genes whose translation is thereby upregulated in circumstances where elevated 4E activity exists is a who's who of genes known to be involved in the regulation of the cell cycle, angiogenesis, proliferation and the like. However, the molecular mechanisms that regulate 4E transport, and how regulation of 4E activity could be used to modulate such processes, is not well-characterized.

Current diagnostic, segmentation and stratification methodologies do not provide for the enhanced detection, analysis and therapeutic monitoring of 4E and 4E regulon activity.

SUMMARY

Provided are highly sensitive high throughput mass spectrometry-based quantitative assays that provide for the single sample multiplexed analysis of at least one target protein, as well as in certain embodiments the simultaneous analysis of phosphorylation states of the at least one target protein. The mass spectrometry-based assays employ an enrichment method for the target protein(s), which allows the construction of highly sensitive, high-throughput assays without the use of an antibody. The assays can be adapted to detect 4E and 4E regulon component levels and phosphorylation states, and when so adapted becomes the first single sample analytical method of the 4E/4E regulon biological pathway.

This method may be incorporated into any of a variety of methods for compositions for the identification, diagnosis and monitoring of 4E and 4E regulon component activity and for the discovery of agents that modulate 4E and 4E regulon component activity.

Kits for the practice of the methods are also described herein.

These embodiments of the present invention, other embodiments, and their features and characteristics will be apparent from the description, drawings, and claims that follow.

BRIEF DESCRIPTION OF THE DRAWINGS

FIG. 1 discloses SEQ ID NOS: 2, 159, 2, 113, 110, 106, 116, 61, 67, 160, 161, 44, 42, 37, 162, 81, 163, 79, 164-178, 178, 178-185, 120, 119, 119, 32, 25, 23, 186, 141, 146, 149 and 142, respectively, in order of appearance.

FIG. 2 depicts sequences of 4E regulon components that may be detected using the assays described herein.

FIG. 3 depicts potential fragments of 4E regulon components produced using trypsin digestion that may be used to analyze the 4E regulon components using the assay described herein. The columns from left to right are as follows: monoisotopic mass, average mass, starting residue, ending residue, tryptic peptide sequence. FIG. 3 discloses the "Akt" sequences as SEQ ID NOS: 12-33, respectively, in order of appearance, the "Pim1" sequences as SEQ ID NOS: 34-48, respectively, in order of appearance, the "Nibrin" sequences as SEQ ID NOS: 49-76, respectively, in order of appearance, the "ODC" sequences as SEQ ID NOS: 77-88, respectively, in order of appearance, the "VEGF" sequences as SEQ ID NOS: 89-101, respectively, in order of appearance, the "Cyclin D1" sequences as SEQ ID NOS: 102-116, respectively, in order of appearance the "eIF4E-BP1" sequences as SEQ ID NOS: 117-120, respectively, in order of appearance, the "Cyclin A2" sequences as SEQ ID NOS: 121-138, respectively, in order of appearance, the "Hur" sequence as SEQ ID NOS: 139-151, respectively, in order of appearance and the "4E" sequences as SEQ ID NOS: 2 and 152-158, respectively, in order of appearance.

FIG. 4 presents 4E and 4E Regulon component mass-selective mass spectrometry detection analytes as provided by the Example below. FIG. 4 discloses the "eIF4E" sequences as SEQ ID NOS: 159 and 2, respectively, in order of appearance, the "Cyclin D1" sequences as SEQ ID NOS: 113, 110, 106 and 116, respectively, in order of appearance, the "Nibrin/NBS-1" sequences as SEQ ID NOS: 61, 67, 160 and 161, respectively, in order of appearance, the "Pim-1" sequences as SEQ ID NOS: 44, 42, 37 and 162, respectively, in order of appearance, the "ODC" sequences as SEQ ID NOS: 81, 163, 79 and 164, respectively, in order of appearance, the "SKP2" sequences as SEQ ID NOS: 165-168, respectively, in order of appearance, the "Cyclin E1" sequences as SEQ ID NOS: 169-172, respectively, in order of appearance, the "MMP9" sequences as SEQ ID NOS: 173-176, respectively, in order of appearance, the "Caspase 9" sequences as SEQ ID NOS: 177-180, respectively, in order of appearance, the "Bcl-X(L)" sequences as SEQ ID NOS: 181-184, the "eIF4E-BP1" sequences as SEQ ID NOS: 185, 120, 119 and 119, respectively, in order of appearance, the "AKT1" sequences as SEQ ID NOS: 23, 32, 25 and 186, respectively, in order of appearance, and the "ELAVL1/HuR" sequences as SEQ ID NOS: 142, 141, 146 and 149, respectively, in order of appearance.

DETAILED DESCRIPTION

Figure 1:
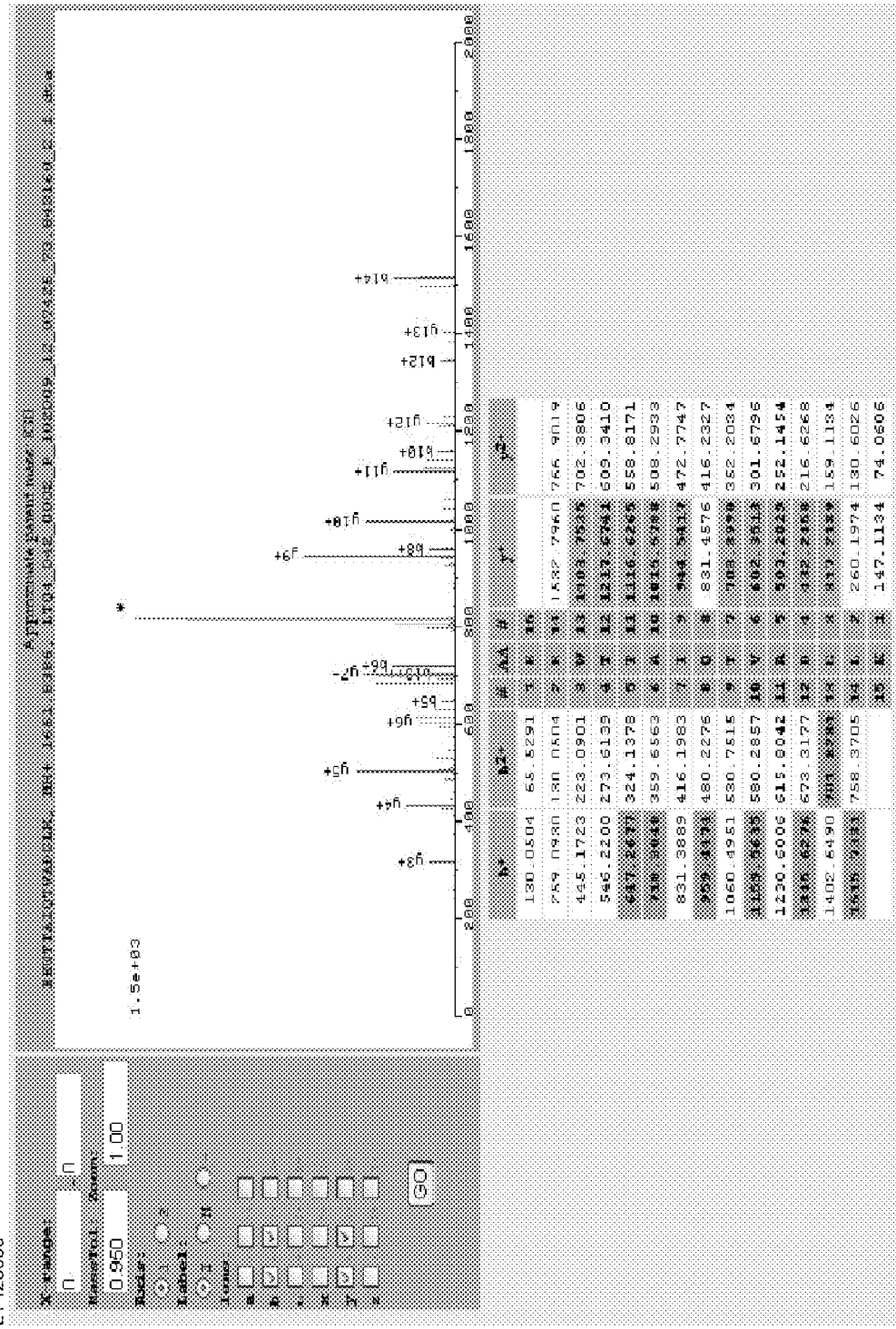
FIG. 1 depicts the mass spectra obtained by an embodiment of an assay for detection of 4E and 4E regulon component levels as described in the Example below.

For convenience, certain terms employed in the specification, examples, and appended claims are collected here. Unless defined otherwise, all technical and scientific terms used herein have the same meaning as commonly understood by one of ordinary skill in the art to which this invention belongs.

The term "4E activity" or "activity of 4E" includes any of the biological effects of the 4E gene or protein, including but not limited to elevated expression of 4E, elevated protein levels of 4E, and/or activation of 4E regulon components, and phosphorylation state of 4E.

The term "4E regulon activity" or "4E regulon component activity" or "activity of a 4E regulon component" refers the activity of 4E as a mediator of the 4E regulon and also includes 4E regulon activation, expression, transport and/or activity of the 4E regulon components.

The term "4E regulon component" refers to 4E (SEQ ID NO: 1 MATVEPETTPTPNPPTTEEEKTESNQE-VANPEHYIKHPLQNRWALWFFKNDKSKTWQANL RLISKFDTVEDFWALYNHIQLSSN-LMPGCDYSLFKDGIEPMWEDEKNKRGGR-WLITLNKQ QRRSDLDRFWLETLLCLIGESFDDYSD-DVCGAVVNVRAKGDKIAIWTTECENREAVTHIGR VYKERLGLPPKIVIGYQSHADTATKSGSTTKNRFVV), any of the components of its regulon, and any modifier of the regulon such as HuR. Exemplary 4E regulon components include: eIF4E (gi: 54873625) (NP_001959, NP_001959.1); Cyclin D1 (gi: 77628152) (NP_444284, NP_444284.1); NBS/Nibrin (gi: 67189763) (NP_002476, NP_002476.2); Pim-1 (gi: 31543400) (NP_002639, NP_002639.1); Cyclin B1 (gi: 34304372) (NP_114172, NP_114172.1); Cyclin A2 (gi: 16950653) (NP_001228, NP_001228.1); ODC (gi: 4505488) (NP_002530, NP_002530.1); VEGF (gi: 71051577) (NP_003367, NP_003367.4); Skp2 (gi: 16306594, 16306593) (NP_005974, NP005974.2, NP_116026, NP_116026.1); Cyclin E1 (gi: 17318558) (NP_001229, NP_001229.1); c-myc (gi: 71774082) (NP_002458, NP_002458.2); FGF2 (gi: 153285460, 153285461) (NP_2006, NP_001997, (NP_001997.5); MMP-9 (gi: 74272286) (NP_004985, NP_004985.2); mdm2 (gi: 46488903) (NP_002383, NP_002383.2); caspase-9 (gi: 14790123, 14790127) (NP_001220, NP_001220.2, NP_127463, NP_127463.1); bcl2 (gi: 72198188, 72198345) (NP_000624, NP_000624.2, NP_000648, NP_000648.2); Bcl/xL (gi: 20336334) (NP_612815, NP_612815.1); Fbox1 (gi: 16306583); CGGbp1 (gi: 56550052); P54nrb/NONO.1 gi: 34932413); Selenoprotein S (gi: 33285002, 45439347) (NP_060915, (NP_060915.2, NP_018445, NP_018445.4) eIF4E-BP1 (gi: 117938308) (NP _004086, NP_004086.1); Akt1 (gi: 62241012, 62241010, 62241014) (NP_001014431, NP_001014431.1, NP _005154, NP_005154.2, NP _001014432, NP_001014432.1); PI3K (gi: 54792081, 21237724) (NP_006209, NP_006209.2, NP_002640, NP_002640.2); GSK3B (gi: 21361339) (NP_002084, NP_002084.2); HuR (gi: 38201714) (NP_001410, NP_001410.2); and mTOR/FRAP1 (gi: 19924298) (NP_004949, NP_004949.1). Preferred 4E regulon components (components) to be used in certain of the below-described methods are 4E, 4E-BP1, NBS/Nibrin, Pim-1, VEGF, Cyclin D1, Cyclin A2, ODC and HuR. A "regulon" is a family of multiple mRNAs that are coordinately regulated in a sequence specific fashion by one or more RNA binding proteins that orchestrate and control their splicing, export, stability, localization and/or translation.

The articles "a" and "an" are used herein to refer to one or to more than one (i.e., to at least one) of the grammatical object of the article. By way of example, "an component" means one component or more than one component.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics arginine (Arg or R) would have a positive charge moiety located in similar molecular space and having the same degree of mobility as the .epsilon.-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

The term "biological sample", or "sample" as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The terms "comprise" and "comprising" are used in the inclusive, open sense, meaning that additional components may be included.

As used herein, the term "fragment" when used in reference to a polypeptide or parent polypeptide is intended to mean any truncated or smaller mass form, corresponding to either carboxyl-terminal, amino-terminal, or both regions, of a reference polypeptide or parent polypeptide. Accordingly, a deletion of a single amino acid from the carboxyl- or amino-terminus is considered a fragment of a parent polypeptide. The term fragment therefore includes deletion of amino acids at the amino- and/or carboxyl-terminus as well as modifications where, for example, an amino acid side chain is removed but the peptide bond remains. A fragment includes a truncated polypeptide that is generated, for example, by polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation. Furthermore, a fragment can also result from multiple cleavage events such that a truncated polypeptide resulting from one cleavage event can be further truncated by additional cleavage events.

The term "including" is used to mean "including but not limited to". "Including" and "including but not limited to" are used interchangeably.

"Protein" and "polypeptide" are used interchangeably herein when referring to a gene product, e.g., as may be encoded by a coding sequence. By "gene product" it is meant a molecule that is produced as a result of transcription of a gene. Gene products include RNA molecules transcribed from a gene, as well as proteins translated from such transcripts.

Provided, in one aspect, is a method for determining the level of and/or phosphorylation state of at least one target protein, in some embodiments simultaneously, in a single sample, comprising: (a) adding at least one internal standard protein or peptide corresponding to each target protein to the sample; (b) reducing and alkylating the at least one target protein and internal standard in the sample without the use of urea; (c) digesting the at least one target protein and the at least one internal standard protein or peptide by contacting the sample with at least one protease; (d) analyzing the fragments of said digesting by a mass spectrometry-based method; and (e) determining the level of and/or phosphorylation state of the at least one target protein using the results of the analysis of the fragments.

In certain embodiments, there are at least two, three, four, five, ten or more target proteins for which the level and/or phosphorylation state are determined. In certain embodiments the level and/or phosphorylation state of the target protein are determined simultaneously, i.e., in a multiplexed fashion.

The internal standard protein or peptide corresponds to the target protein (or a fragment of it), but includes appropriate corresponding internal marker amino acids (e.g. Leu residue with the molecular weight 7 amu higher than the natural counterpart) to modify the mass of the internal standard protein or peptide to make it distinguishable from the target protein. The protein may be modified by naturally occurring modifications such as post-translational modifications, including phosphorylation, lipidation, prenylation, sulfation, hydroxylation, acetylation, ubiquitination, glycosylation, methylation, palmitoylation, myristylation, addition of carbohydrate, addition of prosthetic groups or cofactors, formation of disulfide bonds, proteolysis, assembly into macromolecular complexes, and the like.

A modification of a protein can also include non-naturally occurring derivatives, analogues and functional mimetics thereof generated by, for example, chemical synthesis. For example, derivatives can include chemical modifications of the protein such as alkylation, acylation, carbamylation, iodination, or any modification that derivatizes the protein. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those proteins which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Another specific example of a modification of a protein includes modification of proteins in a sample with a moiety having a stable isotope. For example, two different proteins can be separately labeled with moieties that are isotopically distinct, and such differentially labeled proteins can be compared. Modification of proteins with stable isotopes can be used for both quantitating the relative amount of one or more proteins in a sample.

Polypeptides can be differentially labeled by a variety of methods well known to those skilled in the art, for example, a label can be included at any position within a polypeptide for which specific chemistries or biochemical methods are available. Such positions include, for example, carboxyl and amino terminal, and amino acid side chains. A specific example of labeling carboxyl moieties, including the carboxyl terminus of a polypeptide and side chains is the esterification using methanol. Additionally cysteine can be used to attach labels through, for example, an iodoacetamide reactive group. Polypeptides in a sample can also be labeled with a moiety having a stable isotope. A moiety can be produced that is enriched or depleted in a particular stable isotope, for example, a stable isotope of an element can contain trace amounts of a different atomic weight isotope of that element which can be depleted before incorporating into the labeling moiety. Isotopic labels that can be used to label amino acids include, for example, isotopically heavy and light versions of hydrogen, carbon, oxygen, nitrogen, sulfur and selenium. The corresponding heavy isotopes of these light atoms include: $^2H$, $^{13}C$, $^{17}O$, $^{15}N$, $^{33}S$, $^{34}S$, and $^{35}S$.

Differentially labeled polypeptides are useful for determining the relative abundance of a polypeptide, or polypeptides, in two different samples. Changes in abundance of a particular polypeptide between two samples can indicate a role for that polypeptide in a biological process. For example, polypeptides from one sample can be labeled with a light isotope containing label while polypeptides from another sample are labeled with a heavy isotope containing label. The two different samples can be, for example, polypeptides extracted from a normal cell and a cancerous cell. A particular polypeptide species that is present in both samples will be chemically the same in the two samples except for the mass of the label or the chemistry used to attach the label. Because the differentially labeled polypeptides behave physicochemically the same, the same polypeptides in the two samples will ionize or fragment similarly, but still be distinguishable by MS due to the isotopic difference in the differential label. Accordingly, the relative amounts of the same polypeptides can be readily compared and quantitated.

Reduction and alkylation of the target proteins and internal standard proteins may be performed essentially as described earlier (Hale J E et al (2004) Anal Biochem 333:174-181) with the modifications described in the example. A key modification is that no urea should be used in this step.

The reduced and alkylated target proteins and internal standard proteins or peptides are then fragmented. Polypeptides can be fragmented by a number of methods including polypeptide cleavage using a chemical reagent, enzyme, or energy input. A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid. A fragment can also be generated by a mass spectrometry method including, for example, all types of fragmentation methods and collision induced dissociation (CID). Furthermore, a fragment can also result from multiple cleavage events such that a truncated polypeptide resulting from one cleavage event can be further truncated by additional cleavage events. Several identical or different fragments can be obtained from the original, or parent, polypeptide. The methods of the invention can use one or more polypeptide fragments from a population of polypeptide fragments.

Analysis of the digested fragments may be by any mass spectrometry-based method that allows high-throughput multiplexed analysis. Mass spectrometry is a sensitive and accurate technique for separating and identifying molecules. Generally, mass spectrometers have two main components, an ion source for the production of ions and a mass-selective analyzer for measuring the mass-to-charge ratio of ions, which is and converted into a measurement of mass for these ions. Several ionization methods are known in the art and described herein. Different mass spectrometry methods, for example, quadrupole mass spectrometry, ion trap mass spectrometry, time-of-flight mass spectrometry and tandem mass spectrometry can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions. The ability to precisely control the movement of ions in a mass spectrometer allows for greater options in detection protocols which can be advantageous when a large number of fragments, for example, from a multiplex experiment, are being analyzed. Mass spectrometry methods are well known in the art (see Burlingame et al. Anal. Chem. 70:647 R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass. Mass spectrometry technology exists by which several thousands of protein species can be separated, detected and quantified in a single operation.

The mass spectrometry may be preceded by a chromatography step. New chromatography based methods for the identification of the proteins contained in complex mixtures without the need for separation of the mixture into individual protein components are available. A separation step can also be used to remove salts, enzymes, or other buffer components. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniturized apparutus is used, a micro-affinity chromatography separation step can be used. In addition, whether a separation step is desired, and the choice of separation method, can depend on the detection method used. For example, the efficiency of matrix-assisted laser desorption/ionization and electrospray ionization can be improved by removing salts from a sample. For example, salts can absorb energy from the laser in matrix-assisted laser desorption/ionization and result in lower ionization efficiency.

In a preferred embodiment, the method is LC-MS/MS. Currently, up to 10,000 sequencing runs can be recorded in a single LC-MS analysis of 60 minutes duration. Often the duty cycle of the mass spectrometer is the rate limiting step, however, as mass spectrometers continue to improve, the number of polypeptides that can be detected and/or sequenced in one run will continue to increase. Further automation and on-line analysis will greatly improve the efficiency of mass spectrometry. Therefore, as the instrumentation increases in efficiency the rate of polypeptides that can be detected and/or sequenced with the methods of the invention will also concurrently increase.

In certain embodiments, the above-described methods may be adapted for specifically detecting the level and/or phosphorylation state of 4E and/or at least one 4E regulon component. In one embodiment, the at least one target protein is 4E is at least in part on the analysis of the fragment SEQ ID NO: 2 WALWFFK which has a parent mass of 498 Da. The transitions from the parent mass used in the determination are 498->740, 498->627 and 498->371. In other embodiments, the at least one target protein is a 4E regulon component and is selected from the group consisting of: eIF4E (gi: 54873625) (NP_001959, NP_001959.1); Cyclin D1 (gi: 77628152) (NP_444284, NP_444284.1); NBS/Nibrin (gi: 67189763) (NP_002476, NP_002476.2); Pim-1 (gi: 31543400) (NP_002639, NP_002639.1); Cyclin B1 (gi: 34304372) (NP_114172, NP_114172.1); Cyclin A2 (gi: 16950653) (NP_001228, NP_001228.1); ODC (gi: 4505488) (NP_002530, NP_002530.1); VEGF (gi: 71051577) (NP_003367, NP_003367.4); Skp2 (gi: 16306594, 16306593) (NP_005974, NP_005974.2, (NP_116026, NP_116026.1); Cyclin E1 (gi: 17318558) (NP_001229, NP_001229.1); c-myc (gi: 71774082) (NP_002458, NP_002458.2); FGF2 (gi: 153285460, 153285461) (NP_2006, NP_2006.4, NP_0001997, NP_001997.5); MMP-9 (gi: 74272286) (NP_004985, NP_004985.2); mdm2 (gi: 46488903) (NP_002383, NP_002383.2); caspase-9 (gi: 14790123, 14790127) (NP_001220, NP_001220.2, (NP_127463, NP_127463.1); bcl2 (gi:72198188, 72198345) (NP_000624, NP_000624.2, (NP_000648, NP_000648.2); Bcl/xL (gi: 20336334) (NP_612815, NP_612815.1); Fbox1 (gi: 16306583); CGGbp1 (gi: 56550052); P54nrb/NONO.1 (gi: 34932413); Selenoprotein S (gi:33285002, 45439347) (NP_060915, NP_060915.2, NP_018445, NP_018445.4); eIF4E-BP1 (gi: 117938308) (NP_004086, NP_004086.1); Akt1 (gi: 62241012, 62241010, 62241014) (NP_001014431, NP_001014431.1, NP_005154, NP_005154.2, NP_001014432, NP_001014432.1); PI3K (gi: 54792081, 21237724) (NP_006209, NP_006209.2, NP_002640, NP_002640.2); GSK3B (gi: 21361339) (NP_002084, NP_002084.2); HuR (gi: 38201714) (NP_001410, NP_001410.2); and mTOR/FRAP1 (gi: 19924298) (NP_004949, NP_004949.1). Preferred 4E regulon components (components) to be used in certain of the below-described methods are 4E, 4E-BP1, NBS/Nibrin, Pim-1, VEGF, Cyclin D1, Cyclin A2, ODC and HuR. Preferred regulon components include 4E regulon component and is selected from the group consisting of: 4E, 4E-BP1, NBS/Nibrin, Pim-1, VEGF, Cyclin D1, Cyclin A2, ODC, Akt and HuR.

The assays for detecting the level and/or phosphorylation state of 4E and/or at least one 4E regulon component described above may be incorporated into any of a variety of methods for compositions for the identification, diagnosis and monitoring of 4E and 4E regulon component activity and for the discovery of agents that modulate 4E and 4E regulon component activity. Such methods are described extensively in PCT Application US06/049450, filed Dec. 28, 2006 and PCT Application U.S. 07/021,167 filed Oct. 1, 2007, both of which applications are hereby incorporated by reference in their entireties.

In certain embodiments, the level of and/or phosphorylation state of 4E or a 4E regulon component may be compared to the level of and/or phosphorylation state of a control, such as actin or GADPH.

The present invention provides kits for practice of any of the aforedescribed methods. In certain embodiments, kits may comprise internal protein standards and reagents for creating fragments of the standards and target proteins. A kit may further comprise controls, buffers, and instructions for use. Kit components may be packaged for either manual or partially or wholly automated practice of the foregoing methods. Such kits may have a variety of uses, including, for example, imaging, diagnosis, therapy, and other applications.

EXAMPLE

The present invention is further illustrated by the following example which should not be construed as limiting in any way. The contents of all cited references including literature references, issued patents, published or non published patent applications as cited throughout this application are hereby expressly incorporated by reference.

A highly sensitive high throughput mass spectrometry-based quantitative assay for 4E and 4E regulon components has been developed which provides for the single sample multiplexed analysis of 4E and 4E regulon component levels, as well as the potential simultaneous analysis of 4E and 4E regulon component phosphorylation states, providing for the first single sample analysis of the 4E/4E regulon biological pathway.

The mass spectrometry-based assay employs an enrichment method for the target protein(s), which allows the construction of a highly sensitive, high-throughput assay without the use of an antibody. The enrichment step was built into the reduction/alkylation step so that the enrichment method did not introduce any extra steps or reagents to sample preparation. A similar approach may be applicable to development of mass spectrometry-based assay for many other proteins. Other types of non-antibody based enrichment methods have been successfully adopted to develop mass spectrometry-based assay for a variety of different proteins. The throughput of the assay was comparable to or higher than most antibody-based assays. For example, one person processed more than a thousand samples in a week in duplicate without use of a robotic system.

Reagents: Trypsin-gold was purchased from Promega (Cat # V5280). Ammonium carbonate, ammonium bicarbonate, 2-iodoethanol, and triethylphosphine were from Sigma. Mass-spectrometry grade formic acid was from Sigma. Water with 0.1% formic acid was from Fisher Scientific. Acetonitrile (CAN) was from Burdick & Jackson. Synthetic peptides were from Midwest Biotech (Fishers, Ind.).

Sample preparation: Proteins were digested with trypsin before analysis by tandem mass spectrometry coupled in line with high performance liquid chromatography (LC-MS/MS). When target peptide(s) contain a Cys residue, serum/plasma proteins were first reduced and alkylated prior to trypsin digestion. Reduction and alkylation of the serum or plasma proteins was done in one step essentially as described earlier (Hale J E et al (2004) Anal Biochem 333:174-181) with the following modifications. Most importantly, urea was omitted during the coupled reduction/alkylation step. Typically, 10 μL of serum or plasma sample was diluted with 50 μL of ammonium carbonate solution (0.1 M, pH 11) in a polypropylene container and kept on ice followed by mixing with 80 uL of reduction/alkylation cocktail (R/A cocktail) at room temperature. The R/A cocktail was prepared by mixing 0.5 mL 2-iodoethanol, 0.125 mL triethylphosphine, and 24.375 mL of acetonitrile (2-Iodoethanol comes with copper granules as a stabilizer and was filtered through 0.45 μm spin filter (Millipore UFC30HV00) immediately prior to preparation of the R/A cocktail). For smaller volume of samples, total volume was maintained the same by prediluting the serum with phosphate buffered saline (PBS). For larger volume of samples, each reagent volume was increased accordingly. After adding the R/A cocktail to the diluted sample in alkaline pH, the samples were mixed thoroughly and incubated for 1 h at 37° C. with constant shaking Reduced and alkylated samples were centrifuged at 4000 rpm for 4 min then filtered through SolvInert filter plates (Millipore, MSRLN0450) to remove precipitated proteins. Solvents as well as the remaining reduction/alkylation reagents were removed from the filtrate by SpeedVac (miVac DUO concentrator from GeneVac Cat # DUC-12060-000) typically under high heat (75° C.) for 6 h followed by an additional 12-18 h at room temperature. Dried samples were dissolved in 100 μL of 100 mM ammonium bicarbonate solution (ABC) containing trypsin (1 μg of Trypsin-gold per 10 μL initial plasma or serum volume). The best results were obtained when samples were reconstituted with Trypsin-gold immediately after removal from the SpeedVac. Plates were sealed using pierceable heat-sealing aluminum foil (ABgene Cat # AB-0757) using a heat sealer (Eppendorf, Cat # 5390) and incubated with trypsin for 6 h to overnight then filtered through SolvInert filter plates (Millipore, MSRLN0450) before injecting 50 μL to the LC-MS/MS system.

Optimization of the Sample Preparation Procedure for High-Throughput Handling:

Reduction/alkylation reaction was performed in 96-well PCR plates with a tall raised-rim around individual wells (Robbins, Surrey UK, Cat # 1055-00-0). A precursor of an internal standard peptide includes appropriate corresponding internal marker amino acids (e.g. Leu residue with the molecular weight 7 amu higher than the natural counterpart) was prepared in ice-cold ammonium carbonate buffer at 50 nM concentration. Fifty microliter of this solution was dispensed into the PCR plates using a Multiprop (Thermo). The PCR plates were kept chilled on ice while 10 μL of serum or plasma samples were transferred and mixed in duplicate. The R/A cocktail was added at room temperature using an eight-channel multidispense pipet. Prerinsing of the pipet tips was important for accurate delivery of the reagent due to high vapor pressure of the acetonitrile in the solution. Plates were sealed using pierceable heat-sealing aluminum foil (ABgene Cat # AB-0757) using a heat sealer (Eppendorf, Cat # 5390) then mixed thoroughly. Plates were incubated at 37° C. for 1 h with moderate shaking Plates were centrifuged for 4 min at 4000 rpm before peeling the sealing foil. The filtration assembly was prepared by putting a SolvInert filter plate from Millipore (MSRLN0450) on top of the tall raised-rim PCR plate (TempPlate II from USA Scientific, Cat # 1402-9600) as a receiving plate in a locking position. The outlet of this filter plate fits into the raised rim of the receiving plate. The filtration assembly was placed over the sample plate in an upside-down position to form a filtration sandwich so that the raised rim of the sample plate is inserted into individual well of the filter plate. The filtration sandwich was inverted and centrifuged for 1 min at 1000 rpm followed by 4 min at 4000 rpm. The filtrates were dried by SpeedVac as described above and then samples were reconstituted with Trypsin gold, the plates sealed and samples digested at 37° C. overnight. Because the sample preparation method involves two filtration steps, the final sample plate is in the same orientation as the initial reduction/alkylation plate. Enrichment procedures as described above or as suitable for the target protein/peptides are employed as required.

LC-MS/MS of 4E and 4E regulon component peptides: Tryptic peptide derived from 4E and individual 4E regulon components are measured and detected using in-line LC-MS/MS for quantitation of 4E and eIF4E regulon components. In the corresponding standard peptide, the Leu residue (or appropriate internal standard heavy labeled amino acid residue) is uniformly labeled with N15 and C13. Interfering peptides were separated by an HPLC system (Surveyor MS pump from Thermo Finnigan) on a C18 reversed-phase column (XBridge 2.5 um×2.1 mm×50 mm) using the following two-solvent gradient system as required (solvent A, 0.1% formic acid/H$_2$O; solvent B, 0.1% formic acid/acetonitrile). The HPLC column was maintained at 50° C., and the solvents were kept at room temperature and the samples were kept at 4° C. Typically 50 μL of the sample out of total volume of 100 μL was injected using a sample injection loop of 100 μL and peptides was eluted at the times indicated. Two water blank samples were injected before the actual samples so that the HPLC column could reach a steady state. Typical carry-over of pNTTP peptide from previous run was less than 0.1%.

Positive ion mass spectrometry was obtained using an LTQ ion trap quadrupole mass spectrometer equipped with an ESI source (Thermo Finnigan). The entire effluent of the column was directed to the ESI source between 2 and 3 min of HPLC run, whereas the rest was diverted away from the mass spectrometer. To accommodate high flow rate, certain parameters for the instrument had to be adjusted manually including transfer capillary temperature (312° C.) and nitrogen sheath flow.

All microscans were set to one microscan of 50 ms collection of ions for the trap. In the instrument method, the following parameters were used for Mass-selective/Mass spectrometry (MS/MS) conditions; normalized collision energy, 21; activation Q, 0.180; activation time, 50 ms. Three (MS/MS) transitions were measured for both the standard peptide and target 4E and 4E regulon peptides.

Peak Integration and Curve Fitting: Peak integration was done using a processing method within XCaliber software using the following parameters: peak integration method, ICIS; smoothing points, 5; baseline window, 15; area noise factor, 1; peak noise factor, 3 for the standard peptide and 5 for target 4E and 4E regulon peptides; constrain peak width, 5% peak height and 3% tailing factor; advanced option, repetitive noise method. Isotopic distribution and relative intensities among three transitions for each peptide was examined and was confirmed to match with those of synthetic peptides. The ratio between the standard peptide and 4E and 4E regulon target peptides were calculated for each transition then numeric average of the three ratios was obtained. NPI values for the calibration standard samples were fitted to a sigmoidal curve (NPI) Bottom+(Top−Bottom)/(1+10^((log EC50−X)* (Hill Slope))) where X is the logarithm of concentration; Bottom, Top, EC50, and Hill Slope are parameters to be determined by the curve fitting of the data) using a nonlinear curve fitting function of the GraphPad Prism (GraphPad Software, Inc., San Diego, Calif.) with 1/Y^2 as a weighting factor. It was important to use the weighting factor to obtain calibration curve that works over the entire concentration range equally well.

Embodiment of Assay for Detection of 4E Levels and Phosphorylation States: The peptide used to detect 4E was SEQ ID NO: 2: WALWFFK. Its parent mass is 498 and the transitions used were 498->740, 498->627 and 498->371.

The mass spectra determined as described above are shown in FIG. 1.

Other peptides such as those in FIGS. 2 and 3 may be used in the aforedescribed assay to detect the 4E regulon components from which they are derived Embodiment of Assay for Detection of 4E Regulon Component Levels and Phosphorylation States The sequences of 4E regulon components that may be detected using the above-described assay are shown in FIG. 2. Potential digestion product peptides used to analyze each of the components are shown in FIG. 3.

eIF4E Regulon Component Analyte Determination by Mass-Selective Mass Spectrometry: Purified proteins were obtained from a commercial supplier (Origene) and prepared for mass-selective mass-spectrometry using the following procedure. Samples were precipitated with acetone, denatured in 8M urea, reduced with 10 mM DTT in 10 mM ammonium bicarbonate and alkylated with 55 mM iodoacetamide in ammonium bicarbonate. Each sample was then treated with Trypsin (Promega) and incubated overnight at 37 degrees Celsius. The tryptic peptides mixtures obtained using the procedure presented above were injected onto a C18 column (Xbridge C18 2.5 uM-2.1 mm×5 cm). Tryptic peptides were eluted with a linear gradient from 3 to 45% acetonitrile (in water) developed over 120 min at 50 degrees Celsius using a flow rate of 200 uL/min using a Surveyor HPLC pump. Column effluent was electro-sprayed into the LTQ mass spectrometer (Thermo) and peptides detected. Peptides detected were verified by searching against an IPI human database (V360) using Sequest and X!Tandem algorithms. Peptide analyte identification confidence was calculated using a published method (Higgs, R. E. et al (2007) J Proteome Res. 4: 1758-1767). All peptides presented had identification confidence levels exceeding 99%. A summary of peptide analytes identified for eIF4E Regulon components are presented in FIG. 4 and their corresponding mass spectra are presented in FIG. 1.

I claim:

1. A method for simultaneously determining the levels of and/or phosphorylation states of a set of target proteins or peptides in a sample, said target proteins or peptides are eIF4E (NP_001959.1), HuR (NP_001410.2), and at least one eIF4E regulon component selected from the group consisting of Cyclin D1 (NP_444284.1); NBS/Nibrin (NP_002476.2); Pim-1 (NP_002639.1); Cyclin B1 (NP_114172.1); Cyclin A2 (NP_001228.1); ODC (NP_002530.1); VEGF (NP_003367.4); Skp2 (NP_005974.2, NP_116026.1); Cyclin E1 (NP_001229.1); c-myc (NP_002458.2); FGF2 (NP_001997.5); MMP-9 (NP_004985.2); mdm2 (NP_002383.2); caspase-9 (NP_001220.2, NP_127463.1); bc12 (NP_000624.2, NP_000648.2); Bcl/xL (NP_612815.1); Selenoprotein S (NP_060915.2); eIF4E-BP1 (NP_004086.1); Akt1 (NP_001014431.1, NP_005154.2, NP_001014432.1); PI3K (NP_006209.2, NP_002640.2); GSK3B (NP_002084.2); and mTOR/FRAP1 (NP_004949.1), the method comprising:
   (a) adding at least one internal standard protein or peptide corresponding to each target protein of eIF4E, HuR, and the at least one eIF4E regulon component selected from the group consisting of Cyclin D1, NBS/Nibrin, Pim-1, Cyclin B1, Cyclin A2, ODC, VEGF, Skp2, Cyclin E1, c-myc, FGF2, MMP-9, mdm2, caspase-9, bc12, Bcl/xL, Selenoprotein S, eIF4E-BP1, Akt1, PI3K, GSK3B, and mTOR/FRAP1 to the sample;
   (b) fragmenting the target proteins or peptides of eIF4E, HuR, and the at least one eIF4E regulon component and the at least three corresponding internal standard proteins or peptides, thereby generating fragments of the eIF4E, the HuR, and the at least one eIF4E regulon component, and the at least three corresponding internal standard proteins or peptides;
   (c) analyzing the corresponding parent masses and determining amounts of the resultant fragments from step (b) by a mass spectrometry-based method ; and
   (d) using the results from step (c) to determine and quantitate the levels of and/or phosphorylation states of the eIF4E, HuR, and the at least one eIF4E regulon component.

2. The method of claim 1, wherein:
   (a) the at least one eIF4E regulon component is selected from the group consisting of: Cyclin D1 (NP_44284.1); NBS/Nibrin (NP_002476.2); Pim-1 (NP_002639.1); Cyclin A2 (NP_001228.1); ODC (NP_002530.1); VEGF (NP_003367.4); Skp2 (NP_005974.2, NP_116026.1); Cyclin E1 (NP_001229.1); MMP-9 (NP_004985.2); caspase-9 (NP_001220.2, NP_127463.1); Bcl/xL (NP_612815.1); eIF4E-BP1 (NP_004086.1); Akt1 (NP_001014432.1, NP_005154.2, NP_001014431.1); and
   (b) the at least one internal standard protein or peptide corresponding to the at least one eIF4 E regulon component is selected from the group consisting of: Cyclin D1, NBS/Nibrin, Pim-1, Cyclin A2, ODC, VEGF, Skp2, Cyclin E1, MMP-9, caspase-9, Bcl/xL, eIF4E-BP1 and Akt1.

3. The method of claim 1, wherein the mass spectrometry-based method is Liquid chromatography-Mass-selective/Mass Spectrometry (LC-MS/MS).

4. The method of claim 1 wherein in step (b), fragmenting is mediated by the addition of and/or exposure to: chemical agents selected from the group consisting of acid, base, cyanogen bromide, and o-iodobenzoic acid; enzymes or proteases selected from the group consisting of thrombin, trypsin, and chymotrypsin; or mass-spectrometry based fragmentation methods.

5. The method of claim 4 wherein the fragmenting is mediated by the addition of and/or exposure to an enzyme or protease, and said enzyme or protease is selected from the group consisting of thrombin, trypsin, and chymotrypsin.

6. The method of claim 5 wherein said enzyme or protease is trypsin.

7. The method of claim 1, wherein the levels and/or phosphorylation states of:
   (a) eIF4E is determined at least in part on the analysis of the at least one fragment selected from the group consisting of: WALWFFK (SEQ ID NO.: 2), DGIEPMWEDEK (SEQ ID NO.: 152), IAIWTTECENR (SEQ ID NO.: 153), IVIGYQSHADTATK (SEQ ID NO.: 154), TESNQEVANPEHYIK (SEQ ID NO.: 155), MATVEPETTPTPNPPTTEEEK (SEQ ID NO.: 156), FWLETLLCLIGESFDDYSDDVCGAVVNVR (SEQ ID NO.: 157), FDTVEDFWALYNHIQLSSNLMPGCDYSLFK (SEQ ID NO.: 158), and EAVTHIGR (SEQ ID NO.: 159);
   (b) HuR is determined at least in part on the analysis of the at least one fragment selected from the group consisting of: DVEDMFSR (SEQ ID NO.: 139), FAANPNQNK (SEQ ID NO.: 140), VLVDQTTGLSR (SEQ ID NO.: 141), DANLYISGLPR (SEQ ID NO.: 142), FGGPVHHQAQR (SEQ ID NO.: 143), VSYARPSSEVIK (SEQ ID NO.: 144), SLFSSIGEVESAK (SEQ ID NO.: 145), NVALLSQLYHSPAR (SEQ ID NO.: 146), MSNGYEDHMAEDCR (SEQ ID NO.: 147), VAGHSLGYGFVNYVTAK (SEQ ID NO.: 148), TNLIVNYLPQNMTQDELR (SEQ ID NO.: 149), SEAEEAITSFNGHKPPGSSEPITVK (SEQ ID NO.: 150), and GFGFVTMTNYEEAAMAIASLNGYR (SEQ ID NO.: 151);
   (c) Cyclin D1 is determined at least in part on the analysis of the at least one fragment selected from the group consisting of: ETIPLTAEK (SEQ ID NO.: 102), QAQQNMDPK (SEQ ID NO.: 103), SPNNFLSYYR (SEQ ID NO.: 104), AYPDANLLNDR(SEQ ID NO.: 105), AEETCAPSVSYFK(SEQ ID NO.: 106), LQLLGATCMFVASK(SEQ ID NO.: 107), HAQTFVALCATDVK(SEQ ID NO.: 108), IVATWMLEVCEEQK(SEQ ID NO.: 109), ACQEQIEALLESSLR(SEQ ID NO.: 110), MEHQLLCCEVETIR(SEQ ID NO.: 111), CEEEVFPLAMNYLDR(SEQ ID NO.: 112), WNLAAMTPHDFIEHFLSK(SEQ ID NO.: 113), FISNPPSMVAAGSVVAAVQGLNLR(SEQ ID NO.: 114), AAEEEEEEEEEVDLACTPTDVR(SEQ ID NO.: 115), and LCIYTDNSIRPEELLQMELLLVNK(SEQ ID NO.: 116);

(d) NBS/Nibrin is determined at least in part on the analysis of the at least one fragment selected from the group consisting of: ISQENEIGK(SEQ ID NO.: 49), MLSQDAPTVK(SEQ ID NO.: 50), IPNYQLSPTK (SEQ ID NO.: 51), LQDDSEMLPK (SEQ ID NO.: 52), NTELEEWLR(SEQ ID NO.: 53), EESLADDLFR (SEQ ID NO.: 54), LSSAVVFGGGEAR(SEQ ID NO.: 55), ASQQQQTNSIR(SEQ ID NO.: 56), SGDGITFGVFGSK(SEQ ID NO.: 57), DTKPELEIDVK(SEQ ID NO.: 58), QEMEVQNQHAK(SEQ ID NO.: 59), DEENQEMSSCK(SEQ ID NO.: 60), NPSGINDDYGQLK(SEQ ID NO.: 61), WIQSIMDMLQR(SEQ ID NO.: 62), TSSNNNSMVSNTLAK(SEQ ID NO.: 63), NYCDPQGHPSTGLK(SEQ ID NO.: 64), TTTPGPSLSQGVSVDEK(SEQ ID NO.: 65), LPHIIGGSDLIAHHAR(SEQ ID NO.: 66), EMDDVAIEDEVLEQLFK(SEQ ID NO.: 67), IEYEPLVACSSCLDVSGK(SEQ ID NO.: 68), MDIETNDTFSDEAVPESSK(SEQ ID NO.: 69), QPPQIESFYPPLDEPSIGSK(SEQ ID NO.: 70), QGLRPIPEAEIGLAVIFMTTK(SEQ ID NO.: 71), IETSCSLLEQTQPATPSLWK(SEQ ID NO.: 72), TICALICGRPIVKPEYFTEFLK(SEQ ID NO.: 73), EQHLSENEPVDTNSDNNLFTDTDLK(SEQ ID NO.: 74), LMPSAPVNTTTYVADTESEQADTWDLSERPK(SEQ ID NO.: 75), TALNQAILQLGGFTVNNWTEECTHLVMVSVK(SEQ ID NO.: 76), LLPAAGPAGGEPYR(SEQ ID NO.: 160), and KQPPQIESFYPPLDEPSIGSK(SEQ ID NO.: 161);

(e) Pim-1 is determined at least in part on the analysis of the at least one fragment selected from the group consisting of: VSSGFSGVIR(SEQ ID NO.: 34), VPMEVVLLK (SEQ ID NO.: 35), VSDNLPVAIK(SEQ ID NO.: 36), LIDFGSGALLK(SEQ ID NO.: 37), VYSPPEWIR (SEQ ID NO.: 38), AAPCNDLHATK(SEQ ID NO.: 39), DENILIDLNR(SEQ ID NO.: 40), VSSECQHLIR (SEQ ID NO.: 41), DTVYTDFDGTR(SEQ ID NO.: 42), HCHNCGVLHR(SEQ ID NO.: 43), ISDWGELPNGTR(SEQ ID NO.: 44), SFFWQVLEAVR(SEQ ID NO.: 45), EPLESQYQVGPLLGSGGFGSVYSGIR (SEQ ID NO.: 46), SAAVWSLGILLYDMVCGDIPFEHDEEIIR(SEQ ID NO.: 47), LLDWFERPDSFVLILERPEPVQDLFDFITER(SEQ ID NO.: 48), and SLGILLYDMVCGDIPFEHDEEIIR(SEQ ID NO.: 162);

(f) Cyclin A2 is determined at least in part on the analysis of the at the at least one fragment selected from the group consisting of: GLAQQQRPK(SEQ ID NO.: 121), FLSSMSVLR(SEQ ID NO.: 122), QPDITNSMR(SEQ ID NO.: 123), APQHAQQSIR(SEQ ID NO.: 124), MLGNSAPGPATR(SEQ ID NO.: 125), LQLVGTAAMLLASK(SEQ ID NO.: 126), QPAFTIHVDEAEK(SEQ ID 127), EDALAFNSAISLPGPR(SEQ ID NO.: 128), YHGVSLLNPPETLNL(SEQ ID NO.: 129), DLPVNDEHVTVPPWK(SEQ ID NO.: 130), AILVDWLVEVGEEYK(SEQ ID NO.: 131), LQNETLHLAVNYIDR(SEQ ID NO.: 132), VESLAMFLGELSLIDADPYLK(SEQ ID NO.: 133), TGYTLESLKPCLMDLHQTYLK(SEQ ID NO.: 134), FEEIYPPEVAEFVYITDDTYTK(SEQ ID NO.: 135), EAGSALLALQQTALQEDQENINPEK(SEQ ID NO.: 136), YLPSVIAGAAFHLALYTVTGQSWPESLIR (SEQ ID NO.: 137), and VLTFDLAAPTVNQFLTQYFLHQQPANCK(SEQ ID NO.: 138);

(g) ODC is determined at least in part on the analysis of the at the at least one fragment selected from the group consisting of: YFPSDSGVR(SEQ ID NO.: 77), INEVSSSDDK(SEQ ID NO.: 78), TLAATGTGFDCASK(SEQ ID NO.: 79), DAFYVADLGDILK(SEQ ID NO.: 80), FEEITGVINPALDK(SEQ ID NO.: 81), TEIQLVQSLGVPPER(SEQ ID NO.: 82), YYVASAFTLAVNIIAK(SEQ ID 83), YYSSSIWGPTCDGLDR (SEQ ID NO.: 84), YAANNGVQMMTFDSEVELMK (SEQ ID NO.: 85), MNNFGNEEFDCHFLDEGFTAK (SEQ ID NO.: 86), CVFDMGAEVGFSMYLLDIGGGFPGSEDVK(SEQ ID NO.: 87), ELNIDVVGVSFHVGSGCTDPETFVQAISDAR(SEQ ID NO.: 88), INEVSSSDDKDAFYVADLGDILK(SEQ ID NO.: 163), and LLDIGGGFPGSEDVK(SEQ ID NO.: 164);

(h) VEGF is determined at least in part on the analysis of the at least one fragment selected from the group consisting of: AGEAEPSGAAR(SEQ ID NO.: 89), LFVQLLGCSR(SEQ ID NO.: 90), GAEESGPPHSPSR (SEQ ID NO.: 91), QENPCGPCSER(SEQ ID NO.: 92), HLFVQDPQTCK(SEQ ID NO.: 93), GQGPEPAPGGGVEGVGAR(SEQ ID NO.: 94), EEPQPEEGEEEEEK(SEQ ID NO.: 95), QTDTAPSPSYHLLPGR(SEQ ID NO.: 96), KPGSWTGEAAVCADSAPAAR(SEQ ID NO.: 97), WSQAAPMAEGGGQNHHEVVK(SEQ ID NO.: 98), IKPHQGQHIGEMSFLQHNK(SEQ ID NO.: 99), CGGCCNDEGLECVPTEESNITMQIMR(SEQ ID NO.: 100), and ASETMNFLLSWVHWSLALLLYLHHAK(SEQ ID NO.: 101);

(i) Skp2 is determined at least in part on the analysis of the at least one fragment selected from the group consisting of: TLQVFGIVPDGTLQLLK(SEQ ID NO.: 165), LLSQGVIAFR(SEQ ID NO.: 166), LASDESLWQTLDLTGK(SEQ ID NO.: 167), LSDPIVNTLAK (SEQ ID NO.: 168);

(j) Cyclin E1 is determined at least in part on the analysis of the at least one fragment selected from the group consisting of: AILLDWLMEVCEVYK(SEQ ID NO.: 169), DQHFLEQHPLLQPK(SEQ ID NO.: 170), GSPLPVLSWANR(SEQ ID NO.: 171), and YMATQENVVK (SEQ ID NO.: 172);

(k) MMP-9 is determined at least in part on the analysis of the at least one fragment selected from the group consisting of: LGLGADVAQVTGALR(SEQ ID NO.: 173), QLSLPETGELDSATLK(SEQ ID NO.: 174), QSTLVLFPGDLR(SEQ ID NO.: 175), and SLGPALLLLQK (SEQ ID NO.: 176);

(l) Capase-9 is determined at least in part on the analysis of the at least one fragment selected from the group consisting of: LVEELQVDQLWDVLLSR(SEQ ID NO.: 177), DHGFEVASTSPEDESPGSNPEPDATPFQEGLR(SEQ ID NO.: 178), QLIIDLETR(SEQ ID NO.: 179), and KPEVLRPETPRPVDIGSGGFGDVEQK(SEQ ID NO.: 180);

(m) Bcl/xL is determined at least in part on the analysis of the at least one fragment selected from the group consisting of: AFSDLTSQLHITPGTAYQSFEQVVNELFR(SEQ ID NO.: 181), ELVVDFLSYK(SEQ ID NO.: 182), QSFEQVVNELFR(SEQ ID NO.: 183), and EVIPMAAVK(SEQ ID NO.: 184);

(n) eIF4E-BP1 is determined at least in part on the analysis of the at least one fragment selected from the group consisting of: AGGEESQFEMDI(SEQ ID NO.: 117), MSGGSSCSQTPSR(SEQ ID NO.: 118), DLPTIPGVTSPSSDEPPMEASQSHLR(SEQ ID NO.: 119), VVLGDGVQLPPGDYSTTPGGTLFSTTPGGTR(SEQ ID NO.: 120), and RVVLGDGVQLPPGDYSTTPGGTLFSTTPGGTR(SEQ ID NO.: 185);

(o) Akt1 is determined at least in part on the analysis of the at least one fragment selected from the group consisting of: NDGTFIGYK(SEQ ID NO.: 12), YSFQTHDR(SEQ ID NO.: 13), ERPQDVDQR(SEQ ID NO.: 14), QEEEEMDFR(SEQ ID NO.: 15), TFHVETPEER(SEQ ID NO.: 16), VTMNEFEYLK(SEQ ID NO.: 17), DEVAHTLTENR(SEQ ID NO.: 18), LPFYNQDHEK (SEQ ID NO.: 19), CLQWTTVIER(SEQ ID NO.: 20), LFELILMEEIR(SEQ ID NO.: 21), TERPRPNTFIIR (SEQ ID NO.: 22), FFAGIVWQHVYEK(SEQ ID NO.: 23), RPHFPQFSYSASGTA(SEQ ID NO.: 24), EEWTAIQTVADGLK(SEQ ID NO.: 25), LSPPFKPQVTSETDTR(SEQ ID NO.: 26), EAPLNNFSVAQCQLMK (SEQ ID NO.: 27), FYGAEIVSALDYLHSEK(SEQ ID NO.: 28), SGSPSDNSGAEEMEVSLAKPK(SEQ ID NO.: 29), AVDWWGLGVVMYEMMCGR(SEQ ID NO.: 30), LCFVMEYANGGELFFHLSR(SEQ ID NO.: 31), TFCGTPEYLAPEVLEDNDYGR(SEQ ID NO.: 32), YFDEEFTAQMITITPPDQDDSMECVDSER (SEQ ID NO.: 33), and LFELILLMEEIR(SEQ ID NO: 186).

* * * * *

SEQUENCE LISTING

<160> NUMBER OF SEQ ID NOS: 186

<210> SEQ ID NO 1
<211> LENGTH: 217
<212> TYPE: PRT
<213> ORGANISM: Unknown
<220> FEATURE:
<223> OTHER INFORMATION: Description of Unknown: 4E regulon component
      polypeptide

<400> SEQUENCE: 1

Met Ala Thr Val Glu Pro Glu Thr Thr Pro Thr Pro Asn Pro Pro Thr
1               5                   10                  15

Thr Glu Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
    50                  55                  60

Lys Phe Asp Thr Val Glu Asp Phe Trp Ala Leu Tyr Asn His Ile Gln
65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
    130                 135                 140

Tyr Ser Asp Asp Val Cys Gly Ala Val Val Asn Val Arg Ala Lys Gly

```
                145                 150                 155                 160
Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
                180                 185                 190

Ile Val Ile Gly Tyr Gln Ser His Ala Asp Thr Ala Thr Lys Ser Gly
                195                 200                 205

Ser Thr Thr Lys Asn Arg Phe Val Val
                210                 215

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ala Leu Trp Phe Phe Lys
1               5

<210> SEQ ID NO 3
<211> LENGTH: 295
<212> TYPE: PRT
<213> ORGANISM: Homo sapiens

<400> SEQUENCE: 3

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
                20                  25                  30

Lys Ala Glu Glu Thr Cys Ala Pro Ser Val Ser Tyr Phe Lys Cys Val
            35                  40                  45

Gln Lys Glu Val Leu Pro Ser Met Arg Lys Ile Val Ala Thr Trp Met
        50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240
```

```
Pro Asp Cys Leu Arg Ala Cys Gln Glu Gln Ile Glu Ala Leu Leu Glu
            245                 250                 255

Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
            275                 280                 285

Asp Val Arg Asp Val Asp Ile
            290                 295

<210> SEQ ID NO 4
<211> LENGTH: 354
<212> TYPE: PRT
<213> ORGANISM: Homo sapiens

<400> SEQUENCE: 4

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
        50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320
```

Asn Pro Cys Gly Pro Cys Ser Glu Arg Arg Lys His Leu Phe Val Gln
            325                 330                 335

Asp Pro Gln Thr Cys Lys Cys Ser Cys Lys Asn Thr Asp Ser Arg Cys
            340                 345                 350

Lys Met

<210> SEQ ID NO 5
<211> LENGTH: 461
<212> TYPE: PRT
<213> ORGANISM: Homo sapiens

<400> SEQUENCE: 5

Met Asn Asn Phe Gly Asn Glu Glu Phe Asp Cys His Phe Leu Asp Glu
1               5                   10                  15

Gly Phe Thr Ala Lys Asp Ile Leu Asp Gln Lys Ile Asn Glu Val Ser
            20                  25                  30

Ser Ser Asp Asp Lys Asp Ala Phe Tyr Val Ala Asp Leu Gly Asp Ile
        35                  40                  45

Leu Lys Lys His Leu Arg Trp Leu Lys Ala Leu Pro Arg Val Thr Pro
50                  55                  60

Phe Tyr Ala Val Lys Cys Asn Asp Ser Lys Ala Ile Val Lys Thr Leu
65                  70                  75                  80

Ala Ala Thr Gly Thr Gly Phe Asp Cys Ala Ser Lys Thr Glu Ile Gln
                85                  90                  95

Leu Val Gln Ser Leu Gly Val Pro Pro Glu Arg Ile Ile Tyr Ala Asn
            100                 105                 110

Pro Cys Lys Gln Val Ser Gln Ile Lys Tyr Ala Ala Asn Asn Gly Val
        115                 120                 125

Gln Met Met Thr Phe Asp Ser Glu Val Glu Leu Met Lys Val Ala Arg
130                 135                 140

Ala His Pro Lys Ala Lys Leu Val Leu Arg Ile Ala Thr Asp Asp Ser
145                 150                 155                 160

Lys Ala Val Cys Arg Leu Ser Val Lys Phe Gly Ala Thr Leu Arg Thr
                165                 170                 175

Ser Arg Leu Leu Leu Glu Arg Ala Lys Glu Leu Asn Ile Asp Val Val
            180                 185                 190

Gly Val Ser Phe His Val Gly Ser Gly Cys Thr Asp Pro Glu Thr Phe
        195                 200                 205

Val Gln Ala Ile Ser Asp Ala Arg Cys Val Phe Asp Met Gly Ala Glu
210                 215                 220

Val Gly Phe Ser Met Tyr Leu Leu Asp Ile Gly Gly Gly Phe Pro Gly
225                 230                 235                 240

Ser Glu Asp Val Lys Leu Lys Phe Glu Glu Ile Thr Gly Val Ile Asn
                245                 250                 255

Pro Ala Leu Asp Lys Tyr Phe Pro Ser Asp Ser Gly Val Arg Ile Ile
            260                 265                 270

Ala Glu Pro Gly Arg Tyr Tyr Val Ala Ser Ala Phe Thr Leu Ala Val
        275                 280                 285

Asn Ile Ile Ala Lys Lys Ile Val Leu Lys Glu Gln Thr Gly Ser Asp
290                 295                 300

Asp Glu Asp Glu Ser Ser Glu Gln Thr Phe Met Tyr Tyr Val Asn Asp
305                 310                 315                 320

Gly Val Tyr Gly Ser Phe Asn Cys Ile Leu Tyr Asp His Ala His Val
                325                 330                 335

-continued

Lys Pro Leu Leu Gln Lys Arg Pro Lys Pro Asp Glu Lys Tyr Tyr Ser
            340                 345                 350

Ser Ser Ile Trp Gly Pro Thr Cys Asp Gly Leu Asp Arg Ile Val Glu
        355                 360                 365

Arg Cys Asp Leu Pro Glu Met His Val Gly Asp Trp Met Leu Phe Glu
    370                 375                 380

Asn Met Gly Ala Tyr Thr Val Ala Ala Ala Ser Thr Phe Asn Gly Phe
385                 390                 395                 400

Gln Arg Pro Thr Ile Tyr Tyr Val Met Ser Gly Pro Ala Trp Gln Leu
                405                 410                 415

Met Gln Gln Phe Gln Asn Pro Asp Phe Pro Pro Glu Val Glu Glu Gln
            420                 425                 430

Asp Ala Ser Thr Leu Pro Val Ser Cys Ala Trp Glu Ser Gly Met Lys
        435                 440                 445

Arg His Arg Ala Ala Cys Ala Ser Ala Ser Ile Asn Val
    450                 455                 460

<210> SEQ ID NO 6
<211> LENGTH: 672
<212> TYPE: PRT
<213> ORGANISM: Homo sapiens

<400> SEQUENCE: 6

Met Gln Asn Gly Phe Ser Arg Thr Leu Lys Ser Gly Asp Gly Ile Thr
1               5                   10                  15

Phe Gly Val Phe Gly Ser Lys Phe Arg Ile Glu Tyr Glu Pro Leu Val
                20                  25                  30

Ala Cys Ser Ser Cys Leu Asp Val Ser Gly Lys Thr Ala Leu Asn Gln
            35                  40                  45

Ala Ile Leu Gln Leu Gly Gly Phe Thr Val Asn Asn Trp Thr Glu Glu
        50                  55                  60

Cys Thr His Leu Val Met Val Ser Val Lys Val Thr Ile Lys Thr Ile
65                  70                  75                  80

Cys Ala Leu Ile Cys Gly Arg Pro Ile Val Lys Pro Glu Tyr Phe Thr
                85                  90                  95

Glu Phe Leu Lys Ala Val Glu Ser Lys Lys Gln Pro Gln Ile Glu
                100                 105                 110

Ser Phe Tyr Pro Pro Leu Asp Glu Pro Ser Ile Gly Ser Lys Asn Val
            115                 120                 125

Asp Leu Ser Gly Arg Gln Glu Arg Lys Gln Ile Phe Lys Gly Lys Thr
        130                 135                 140

Phe Ile Phe Leu Asn Ala Lys Gln His Lys Lys Leu Ser Ser Ala Val
145                 150                 155                 160

Val Phe Gly Gly Gly Glu Ala Arg Leu Ile Thr Glu Glu Asn Glu Glu
                165                 170                 175

Glu His Asn Phe Phe Leu Ala Pro Gly Thr Cys Val Val Asp Thr Gly
            180                 185                 190

Ile Thr Asn Ser Gln Thr Leu Ile Pro Asp Cys Gln Lys Lys Trp Ile
        195                 200                 205

Gln Ser Ile Met Asp Met Leu Gln Arg Gln Gly Leu Arg Pro Ile Pro
    210                 215                 220

Glu Ala Glu Ile Gly Leu Ala Val Ile Phe Met Thr Thr Lys Asn Tyr
225                 230                 235                 240

Cys Asp Pro Gln Gly His Pro Ser Thr Gly Leu Lys Thr Thr Pro
                245                 250                 255

-continued

Gly Pro Ser Leu Ser Gln Gly Val Ser Val Asp Glu Lys Leu Met Pro
              260                 265                 270

Ser Ala Pro Val Asn Thr Thr Thr Tyr Val Ala Asp Thr Glu Ser Glu
          275                 280                 285

Gln Ala Asp Thr Trp Asp Leu Ser Glu Arg Pro Lys Glu Ile Lys Val
      290                 295                 300

Ser Lys Met Glu Gln Lys Phe Arg Met Leu Ser Gln Asp Ala Pro Thr
305                 310                 315                 320

Val Lys Glu Ser Cys Lys Thr Ser Ser Asn Asn Ser Met Val Ser
              325                 330                 335

Asn Thr Leu Ala Lys Met Arg Ile Pro Asn Tyr Gln Leu Ser Pro Thr
              340                 345                 350

Lys Leu Pro Ser Ile Asn Lys Ser Lys Asp Arg Ala Ser Gln Gln Gln
              355                 360                 365

Gln Thr Asn Ser Ile Arg Asn Tyr Phe Gln Pro Ser Thr Lys Lys Arg
      370                 375                 380

Glu Arg Asp Glu Glu Asn Gln Glu Met Ser Ser Cys Lys Ser Ala Arg
385                 390                 395                 400

Ile Glu Thr Ser Cys Ser Leu Leu Glu Gln Thr Gln Pro Ala Thr Pro
              405                 410                 415

Ser Leu Trp Lys Asn Lys Glu Gln His Leu Ser Glu Asn Glu Pro Val
              420                 425                 430

Asp Thr Asn Ser Asp Asn Asn Leu Phe Thr Asp Thr Asp Leu Lys Ser
      435                 440                 445

Ile Val Lys Asn Ser Ala Ser Lys Ser His Ala Ala Glu Lys Leu Arg
              450                 455                 460

Ser Asn Lys Lys Arg Glu Met Asp Asp Val Ala Ile Glu Asp Glu Val
465                 470                 475                 480

Leu Glu Gln Leu Phe Lys Asp Thr Lys Pro Glu Leu Glu Ile Asp Val
              485                 490                 495

Lys Val Gln Lys Gln Glu Glu Asp Val Asn Val Arg Lys Arg Pro Arg
              500                 505                 510

Met Asp Ile Glu Thr Asn Asp Thr Phe Ser Asp Glu Ala Val Pro Glu
              515                 520                 525

Ser Ser Lys Ile Ser Gln Glu Asn Glu Ile Gly Lys Lys Arg Glu Leu
              530                 535                 540

Lys Glu Asp Ser Leu Trp Ser Ala Lys Glu Ile Ser Asn Asn Asp Lys
545                 550                 555                 560

Leu Gln Asp Asp Ser Glu Met Leu Pro Lys Lys Leu Leu Leu Thr Glu
              565                 570                 575

Phe Arg Ser Leu Val Ile Lys Asn Ser Thr Ser Arg Asn Pro Ser Gly
              580                 585                 590

Ile Asn Asp Asp Tyr Gly Gln Leu Lys Asn Phe Lys Lys Phe Lys Lys
              595                 600                 605

Val Thr Tyr Pro Gly Ala Gly Lys Leu Pro His Ile Ile Gly Gly Ser
              610                 615                 620

Asp Leu Ile Ala His His Ala Arg Lys Asn Thr Glu Leu Glu Glu Trp
625                 630                 635                 640

Leu Arg Gln Glu Met Glu Val Gln Asn Gln His Ala Lys Glu Glu Ser
              645                 650                 655

Leu Ala Asp Asp Leu Phe Arg Tyr Asn Pro Tyr Leu Lys Arg Arg Arg
              660                 665                 670

<210> SEQ ID NO 7

```
<211> LENGTH: 313
<212> TYPE: PRT
<213> ORGANISM: Homo sapiens

<400> SEQUENCE: 7

Met Leu Leu Ser Lys Ile Asn Ser Leu Ala His Leu Arg Ala Ala Pro
1               5                   10                  15

Cys Asn Asp Leu His Ala Thr Lys Leu Ala Pro Gly Lys Glu Lys Glu
            20                  25                  30

Pro Leu Glu Ser Gln Tyr Gln Val Gly Pro Leu Gly Ser Gly Gly
        35                  40                  45

Phe Gly Ser Val Tyr Ser Gly Ile Arg Val Ser Asp Asn Leu Pro Val
50                  55                  60

Ala Ile Lys His Val Glu Lys Asp Arg Ile Ser Asp Trp Gly Glu Leu
65                  70                  75                  80

Pro Asn Gly Thr Arg Val Pro Met Glu Val Val Leu Leu Lys Lys Val
            85                  90                  95

Ser Ser Gly Phe Ser Gly Val Ile Arg Leu Leu Asp Trp Phe Glu Arg
        100                 105                 110

Pro Asp Ser Phe Val Leu Ile Leu Glu Arg Pro Glu Pro Val Gln Asp
    115                 120                 125

Leu Phe Asp Phe Ile Thr Glu Arg Gly Ala Leu Gln Glu Glu Leu Ala
130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 8
<211> LENGTH: 480
<212> TYPE: PRT
<213> ORGANISM: Homo sapiens

<400> SEQUENCE: 8

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30
```

```
Gly Thr Phe Ile Gly Tyr Lys Glu Arg Pro Gln Asp Val Asp Gln Arg
         35                  40                  45

Glu Ala Pro Leu Asn Asn Phe Ser Val Ala Gln Cys Gln Leu Met Lys
 50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
                100                 105                 110

Gln Glu Glu Glu Met Asp Phe Arg Ser Gly Ser Pro Ser Asp Asn
                115                 120                 125

Ser Gly Ala Glu Glu Met Glu Val Ser Leu Ala Lys Pro Lys His Arg
130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
                180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
                340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
                420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
450                 455                 460
```

```
Arg Arg Pro His Phe Pro Gln Phe Ser Tyr Ser Ala Ser Gly Thr Ala
465                 470                 475                 480
```

<210> SEQ ID NO 9
<211> LENGTH: 118
<212> TYPE: PRT
<213> ORGANISM: Homo sapiens

<400> SEQUENCE: 9

```
Met Ser Gly Gly Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
                20                  25                  30

Asp Tyr Ser Thr Thr Pro Gly Gly Thr Leu Phe Ser Thr Thr Pro Gly
            35                  40                  45

Gly Thr Arg Ile Ile Tyr Asp Arg Lys Phe Leu Met Glu Cys Arg Asn
        50                  55                  60

Ser Pro Val Thr Lys Thr Pro Arg Asp Leu Pro Thr Ile Pro Gly
65                  70                  75                  80

Val Thr Ser Pro Ser Ser Asp Glu Pro Pro Met Glu Ala Ser Gln Ser
                85                  90                  95

His Leu Arg Asn Ser Pro Glu Asp Lys Arg Ala Gly Gly Glu Glu Ser
            100                 105                 110

Gln Phe Glu Met Asp Ile
        115
```

<210> SEQ ID NO 10
<211> LENGTH: 432
<212> TYPE: PRT
<213> ORGANISM: Homo sapiens

<400> SEQUENCE: 10

```
Met Leu Gly Asn Ser Ala Pro Gly Pro Ala Thr Arg Glu Ala Gly Ser
1               5                   10                  15

Ala Leu Leu Ala Leu Gln Gln Thr Ala Leu Gln Glu Asp Gln Glu Asn
                20                  25                  30

Ile Asn Pro Glu Lys Ala Ala Pro Val Gln Gln Pro Arg Thr Arg Ala
            35                  40                  45

Ala Leu Ala Val Leu Lys Ser Gly Asn Pro Arg Gly Leu Ala Gln Gln
        50                  55                  60

Gln Arg Pro Lys Thr Arg Arg Val Ala Pro Leu Lys Asp Leu Pro Val
65                  70                  75                  80

Asn Asp Glu His Val Thr Val Pro Pro Trp Lys Ala Asn Ser Lys Gln
                85                  90                  95

Pro Ala Phe Thr Ile His Val Asp Glu Ala Glu Lys Glu Ala Gln Lys
            100                 105                 110

Lys Pro Ala Glu Ser Gln Lys Ile Glu Arg Glu Asp Ala Leu Ala Phe
        115                 120                 125

Asn Ser Ala Ile Ser Leu Pro Gly Pro Arg Lys Pro Leu Val Pro Leu
130                 135                 140

Asp Tyr Pro Met Asp Gly Ser Phe Glu Ser Pro His Thr Met Asp Met
145                 150                 155                 160

Ser Ile Val Leu Glu Asp Glu Lys Pro Val Ser Val Asn Glu Val Pro
                165                 170                 175

Asp Tyr His Glu Asp Ile His Thr Tyr Leu Arg Glu Met Glu Val Lys
            180                 185                 190
```

```
Cys Lys Pro Lys Val Gly Tyr Met Lys Lys Gln Pro Asp Ile Thr Asn
            195                 200                 205

Ser Met Arg Ala Ile Leu Val Asp Trp Leu Val Glu Val Gly Glu Glu
        210                 215                 220

Tyr Lys Leu Gln Asn Glu Thr Leu His Leu Ala Val Asn Tyr Ile Asp
225                 230                 235                 240

Arg Phe Leu Ser Ser Met Ser Val Leu Arg Gly Lys Leu Gln Leu Val
                245                 250                 255

Gly Thr Ala Ala Met Leu Leu Ala Ser Lys Phe Glu Glu Ile Tyr Pro
                260                 265                 270

Pro Glu Val Ala Glu Phe Val Tyr Ile Thr Asp Asp Thr Tyr Thr Lys
                275                 280                 285

Lys Gln Val Leu Arg Met Glu His Leu Val Leu Lys Val Leu Thr Phe
                290                 295                 300

Asp Leu Ala Ala Pro Thr Val Asn Gln Phe Leu Thr Gln Tyr Phe Leu
305                 310                 315                 320

His Gln Gln Pro Ala Asn Cys Lys Val Glu Ser Leu Ala Met Phe Leu
                325                 330                 335

Gly Glu Leu Ser Leu Ile Asp Ala Asp Pro Tyr Leu Lys Tyr Leu Pro
                340                 345                 350

Ser Val Ile Ala Gly Ala Ala Phe His Leu Ala Leu Tyr Thr Val Thr
                355                 360                 365

Gly Gln Ser Trp Pro Glu Ser Leu Ile Arg Lys Thr Gly Tyr Thr Leu
                370                 375                 380

Glu Ser Leu Lys Pro Cys Leu Met Asp Leu His Gln Thr Tyr Leu Lys
385                 390                 395                 400

Ala Pro Gln His Ala Gln Gln Ser Ile Arg Glu Lys Tyr Lys Asn Ser
                405                 410                 415

Lys Tyr His Gly Val Ser Leu Leu Asn Pro Pro Glu Thr Leu Asn Leu
                420                 425                 430

<210> SEQ ID NO 11
<211> LENGTH: 326
<212> TYPE: PRT
<213> ORGANISM: Homo sapiens

<400> SEQUENCE: 11

Met Ser Asn Gly Tyr Glu Asp His Met Ala Glu Asp Cys Arg Gly Asp
1               5                   10                  15

Ile Gly Arg Thr Asn Leu Ile Val Asn Tyr Leu Pro Gln Asn Met Thr
                20                  25                  30

Gln Asp Glu Leu Arg Ser Leu Phe Ser Ser Ile Gly Glu Val Glu Ser
            35                  40                  45

Ala Lys Leu Ile Arg Asp Lys Val Ala Gly His Ser Leu Gly Tyr Gly
        50                  55                  60

Phe Val Asn Tyr Val Thr Ala Lys Asp Ala Glu Arg Ala Ile Asn Thr
65                  70                  75                  80

Leu Asn Gly Leu Arg Leu Gln Ser Lys Thr Ile Lys Val Ser Tyr Ala
                85                  90                  95

Arg Pro Ser Ser Glu Val Ile Lys Asp Ala Asn Leu Tyr Ile Ser Gly
                100                 105                 110

Leu Pro Arg Thr Met Thr Gln Lys Asp Val Glu Asp Met Phe Ser Arg
            115                 120                 125

Phe Gly Arg Ile Ile Asn Ser Arg Val Leu Val Asp Gln Thr Thr Gly
        130                 135                 140
```

```
Leu Ser Arg Gly Val Ala Phe Ile Arg Phe Asp Lys Arg Ser Glu Ala
145                 150                 155                 160

Glu Glu Ala Ile Thr Ser Phe Asn Gly His Lys Pro Pro Gly Ser Ser
                165                 170                 175

Glu Pro Ile Thr Val Lys Phe Ala Ala Asn Pro Asn Gln Asn Lys Asn
            180                 185                 190

Val Ala Leu Leu Ser Gln Leu Tyr His Ser Pro Ala Arg Arg Phe Gly
        195                 200                 205

Gly Pro Val His His Gln Ala Gln Arg Phe Arg Phe Ser Pro Met Gly
    210                 215                 220

Val Asp His Met Ser Gly Leu Ser Gly Val Asn Val Pro Gly Asn Ala
225                 230                 235                 240

Ser Ser Gly Trp Cys Ile Phe Ile Tyr Asn Leu Gly Gln Asp Ala Asp
                245                 250                 255

Glu Gly Ile Leu Trp Gln Met Phe Gly Pro Phe Gly Ala Val Thr Asn
                260                 265                 270

Val Lys Val Ile Arg Asp Phe Asn Thr Asn Lys Cys Lys Gly Phe Gly
            275                 280                 285

Phe Val Thr Met Thr Asn Tyr Glu Glu Ala Ala Met Ala Ile Ala Ser
        290                 295                 300

Leu Asn Gly Tyr Arg Leu Gly Asp Lys Ile Leu Gln Val Ser Phe Lys
305                 310                 315                 320

Thr Asn Lys Ser His Lys
                325

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Asp Gly Thr Phe Ile Gly Tyr Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ser Phe Gln Thr His Asp Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Arg Pro Gln Asp Val Asp Gln Arg
1               5

<210> SEQ ID NO 15
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Glu Glu Glu Glu Met Asp Phe Arg
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe His Val Glu Thr Pro Glu Glu Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Thr Met Asn Glu Phe Glu Tyr Leu Lys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Glu Val Ala His Thr Leu Thr Glu Asn Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Phe Tyr Asn Gln Asp His Glu Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Leu Gln Trp Thr Thr Val Ile Glu Arg
```

-continued

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Phe Glu Leu Ile Leu Met Glu Glu Ile Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Glu Arg Pro Arg Pro Asn Thr Phe Ile Ile Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Phe Ala Gly Ile Val Trp Gln His Val Tyr Glu Lys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Pro His Phe Pro Gln Phe Ser Tyr Ser Ala Ser Gly Thr Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Glu Trp Thr Thr Ala Ile Gln Thr Val Ala Asp Gly Leu Lys
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Leu Ser Pro Pro Phe Lys Pro Gln Val Thr Ser Glu Thr Asp Thr Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ala Pro Leu Asn Asn Phe Ser Val Ala Gln Cys Gln Leu Met Lys
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Tyr Gly Ala Glu Ile Val Ser Ala Leu Asp Tyr Leu His Ser Glu
1               5                   10                  15

Lys

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Ser Pro Ser Asp Asn Ser Gly Ala Glu Glu Met Glu Val Ser
1               5                   10                  15

Leu Ala Lys Pro Lys
            20

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Val Asp Trp Trp Gly Leu Gly Val Val Met Tyr Glu Met Met Cys
1               5                   10                  15

Gly Arg

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

```
Leu Cys Phe Val Met Glu Tyr Ala Asn Gly Gly Glu Leu Phe Phe His
1               5                   10                  15

Leu Ser Arg
```

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Thr Phe Cys Gly Thr Pro Glu Tyr Leu Ala Pro Glu Val Leu Glu Asp
1               5                   10                  15

Asn Asp Tyr Gly Arg
            20
```

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Tyr Phe Asp Glu Glu Phe Thr Ala Gln Met Ile Thr Ile Thr Pro Pro
1               5                   10                  15

Asp Gln Asp Asp Ser Met Glu Cys Val Asp Ser Glu Arg
            20                  25
```

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Val Ser Ser Gly Phe Ser Gly Val Ile Arg
1               5                   10
```

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Val Pro Met Glu Val Val Leu Leu Lys
1               5
```

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Val Ser Asp Asn Leu Pro Val Ala Ile Lys
1               5                   10
```

```
<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Ile Asp Phe Gly Ser Gly Ala Leu Leu Lys
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Tyr Ser Pro Pro Glu Trp Ile Arg
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Pro Cys Asn Asp Leu His Ala Thr Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Glu Asn Ile Leu Ile Asp Leu Asn Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Ser Ser Glu Cys Gln His Leu Ile Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 42

Asp Thr Val Tyr Thr Asp Phe Asp Gly Thr Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Cys His Asn Cys Gly Val Leu His Arg
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Asp Trp Gly Glu Leu Pro Asn Gly Thr Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Phe Phe Trp Gln Val Leu Glu Ala Val Arg
1               5                   10

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Pro Leu Glu Ser Gln Tyr Gln Val Gly Pro Leu Leu Gly Ser Gly
1               5                   10                  15

Gly Phe Gly Ser Val Tyr Ser Gly Ile Arg
            20                  25

<210> SEQ ID NO 47
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ala Ala Val Trp Ser Leu Gly Ile Leu Leu Tyr Asp Met Val Cys
1               5                   10                  15

Gly Asp Ile Pro Phe Glu His Asp Glu Glu Ile Ile Arg
            20                  25
```

```
<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Leu Asp Trp Phe Glu Arg Pro Asp Ser Phe Val Leu Ile Leu Glu
1               5                   10                  15

Arg Pro Glu Pro Val Gln Asp Leu Phe Asp Phe Ile Thr Glu Arg
            20                  25                  30

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Ser Gln Glu Asn Glu Ile Gly Lys
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Leu Ser Gln Asp Ala Pro Thr Val Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Pro Asn Tyr Gln Leu Ser Pro Thr Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gln Asp Asp Ser Glu Met Leu Pro Lys
1               5                   10

<210> SEQ ID NO 53
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 53

Asn Thr Glu Leu Glu Glu Trp Leu Arg
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Glu Ser Leu Ala Asp Asp Leu Phe Arg
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ser Ser Ala Val Val Phe Gly Gly Gly Glu Ala Arg
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ser Gln Gln Gln Gln Thr Asn Ser Ile Arg
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Gly Asp Gly Ile Thr Phe Gly Val Phe Gly Ser Lys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Thr Lys Pro Glu Leu Glu Ile Asp Val Lys
1               5                   10

<210> SEQ ID NO 59

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Glu Met Glu Val Gln Asn Gln His Ala Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Glu Glu Asn Gln Glu Met Ser Ser Cys Lys
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Pro Ser Gly Ile Asn Asp Asp Tyr Gly Gln Leu Lys
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Ile Gln Ser Ile Met Asp Met Leu Gln Arg
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Ser Ser Asn Asn Asn Ser Met Val Ser Asn Thr Leu Ala Lys
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Tyr Cys Asp Pro Gln Gly His Pro Ser Thr Gly Leu Lys
```

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Thr Thr Thr Pro Gly Pro Ser Leu Ser Gln Gly Val Ser Val Asp Glu
1               5                   10                  15
Lys

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Leu Pro His Ile Ile Gly Gly Ser Asp Leu Ile Ala His His Ala Arg
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Glu Met Asp Asp Val Ala Ile Glu Asp Glu Val Leu Glu Gln Leu Phe
1               5                   10                  15
Lys

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Ile Glu Tyr Glu Pro Leu Val Ala Cys Ser Ser Cys Leu Asp Val Ser
1               5                   10                  15
Gly Lys

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Met Asp Ile Glu Thr Asn Asp Thr Phe Ser Asp Glu Ala Val Pro Glu
1               5                   10                  15
Ser Ser Lys

```
<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Pro Pro Gln Ile Glu Ser Phe Tyr Pro Pro Leu Asp Glu Pro Ser
1               5                   10                  15

Ile Gly Ser Lys
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gly Leu Arg Pro Ile Pro Glu Ala Glu Ile Gly Leu Ala Val Ile
1               5                   10                  15

Phe Met Thr Thr Lys
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Glu Thr Ser Cys Ser Leu Leu Glu Gln Thr Gln Pro Ala Thr Pro
1               5                   10                  15

Ser Leu Trp Lys
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Ile Cys Ala Leu Ile Cys Gly Arg Pro Ile Val Lys Pro Glu Tyr
1               5                   10                  15

Phe Thr Glu Phe Leu Lys
            20

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Gln His Leu Ser Glu Asn Glu Pro Val Asp Thr Asn Ser Asp Asn
```

```
                1               5                   10                  15
Asn Leu Phe Thr Asp Thr Asp Leu Lys
            20                  25

<210> SEQ ID NO 75
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Met Pro Ser Ala Pro Val Asn Thr Thr Thr Tyr Val Ala Asp Thr
1               5                   10                  15

Glu Ser Glu Gln Ala Asp Thr Trp Asp Leu Ser Glu Arg Pro Lys
            20                  25                  30

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Thr Ala Leu Asn Gln Ala Ile Leu Gln Leu Gly Gly Phe Thr Val Asn
1               5                   10                  15

Asn Trp Thr Glu Glu Cys Thr His Leu Val Met Val Ser Val Lys
            20                  25                  30

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Phe Pro Ser Asp Ser Gly Val Arg
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Asn Glu Val Ser Ser Ser Asp Asp Lys
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Leu Ala Ala Thr Gly Thr Gly Phe Asp Cys Ala Ser Lys
1               5                   10
```

```
<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ala Phe Tyr Val Ala Asp Leu Gly Asp Ile Leu Lys
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Glu Glu Ile Thr Gly Val Ile Asn Pro Ala Leu Asp Lys
1               5                   10

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Glu Ile Gln Leu Val Gln Ser Leu Gly Val Pro Pro Glu Arg
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Tyr Val Ala Ser Ala Phe Thr Leu Ala Val Asn Ile Ile Ala Lys
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Tyr Ser Ser Ser Ile Trp Gly Pro Thr Cys Asp Gly Leu Asp Arg
1               5                   10                  15

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 85

Tyr Ala Ala Asn Asn Gly Val Gln Met Met Thr Phe Asp Ser Glu Val
1               5                   10                  15

Glu Leu Met Lys
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Met Asn Asn Phe Gly Asn Glu Glu Phe Asp Cys His Phe Leu Asp Glu
1               5                   10                  15

Gly Phe Thr Ala Lys
            20

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Val Phe Asp Met Gly Ala Glu Val Gly Phe Ser Met Tyr Leu Leu
1               5                   10                  15

Asp Ile Gly Gly Gly Phe Pro Gly Ser Glu Asp Val Lys
            20                  25

<210> SEQ ID NO 88
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Leu Asn Ile Asp Val Val Gly Val Ser Phe His Val Gly Ser Gly
1               5                   10                  15

Cys Thr Asp Pro Glu Thr Phe Val Gln Ala Ile Ser Asp Ala Arg
            20                  25                  30

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Gly Glu Ala Glu Pro Ser Gly Ala Ala Arg
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
-continued
                peptide

<400> SEQUENCE: 90

Leu Phe Val Gln Leu Leu Gly Cys Ser Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ala Glu Glu Ser Gly Pro Pro His Ser Pro Ser Arg
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Glu Asn Pro Cys Gly Pro Cys Ser Glu Arg
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Leu Phe Val Gln Asp Pro Gln Thr Cys Lys
1               5                   10

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gln Gly Pro Glu Pro Ala Pro Gly Gly Val Glu Gly Val Gly
1               5                   10                  15

Ala Arg

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Glu Pro Gln Pro Glu Glu Gly Glu Glu Glu Glu Glu Lys
1               5                   10
```

```
<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Thr Asp Thr Ala Pro Ser Pro Ser Tyr His Leu Leu Pro Gly Arg
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Pro Gly Ser Trp Thr Gly Glu Ala Ala Val Cys Ala Asp Ser Ala
1               5                   10                  15

Pro Ala Ala Arg
            20

<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Ser Gln Ala Ala Pro Met Ala Glu Gly Gly Gly Gln Asn His His
1               5                   10                  15

Glu Val Val Lys
            20

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Lys Pro His Gln Gly Gln His Ile Gly Glu Met Ser Phe Leu Gln
1               5                   10                  15

His Asn Lys

<210> SEQ ID NO 100
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Gly Gly Cys Cys Asn Asp Glu Gly Leu Glu Cys Val Pro Thr Glu
1               5                   10                  15

Glu Ser Asn Ile Thr Met Gln Ile Met Arg
            20                  25
```

```
<210> SEQ ID NO 101
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Ser Glu Thr Met Asn Phe Leu Leu Ser Trp Val His Trp Ser Leu
1               5                   10                  15

Ala Leu Leu Leu Tyr Leu His His Ala Lys
            20                  25

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Thr Ile Pro Leu Thr Ala Glu Lys
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Ala Gln Gln Asn Met Asp Pro Lys
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Pro Asn Asn Phe Leu Ser Tyr Tyr Arg
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Tyr Pro Asp Ala Asn Leu Leu Asn Asp Arg
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 106

Ala Glu Glu Thr Cys Ala Pro Ser Val Ser Tyr Phe Lys
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Gln Leu Leu Gly Ala Thr Cys Met Phe Val Ala Ser Lys
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Ala Gln Thr Phe Val Ala Leu Cys Ala Thr Asp Val Lys
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Val Ala Thr Trp Met Leu Glu Val Cys Glu Glu Gln Lys
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Cys Gln Glu Gln Ile Glu Ala Leu Leu Glu Ser Ser Leu Arg
1               5                   10                  15

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Met Glu His Gln Leu Leu Cys Cys Glu Val Glu Thr Ile Arg
1               5                   10

<210> SEQ ID NO 112
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Glu Glu Glu Val Phe Pro Leu Ala Met Asn Tyr Leu Asp Arg
1               5                   10                  15

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Asn Leu Ala Ala Met Thr Pro His Asp Phe Ile Glu His Phe Leu
1               5                   10                  15

Ser Lys

<210> SEQ ID NO 114
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Ile Ser Asn Pro Pro Ser Met Val Ala Ala Gly Ser Val Val Ala
1               5                   10                  15

Ala Val Gln Gly Leu Asn Leu Arg
            20

<210> SEQ ID NO 115
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ala Glu Glu Glu Glu Glu Glu Glu Glu Glu Val Asp Leu Ala Cys
1               5                   10                  15

Thr Pro Thr Asp Val Arg
            20

<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Leu Cys Ile Tyr Thr Asp Asn Ser Ile Arg Pro Glu Glu Leu Leu Gln
1               5                   10                  15

Met Glu Leu Leu Leu Val Asn Lys
            20

<210> SEQ ID NO 117
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Gly Gly Glu Glu Ser Gln Phe Glu Met Asp Ile
1               5                  10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Met Ser Gly Gly Ser Ser Cys Ser Gln Thr Pro Ser Arg
1               5                  10

<210> SEQ ID NO 119
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Leu Pro Thr Ile Pro Gly Val Thr Ser Pro Ser Asp Glu Pro
1               5                  10                  15

Pro Met Glu Ala Ser Gln Ser His Leu Arg
            20                  25

<210> SEQ ID NO 120
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Val Val Leu Gly Asp Gly Val Gln Leu Pro Pro Gly Asp Tyr Ser Thr
1               5                  10                  15

Thr Pro Gly Gly Thr Leu Phe Ser Thr Thr Pro Gly Gly Thr Arg
            20                  25                  30

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Leu Ala Gln Gln Gln Arg Pro Lys
1               5

<210> SEQ ID NO 122
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 122

Phe Leu Ser Ser Met Ser Val Leu Arg
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Pro Asp Ile Thr Asn Ser Met Arg
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Pro Gln His Ala Gln Gln Ser Ile Arg
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Met Leu Gly Asn Ser Ala Pro Gly Pro Ala Thr Arg
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Gln Leu Val Gly Thr Ala Ala Met Leu Leu Ala Ser Lys
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Pro Ala Phe Thr Ile His Val Asp Glu Ala Glu Lys
1               5                   10

<210> SEQ ID NO 128

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Asp Ala Leu Ala Phe Asn Ser Ala Ile Ser Leu Pro Gly Pro Arg
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr His Gly Val Ser Leu Leu Asn Pro Pro Glu Thr Leu Asn Leu
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Leu Pro Val Asn Asp Glu His Val Thr Val Pro Pro Trp Lys
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ile Leu Val Asp Trp Leu Val Glu Val Gly Glu Glu Tyr Lys
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Leu Gln Asn Glu Thr Leu His Leu Ala Val Asn Tyr Ile Asp Arg
1               5                   10                  15

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Val Glu Ser Leu Ala Met Phe Leu Gly Glu Leu Ser Leu Ile Asp Ala
```

```
1               5                   10                  15

Asp Pro Tyr Leu Lys
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Gly Tyr Thr Leu Glu Ser Leu Lys Pro Cys Leu Met Asp Leu His
1               5                   10                  15

Gln Thr Tyr Leu Lys
            20

<210> SEQ ID NO 135
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Phe Glu Glu Ile Tyr Pro Pro Glu Val Ala Glu Phe Val Tyr Ile Thr
1               5                   10                  15

Asp Asp Thr Tyr Thr Lys
            20

<210> SEQ ID NO 136
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Ala Gly Ser Ala Leu Leu Ala Leu Gln Gln Thr Ala Leu Gln Glu
1               5                   10                  15

Asp Gln Glu Asn Ile Asn Pro Glu Lys
            20                  25

<210> SEQ ID NO 137
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr Leu Pro Ser Val Ile Ala Gly Ala Ala Phe His Leu Ala Leu Tyr
1               5                   10                  15

Thr Val Thr Gly Gln Ser Trp Pro Glu Ser Leu Ile Arg
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 138

Val Leu Thr Phe Asp Leu Ala Ala Pro Thr Val Asn Gln Phe Leu Thr
1               5                   10                  15

Gln Tyr Phe Leu His Gln Gln Pro Ala Asn Cys Lys
            20                  25

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Val Glu Asp Met Phe Ser Arg
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Phe Ala Ala Asn Pro Asn Gln Asn Lys
1               5

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Val Leu Val Asp Gln Thr Thr Gly Leu Ser Arg
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Ala Asn Leu Tyr Ile Ser Gly Leu Pro Arg
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Phe Gly Gly Pro Val His His Gln Ala Gln Arg
1               5                   10
```

```
<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Ser Tyr Ala Arg Pro Ser Ser Glu Val Ile Lys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Leu Phe Ser Ser Ile Gly Glu Val Glu Ser Ala Lys
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asn Val Ala Leu Leu Ser Gln Leu Tyr His Ser Pro Ala Arg
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Met Ser Asn Gly Tyr Glu Asp His Met Ala Glu Asp Cys Arg
1               5                   10

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Val Ala Gly His Ser Leu Gly Tyr Gly Phe Val Asn Tyr Val Thr Ala
1               5                   10                  15

Lys

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 149

Thr Asn Leu Ile Val Asn Tyr Leu Pro Gln Asn Met Thr Gln Asp Glu
1               5                   10                  15

Leu Arg

<210> SEQ ID NO 150
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Glu Ala Glu Ala Ile Thr Ser Phe Asn Gly His Lys Pro Pro
1               5                   10                  15

Gly Ser Ser Glu Pro Ile Thr Val Lys
            20                  25

<210> SEQ ID NO 151
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Phe Gly Phe Val Thr Met Thr Asn Tyr Glu Glu Ala Ala Met Ala
1               5                   10                  15

Ile Ala Ser Leu Asn Gly Tyr Arg
            20

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Gly Ile Glu Pro Met Trp Glu Asp Glu Lys
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Ala Ile Trp Thr Thr Glu Cys Glu Asn Arg
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

```
Ile Val Ile Gly Tyr Gln Ser His Ala Asp Thr Ala Thr Lys
1               5                   10

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Glu Ser Asn Gln Glu Val Ala Asn Pro Glu His Tyr Ile Lys
1               5                   10                  15

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Met Ala Thr Val Glu Pro Glu Thr Thr Pro Thr Pro Asn Pro Pro Thr
1               5                   10                  15

Thr Glu Glu Glu Lys
            20

<210> SEQ ID NO 157
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Trp Leu Glu Thr Leu Leu Cys Leu Ile Gly Glu Ser Phe Asp Asp
1               5                   10                  15

Tyr Ser Asp Asp Val Cys Gly Ala Val Val Asn Val Arg
            20                  25

<210> SEQ ID NO 158
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Phe Asp Thr Val Glu Asp Phe Trp Ala Leu Tyr Asn His Ile Gln Leu
1               5                   10                  15

Ser Ser Asn Leu Met Pro Gly Cys Asp Tyr Ser Leu Phe Lys
            20                  25                  30

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159
```

```
Glu Ala Val Thr His Ile Gly Arg
1               5

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Leu Leu Pro Ala Ala Gly Pro Ala Gly Gly Glu Pro Tyr Arg
1               5                   10

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Lys Gln Pro Pro Gln Ile Glu Ser Phe Tyr Pro Pro Leu Asp Glu Pro
1               5                   10                  15

Ser Ile Gly Ser Lys
            20

<210> SEQ ID NO 162
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Leu Gly Ile Leu Tyr Asp Met Val Cys Gly Asp Ile Pro Phe
1               5                   10                  15

Glu His Asp Glu Glu Ile Ile Arg
            20

<210> SEQ ID NO 163
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Asn Glu Val Ser Ser Ser Asp Asp Lys Asp Ala Phe Tyr Val Ala
1               5                   10                  15

Asp Leu Gly Asp Ile Leu Lys
            20

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Leu Asp Ile Gly Gly Gly Phe Pro Gly Ser Glu Asp Val Lys
```

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Leu Gln Val Phe Gly Ile Val Pro Asp Gly Thr Leu Gln Leu Leu
1               5                   10                  15

Lys

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Leu Ser Gln Gly Val Ile Ala Phe Arg
1               5                   10

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Ala Ser Asp Glu Ser Leu Trp Gln Thr Leu Asp Leu Thr Gly Lys
1               5                   10                  15

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Ser Asp Pro Ile Val Asn Thr Leu Ala Lys
1               5                   10

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Ile Leu Leu Asp Trp Leu Met Glu Val Cys Glu Val Tyr Lys
1               5                   10                  15

<210> SEQ ID NO 170
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 170

Asp Gln His Phe Leu Glu Gln His Pro Leu Leu Gln Pro Lys
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Ser Pro Leu Pro Val Leu Ser Trp Ala Asn Arg
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Tyr Met Ala Thr Gln Glu Asn Val Val Lys
1               5                   10

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Gly Leu Gly Ala Asp Val Ala Gln Val Thr Gly Ala Leu Arg
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Leu Ser Leu Pro Glu Thr Gly Glu Leu Asp Ser Ala Thr Leu Lys
1               5                   10                  15

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Ser Thr Leu Val Leu Phe Pro Gly Asp Leu Arg
1               5                   10

<210> SEQ ID NO 176
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Leu Gly Pro Ala Leu Leu Leu Leu Gln Lys
1               5                   10

<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Val Glu Glu Leu Gln Val Asp Gln Leu Trp Asp Val Leu Leu Ser
1               5                   10                  15

Arg

<210> SEQ ID NO 178
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp His Gly Phe Glu Val Ala Ser Thr Ser Pro Glu Asp Glu Ser Pro
1               5                   10                  15

Gly Ser Asn Pro Glu Pro Asp Ala Thr Pro Phe Gln Glu Gly Leu Arg
                20                  25                  30

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Leu Ile Ile Asp Leu Glu Thr Arg
1               5

<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Lys Pro Glu Val Leu Arg Pro Glu Thr Pro Arg Pro Val Asp Ile Gly
1               5                   10                  15

Ser Gly Gly Phe Gly Asp Val Glu Gln Lys
                20                  25

<210> SEQ ID NO 181
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 181

Ala Phe Ser Asp Leu Thr Ser Gln Leu His Ile Thr Pro Gly Thr Ala
1               5                   10                  15

Tyr Gln Ser Phe Glu Gln Val Val Asn Glu Leu Phe Arg
            20                  25

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Glu Leu Val Val Asp Phe Leu Ser Tyr Lys
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Ser Phe Glu Gln Val Val Asn Glu Leu Phe Arg
1               5                   10

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Val Ile Pro Met Ala Ala Val Lys
1               5

<210> SEQ ID NO 185
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Arg Val Val Leu Gly Asp Gly Val Gln Leu Pro Pro Gly Asp Tyr Ser
1               5                   10                  15

Thr Thr Pro Gly Gly Thr Leu Phe Ser Thr Thr Pro Gly Gly Thr Arg
            20                  25                  30
```

```
<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Leu Phe Glu Leu Ile Leu Leu Met Glu Glu Ile Arg
1               5                   10
```